(12) United States Patent
Gao et al.

(10) Patent No.: US 11,404,648 B2
(45) Date of Patent: Aug. 2, 2022

(54) AROMATIC HETEROCYCLIC COMPOUND AND ORGANIC LIGHT-EMITTING DISPLAY DEVICE

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Wei Gao, Shanghai (CN); Xiangcheng Wang, Shanghai (CN); Lei Zhang, Shanghai (CN); Jinghua Niu, Shanghai (CN); Yan Lu, Shanghai (CN); Changxuan Fan, Shanghai (CN); Gaojun Huang, Shanghai (CN); Ping An, Shanghai (CN)

(73) Assignees: WUHAN TIANMA MICROELECTRONICS CO., LTD, Wuhan (CN); WUHAN TIANMA MICROELECTRONICS CO., LTD. SHANGHAI BRANCH, Shanghai (CN)

( * ) Notice: Subject to any disclaimer, the term of this patent is extended or adjusted under 35 U.S.C. 154(b) by 607 days.

(21) Appl. No.: 16/222,935

(22) Filed: Dec. 17, 2018

(65) Prior Publication Data
US 2020/0035931 A1 Jan. 30, 2020

(30) Foreign Application Priority Data
Jul. 27, 2018 (CN) .......................... 201810844138.8

(51) Int. Cl.
C07D 495/04 (2006.01)
H01L 51/00 (2006.01)
(Continued)

(52) U.S. Cl.
CPC ........ H01L 51/0074 (2013.01); C07D 495/04 (2013.01); C07F 5/027 (2013.01);
(Continued)

(58) Field of Classification Search
None
See application file for complete search history.

(56) References Cited

FOREIGN PATENT DOCUMENTS

| CN | 1956988 A | 5/2007 |
|---|---|---|
| CN | 101585972 A | 11/2009 |

(Continued)

OTHER PUBLICATIONS

First Office Action dated Aug. 21, 2019, for Chinese Patent Application No. 201810844138.8. (with English translation, 16 pages).
(Continued)

*Primary Examiner* — Clinton A Brooks
(74) *Attorney, Agent, or Firm* — Christensen O'Connor Johnson Kindness PLLC

(57) ABSTRACT

The present disclosure provides an aromatic heterocyclic compound having property of thermally activated delayed fluorescence (TADF). The aromatic heterocyclic compound has a structure represented by Formula (I), in which $X_1$ and $X_2$ each is S, O, Se, or C; D is an electron donor, A is an electron acceptor; m is a number of the electron donor D, and the m electron donors D are the same or different; n is a number of the electron acceptor, and the n electron acceptors are the same or different; and m and n are 1 or 2. The aromatic heterocyclic compound provides a high luminescence efficiency. Organic light-emitting display devices including such aromatic heterocyclic compound have improved luminescence efficiency, lower cost and longer service life by using the aromatic heterocyclic compound as a light-emitting material, a host material, or a guest material.

(Continued)

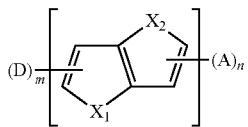

(I)

22 Claims, 3 Drawing Sheets

(51) Int. Cl.
*C07F 5/02* (2006.01)
*C09K 11/06* (2006.01)
*H01L 51/50* (2006.01)

(52) U.S. Cl.
CPC ............ *C09K 11/06* (2013.01); *H01L 51/008* (2013.01); *H01L 51/0067* (2013.01); *H01L 51/0072* (2013.01); *C09K 2211/1018* (2013.01); *H01L 51/5016* (2013.01); *H01L 2251/552* (2013.01)

(56) References Cited

FOREIGN PATENT DOCUMENTS

| | | |
|---|---|---|
| CN | 104662025 A | 5/2015 |
| CN | 106883240 A | 6/2017 |
| JP | 2010205815 A | 9/2010 |
| TW | I623541 B | 5/2018 |
| WO | 2018033654 A1 | 2/2018 |

OTHER PUBLICATIONS

Bui, Thanh-Tuan et al., "Carbazol-N-yl and diphenylamino end-capped triphenylamine-based molecular glasses synthesis, thermal, and optical properties," Tetrahedron Letters 54:4277-4280, 2013.
STN Registry, RN 1027223-78-4, ACS, Jun. 11, 2008.
Second Office Action, dated May 11, 2020, for Chinese Patent Application No. 201810844138.8. (with English translation, 12 pages).
STN Registry, RN 2185828-12-8, ACS, Mar. 6, 2018. (52 pages).

AROMATIC HETEROCYCLIC COMPOUND AND ORGANIC LIGHT-EMITTING DISPLAY DEVICE

CROSS-REFERENCE TO RELATED APPLICATIONS

The present disclosure claims priority to Chinese Patent Application No. 201810844138.8, filed on Jul. 27, 2018, the content of which is incorporated herein by reference in its entirety.

TECHNICAL FIELD

The present disclosure relates to the technical field of organic electroluminescent materials, and in particular to a material having thermally activated delayed fluorescence (TADF) properties and its use in an organic optoelectronic device.

BACKGROUND

With the rapid development of electronic display technology, Organic Light-emitting Diodes (OLEDs) are widely used in various display devices, and research on light-emitting materials of OLEDs is also more intensive.

Based on the light-emitting mechanism, materials applicable in a light-emitting layer of the OLED can be mainly divided into four types:

(1) fluorescent materials; (2) phosphorescent materials; (3) triplet-triplet annihilation (TTA) materials; (4) thermally activated delayed fluorescence (TADF) materials.

As regards the fluorescent materials, according to spin-statistics, a ratio of singlet excitons to triplet excitons is 1:3, and thus the maximum internal quantum yield of fluorescent materials does not exceed 25%. According to the Lambertian luminescence mode, the light extraction efficiency is about 20%, and thus an External Quantum Efficiency (EQE) of the OLED device based on the fluorescent material does not exceed 5%.

For the phosphorescent materials, due to its heavy atom effect, the phosphorescent materials can intensify intersystem in the molecule through spin-coupling, and 75% of triplet excitons can be directly utilized to achieve emission at room temperature with both S1 and T1 states participating therein. With the theoretical maximum internal quantum yield reaching 100%. According to the Lambertian luminescence mode, the light extraction efficiency is about 20%, thus the EQE of the OLED device based on the phosphorescent materials can reach 20%. However, the phosphorescent materials are basically complexes of a heavy metal, such as Ir, Pt, Os, Re, Ru, etc., and are characterized by high production cost, which is not conducive to large-scale production. Under the condition of high electric current density, the phosphorescent materials show a phenomenon of dramatic efficiency roll-off, and the stability of phosphorescent devices is not good.

As regards TAA materials, two adjacent triplet excitons are combined to form a singlet excited state molecule with higher energy level and a ground state molecule. However, since the two triplet excitons merely produce one singlet state exciton, the theoretical maximum internal quantum yield can only reach 62.5%. In order to prevent the substantial decrease in efficiency, a concentration of triplet excitons should be regulated during this process.

For the TADF materials, when an energy level difference between the singlet excited state and the triplet excited state is relatively small, a reverse intersystem crossing (RISC) may occur among the molecules, and the excitons are converted from a T1 state to an S1 state by absorbing ambient heat, so that 75% of triplet excitons and 25% of singlet excitons can be utilized at the same time. In this way, the theoretical maximum internal quantum yield can reach 100%. The TADF materials are mainly organic compounds without rare metal element, so that the production cost is relatively low. The TADF materials can be chemically modified by various methods. However, there are few TADF materials that have been discovered so far. Accordingly, there is a pressing need to develop new TADF materials applicable in OLED devices.

SUMMARY

The present disclosure provides an electroluminescent aromatic heterocyclic compound having the TADF property.

In an embodiment, the aromatic heterocyclic compound having the TADF property has a chemical structure represented by the formula (I):

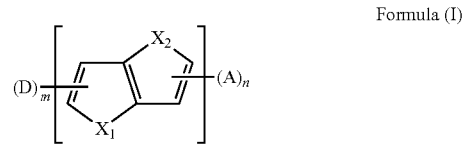

Formula (I)

in which $X_1$ and $X_2$ are independently selected from S and O;

D is a chemical group acting as an electron donor,

A is a chemical group acting as an electron acceptor;

m is a number of the electron donors D, the m electron donors D are the same or different from one another;

n is a number of the electron acceptors A, the n electron acceptors are the same or different from one another; and m and n are integers independently selected from 1 and 2.

DESCRIPTION OF EMBODIMENTS

Figure 1:
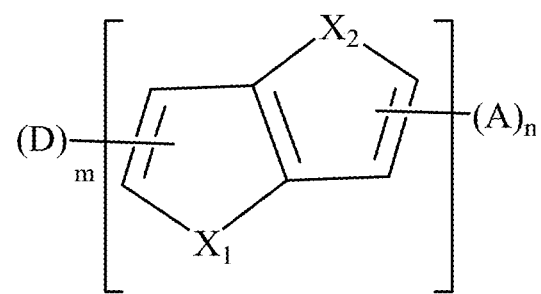
FIG. 1 is a general formula of a compound having a TADF property, according to an embodiment of the present disclosure.

The present disclosure is further described by the following examples, which are merely intended to illustrate the claimed subject matter, and the claimed subject matter is not limited to the following examples. Modifications or equivalents to the technical solutions of the present disclosure should be included within the scope of the present disclosure.

In a first aspect, the present disclosure provides an aromatic heterocyclic compound, having a structure represented by Formula (I):

Formula (I)

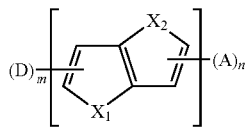

in which $X_1$ and $X_2$ are independently selected from S and O;

D is a chemical group acting as an electron donor,

A is a chemical group acting as an electron acceptor;

m is a number of the electron donors D, wherein m electron donors D are the same or different from one another;

n is a number of the electron acceptors A, wherein n electron acceptors are the same or different from one another; and m and n are integers independently selected from 1 and 2.

In an embodiment according to the present disclosure, the fused aromatic heterocyclic rings in the Formula (I) is a linking unit for linking the electron donor D and the electron acceptor A, so as to form a compound having a TADF property.

In an embodiment according to the present disclosure, any one of the m electron donors D is any one of following chemical groups:

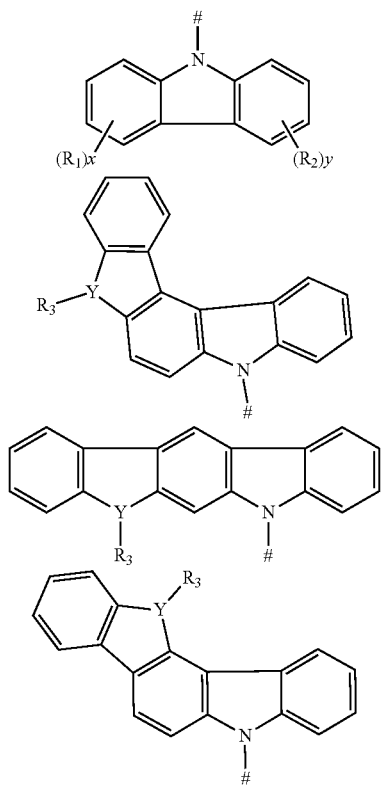

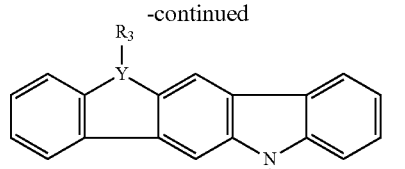

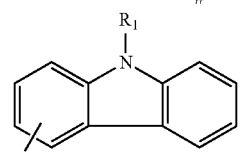

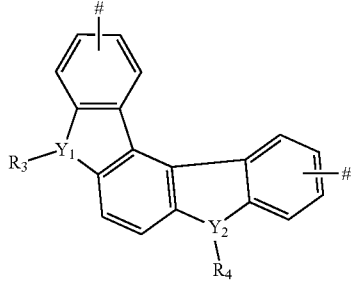

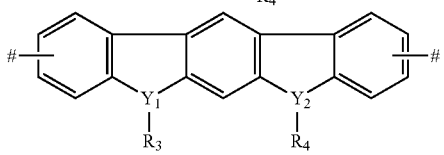

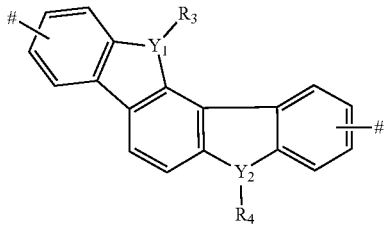

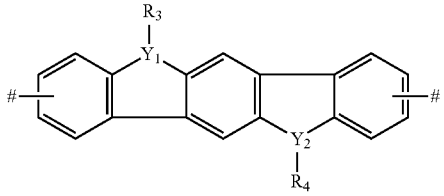

in which Y, $Y_1$ and $Y_2$ are independently selected from the group consisting of carbon, nitrogen, oxygen, sulfur and silicon;

x and y are integers independently selected from 0, 1, 2 and 3;

indicates a bonding position;

when Y is oxygen or sulfur, $R_3$ is absent;

when $Y_1$ is oxygen or sulfur, $R_3$ is absent;

when $Y_2$ is oxygen or sulfur, $R_4$ is absent; and $R_1$, $R_2$, $R_3$ and $R_4$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C3-C40 azine group and its derivative groups, and groups represented by formula (21):

Formula (21)

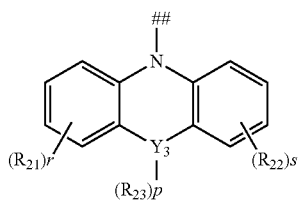

in which $Y_3$ is selected from the group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and indicates a bonding position.

In an embodiment, any one of the m electron donors D is any one of following chemical groups:

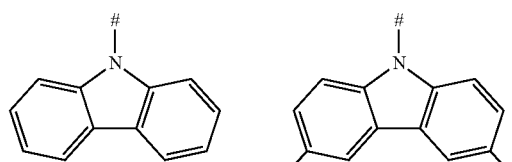

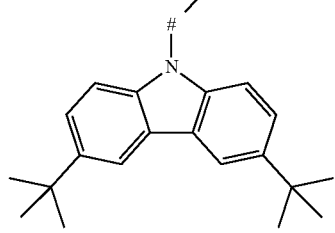

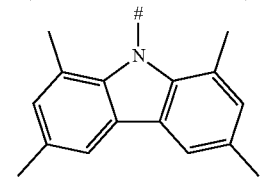

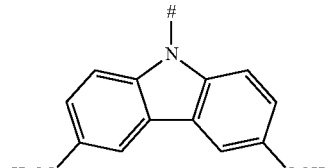

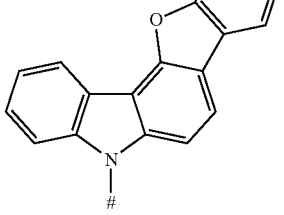

-continued

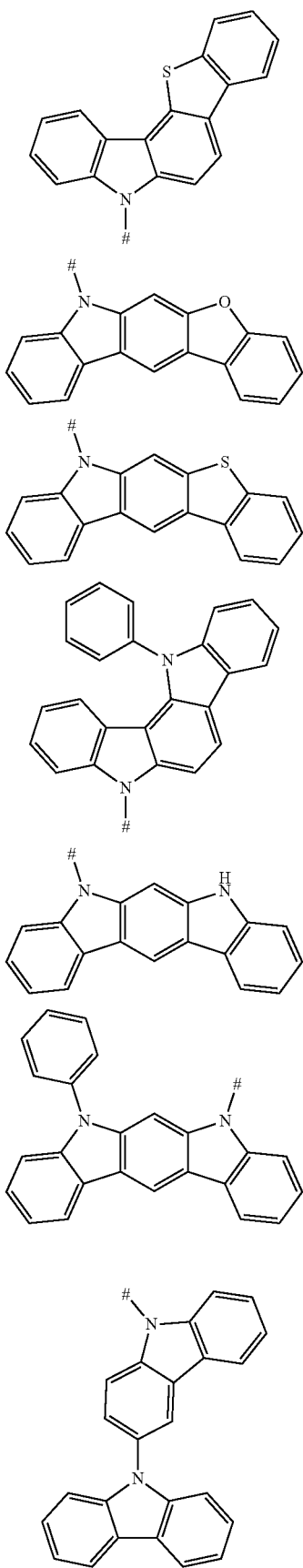

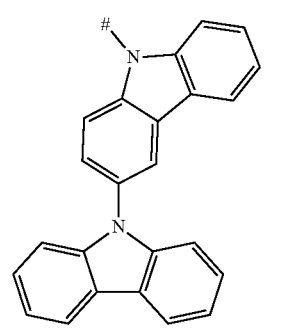

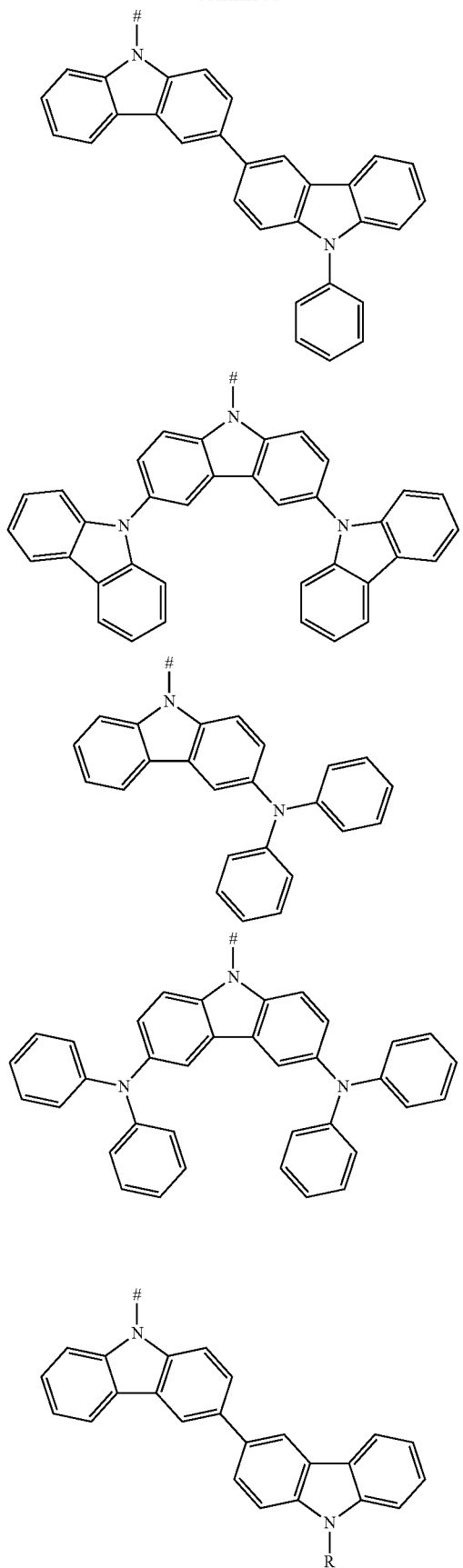

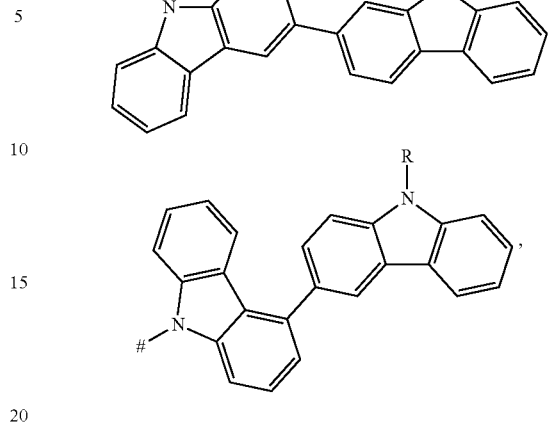

in which R is selected from the group consisting of C1-C20 alkyl, C1-C20 alkoxy, C2-C20 alkenyl, C2-C20 alkynyl, C6-C40 aryl, and C4-C40 heteroaryl; and indicates a bonding position.

In an embodiment the electron donor is a carbazoyl or derivative thereof. Such carbazoyl-based electron donors provide one or more of the following advantages: (1) the raw material is inexpensive; (2) it is easy to modify the molecular properties without changing a main backbone of molecule; (3) functional modifications can be easily made on the nitrogen atom; (4) multiple bonding positions on the carbazole group can be bonded to other molecular structures; (5) good heat stability and chemical stability; (6) high triplet energy level; and (7) excellent electron donating ability and luminescence performance, and (8) excellent hole transmission property.

In an embodiment, any one of the m electron donors D is any one of following chemical groups:

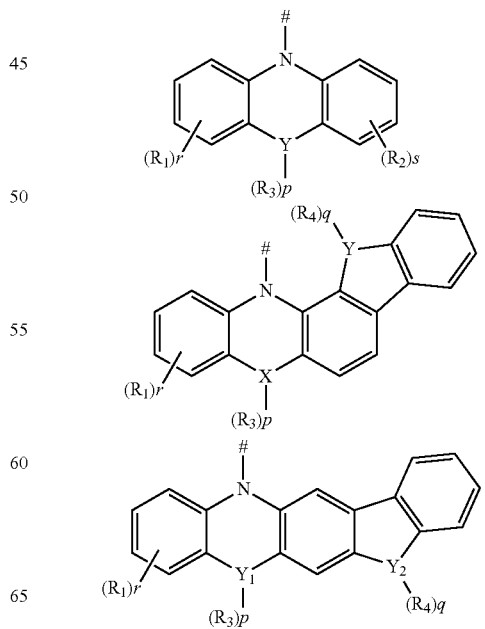

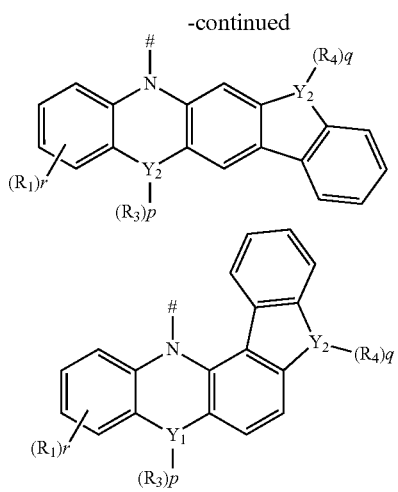

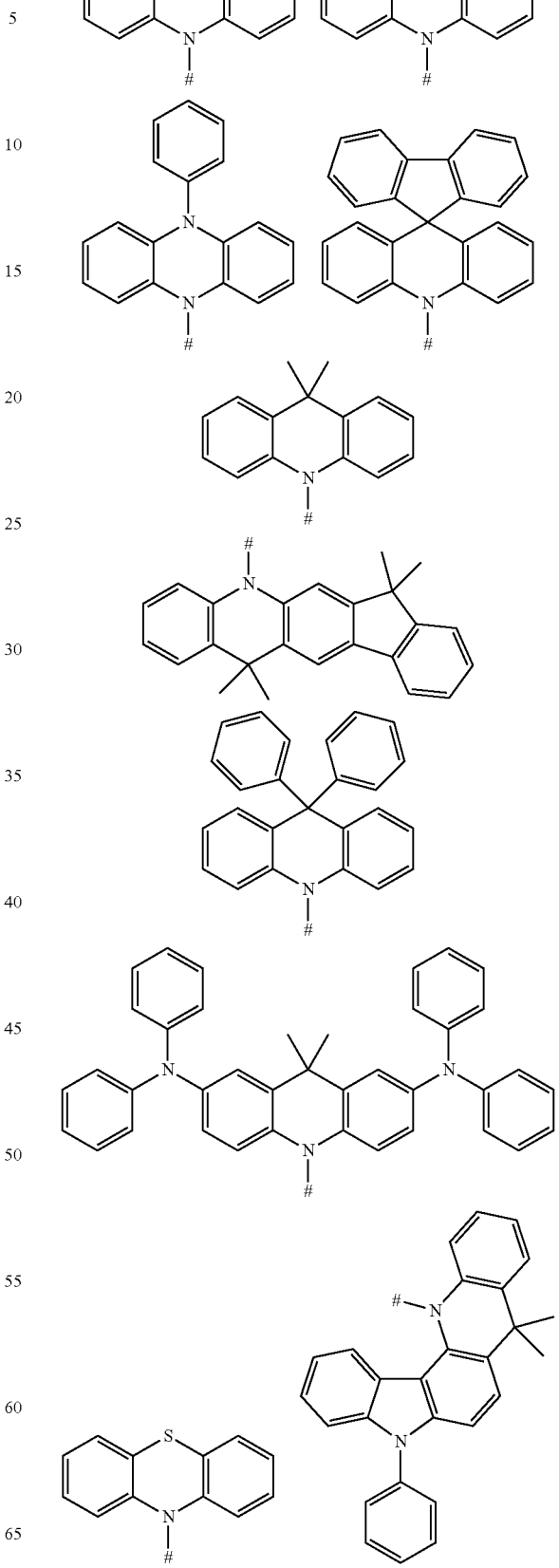

in which Y, $Y_1$ and $Y_2$ are independently selected from the group consisting of carbon, nitrogen, oxygen, sulfur, and silicon;

indicates a bonding position;

r and s are integers independently selected from 0, 1, 2 and 3, and p and q are integers independently selected from 0, 1 and 2;

when Y is oxygen or sulfur, p=0 or q=0;

when Y is nitrogen, p and q are independently 0 or 1;

when Y is carbon or silicon, p and q are independently selected from 0, 1 and 2; and $R_1$, $R_2$, $R_3$ and $R_4$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C13-C40 acridinyl and its derivative groups, substituted or unsubstituted C3-C40 azine group and its derivative groups, and groups represented by Formula (21):

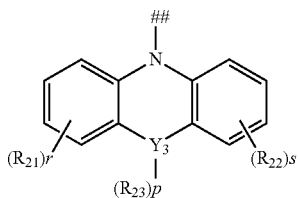

in which $Y_3$ is selected from a group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and indicates a bonding position.

In an embodiment, any one of the m electron donors D is any one of following chemical groups:

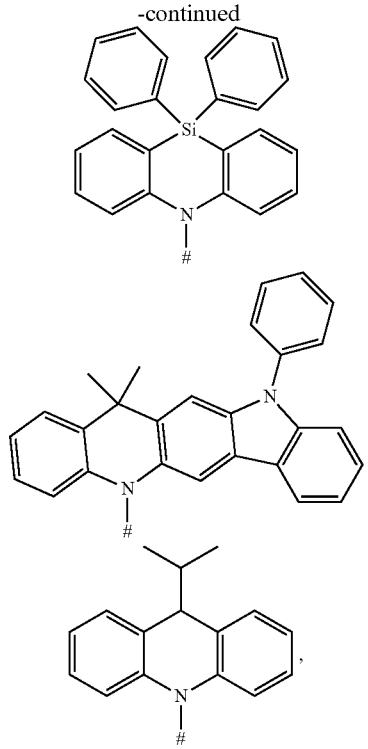

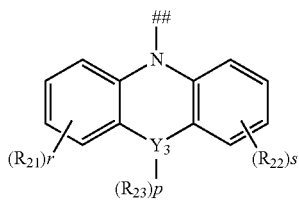

Formula (21)

in which # indicates a bonding position.

In an embodiment, the electron donor D is acridinyl or a derivative thereof. Such acridinyl-based electron donors provide one or more of the following advantages: (1) very strong electron donating ability, shorter retarded fluorescence lifetime; (2) better separation of HOMO from LUMO; (3) rigid molecular structure, which can effectively reduce a non-radiative decay of the excited state; (4) the rigid molecular structure also can inhibit free intramolecular rotation and vibration, which is conductive to improving a monochromaticity of the material and reducing a Full Width Half Maximum (FWHM) of the material; and (5) high triplet energy level.

In an embodiment, any one of the m electron donors D is any one of following chemical groups:

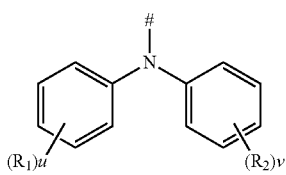

in which # indicates a bonding position;

u and v are integers independently selected from 0, 1, 2 and 3;

$R_1$ and $R_2$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C3-C40 azine group and its derivative groups, and groups represented by Formula (21):

in which $Y_3$ is selected from the group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and indicates a bonding position.

In an embodiment, any one of the m electron donors D is any one of following chemical groups:

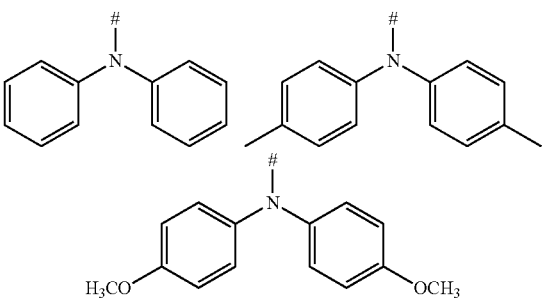

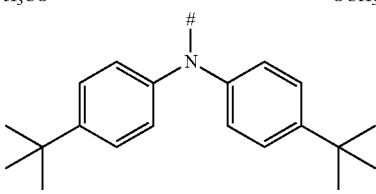

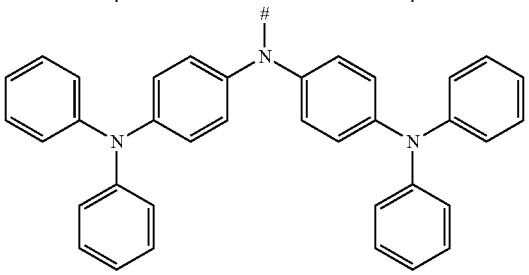

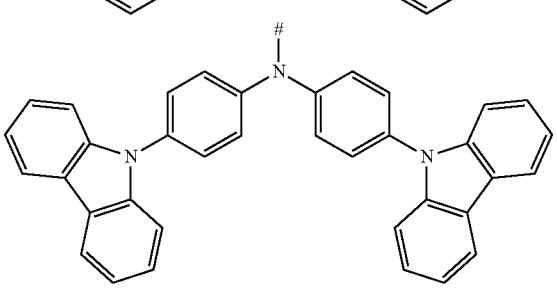

-continued

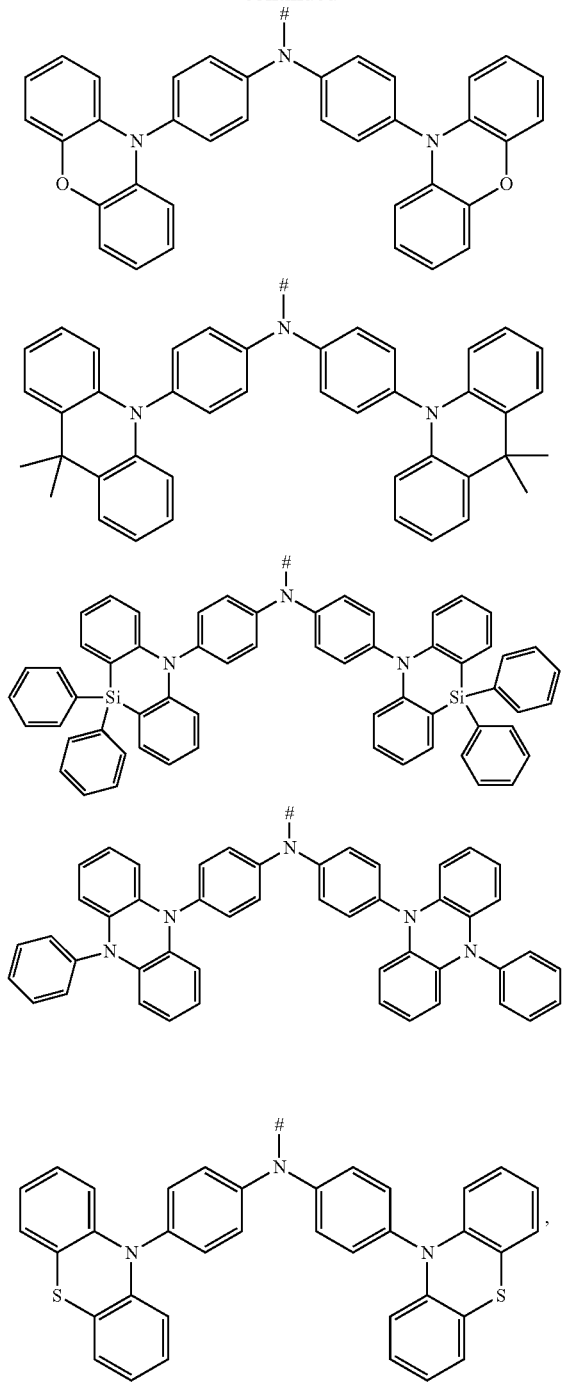

in which # indicates a bonding position.

In an embodiment, the electron donor D is a diphenylamino or derivative thereof. Such dephenylamino-based electron donors provide one or more of the following advantages: (1) moderate electron donating ability; and (2) good heat stability and chemical stability, (3) wide sources of raw material, (4) low cost, (5) easy to be chemically modifiable, and (6) effective spatial separation of HOMO from LUMO.

In an embodiment, any one of the m electron donors D is any one of following chemical groups:

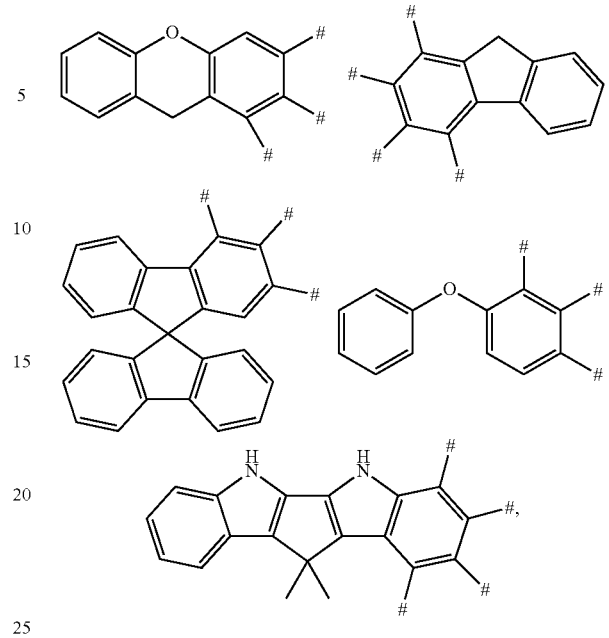

in which # indicates a bonding position. These compounds also have good electron donating property.

In an embodiment, any one of the n electron acceptors A is selected from the group consisting of a nitrogenous heterocyclic substituent, a cyano-containing substituent, a triaryl boron substituent, a benzophenone substituent, an aromatic heterocyclic ketone substituent, and a sulfone substituent.

In an embodiment, the nitrogenous heterocyclic substituent is any one of following chemical groups:

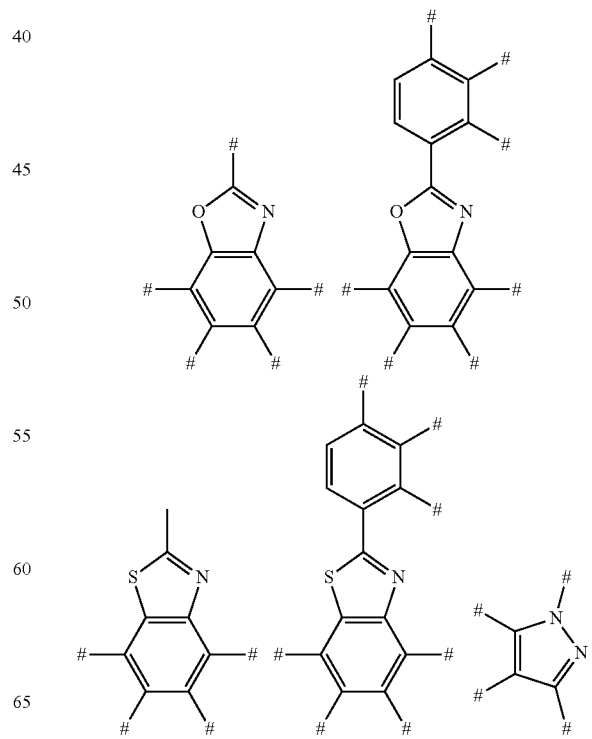

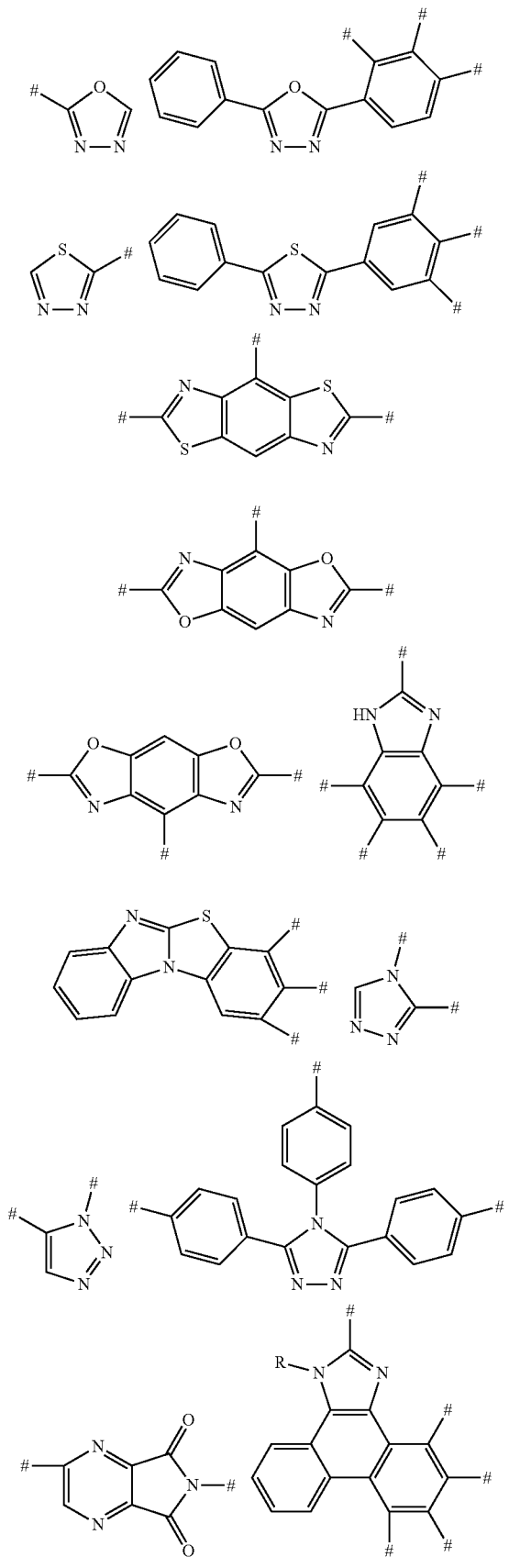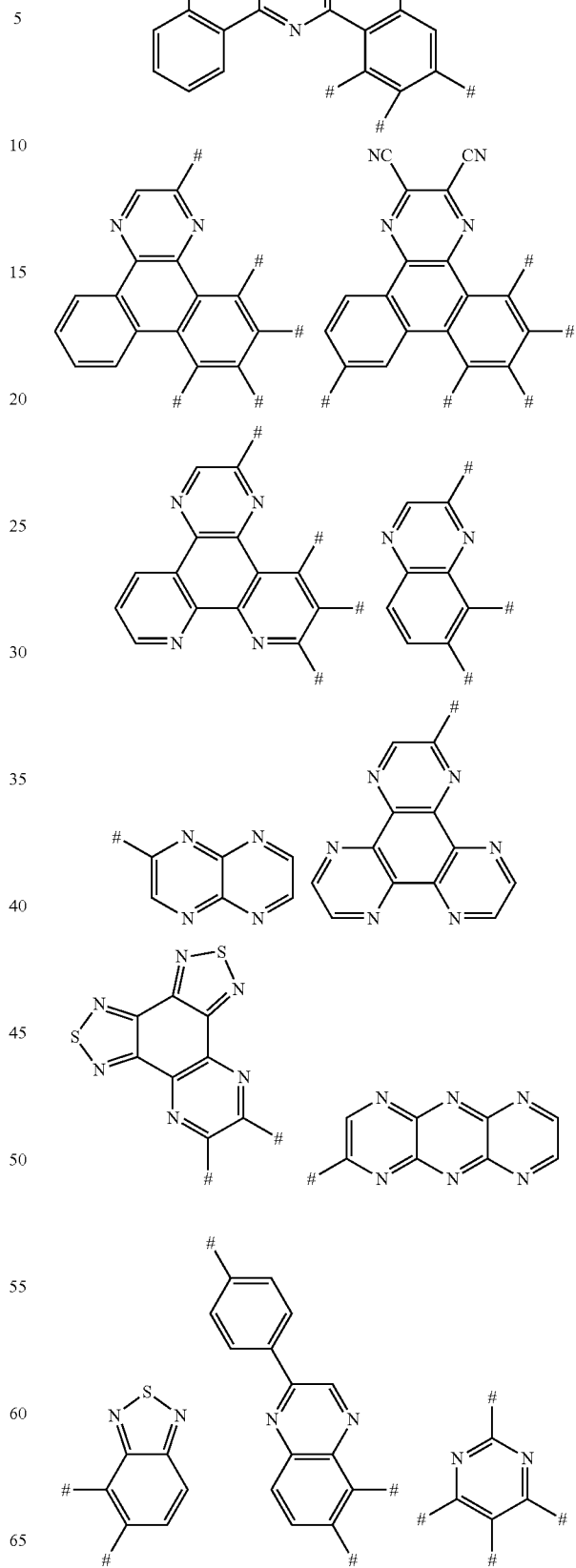

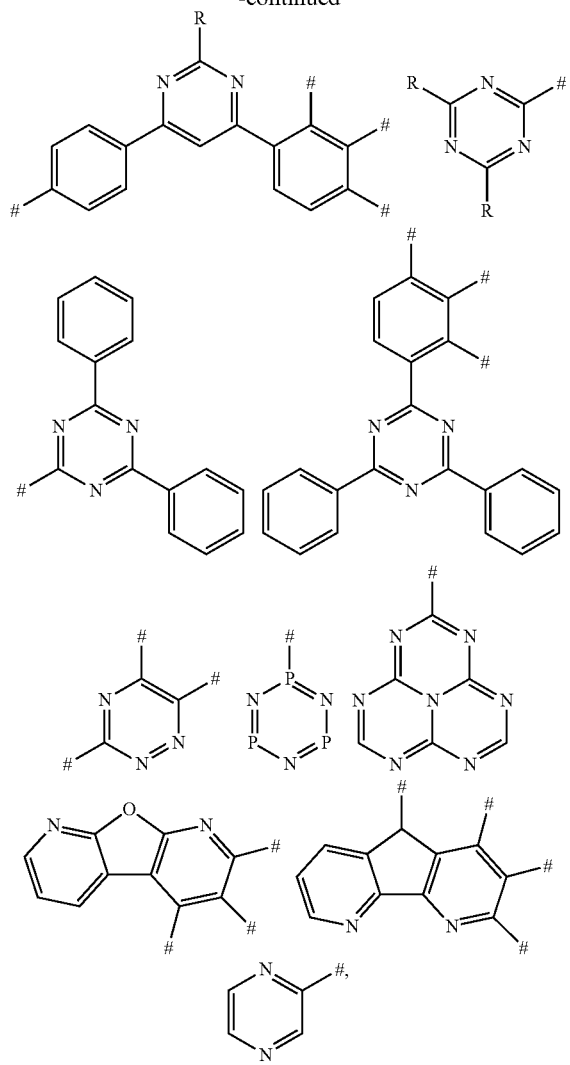

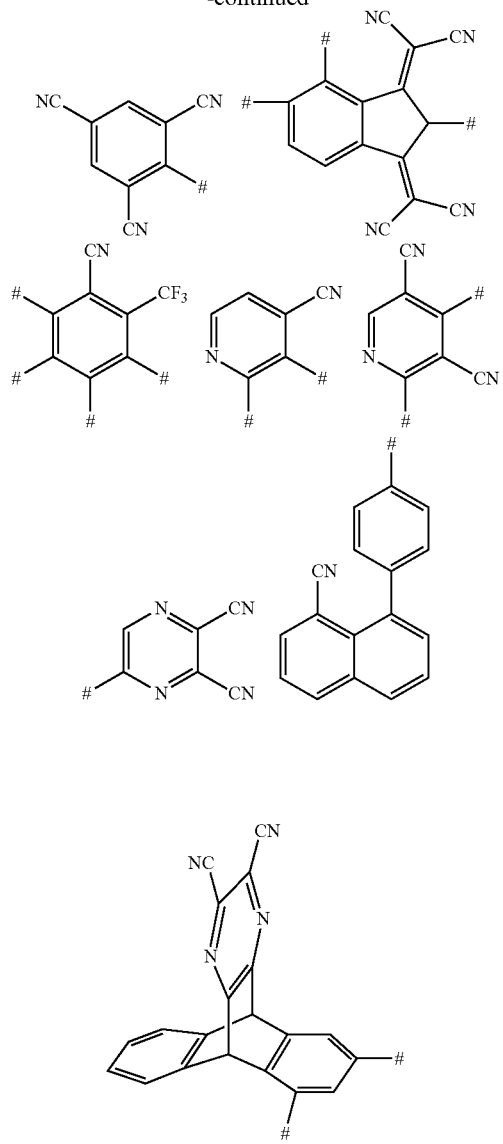

in which # indicates a bonding position; and

R is selected from the group consisting of hydrogen, C1-C20 alkyl, C1-C20 alkoxy, C4-C8 cycloalkyl, C6-C40 aryl, and C4-C40 heteroaryl.

In an embodiment, the cyano-containing substituent is any one of following chemical groups:

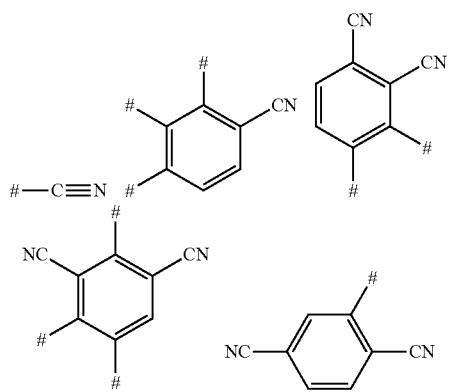

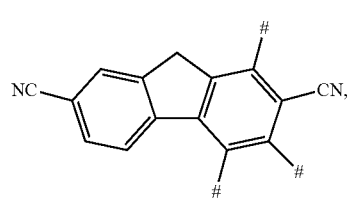

in which # indicates a bonding position.

In this embodiment of the aromatic heterocyclic compound, the cyano-containing substituent has a very strong electron-withdrawing ability. In this way, a non-radiative transition can be effectively suppressed, thereby forming a D-A type TADF molecule with low $\Delta E_{ST}$ and high radiation transition rate constant kr.

In an embodiment, the triaryl boron substituent is any one of following chemical groups:

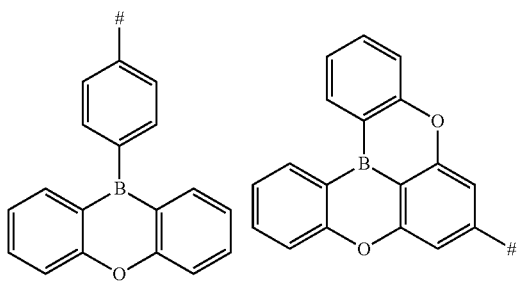
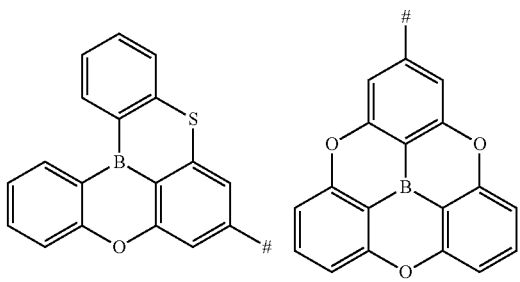
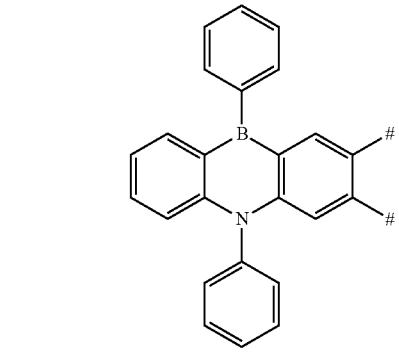

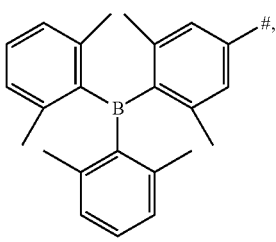

in which # indicates a bonding position.

In this embodiment of the aromatic heterocyclic compound, due to an empty p orbital of the boron atom, when the aromatic ring is bonded to the boron atom, a conjugate plane can be provided, and the substituent on the aromatic ring protects the boron atom from being affected by oxygen and water. In this way, the group has better optical properties and can be used to synthesize triaryl derivatives. The obtained triaryl boron substituents can be used to form D-A type TADF materials.

In an embodiment, the benzophenone substituent and the heterocyclic ketone substituent each is any one of following groups:

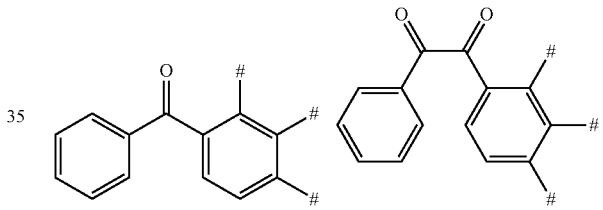
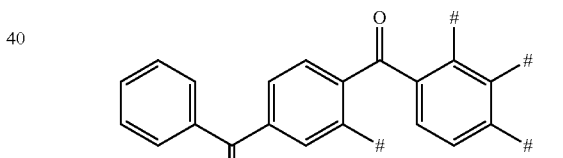
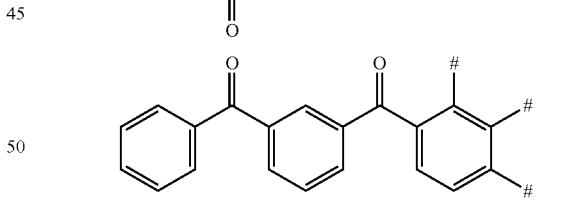
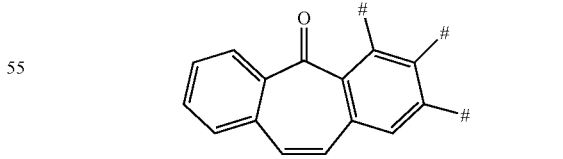
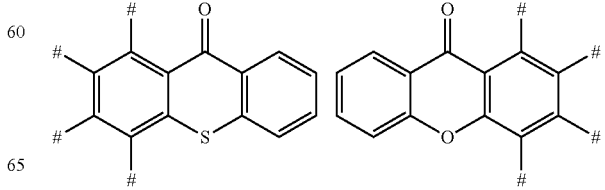

-continued

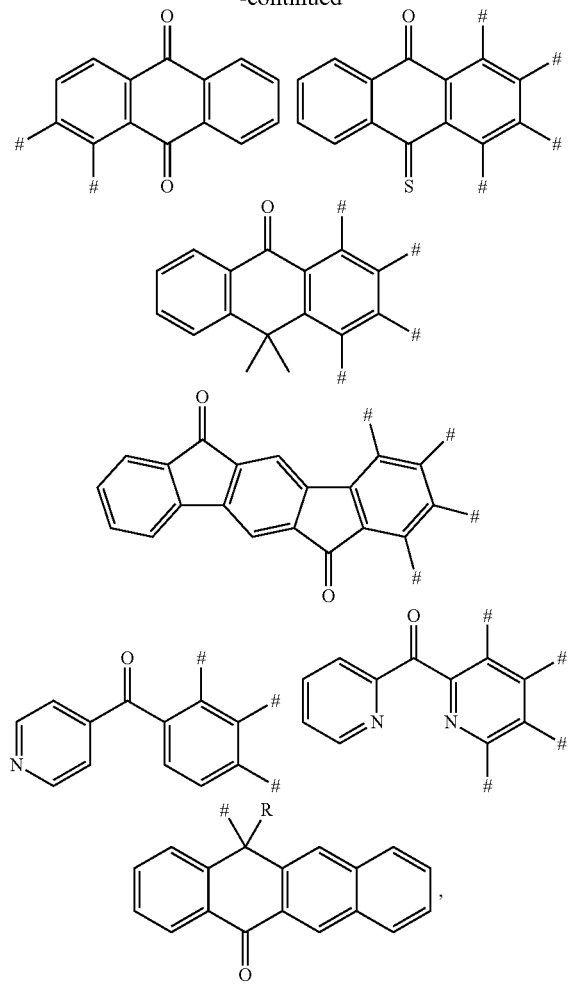

in which # indicates a bonding position; and

R is selected from the group consisting of C1-C20 alkyl, C1-C20 alkoxy, C2-C20 alkenyl, C2-C20 alkynyl, C4-C8 cycloalkyl, C6-C40 aryl, and C4-C40 heteroaryl.

In an embodiment, the benzophenone substituents or the heterocyclic ketone substituents contain an electron-deficient carbonyl group (C=O). There is a large angle between the carbonyl group and the benzene ring, at least in part because the carbonyl group is an electron acceptor. Therefore, the benzophenone substituents or the heterocyclic ketone substituents are pure organic phosphors with very efficient intersystem crossing (kISC=$10^{11} \cdot s^{-1}$). In this regard, they are very suitable to be used as electron acceptor to form D-A type TADF molecules emitting blue light.

In an embodiment, the sulfone substituent is any one of following groups:

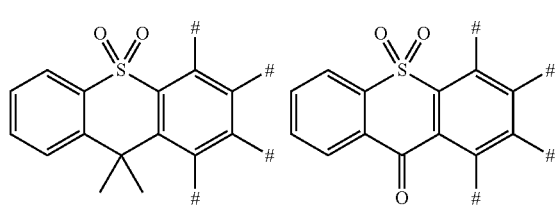

-continued

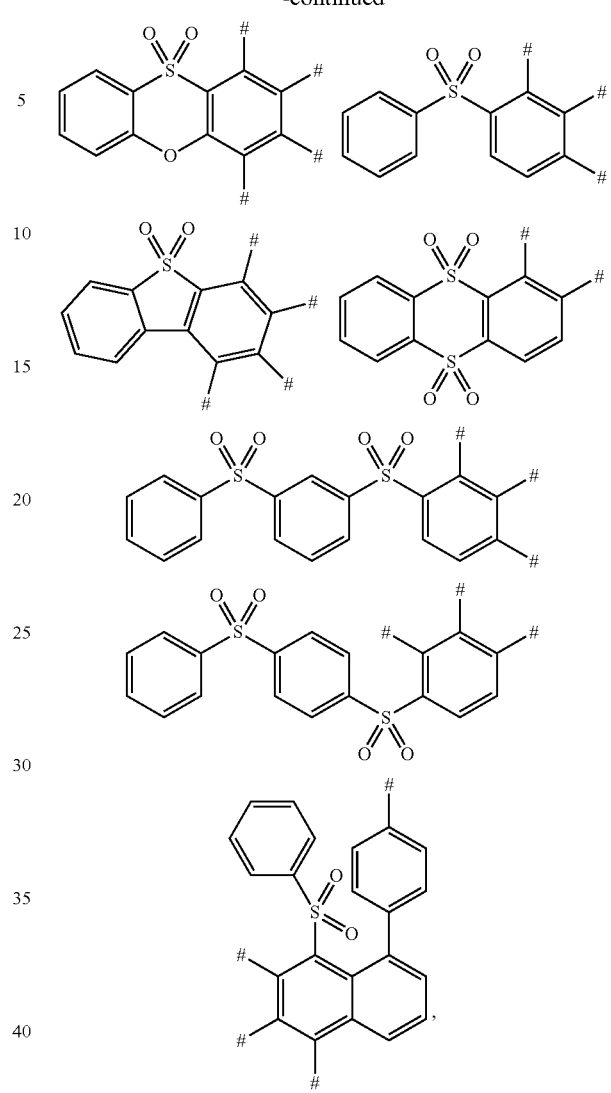

in which # indicates a bonding position.

In this embodiment of the aromatic heterocyclic compound, the sulfone substituent, as an electron acceptor, has good electron-withdrawing ability and has a certain torsion angle at the center of molecular to obtain a lower $\Delta E_{ST}$ value. Therefore, the sulfone substituent can be used as an electron acceptor to form D-A type TADF molecules.

In an embodiment, any one of the n electron acceptors A is any one of following groups:

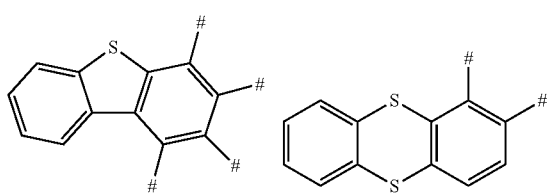

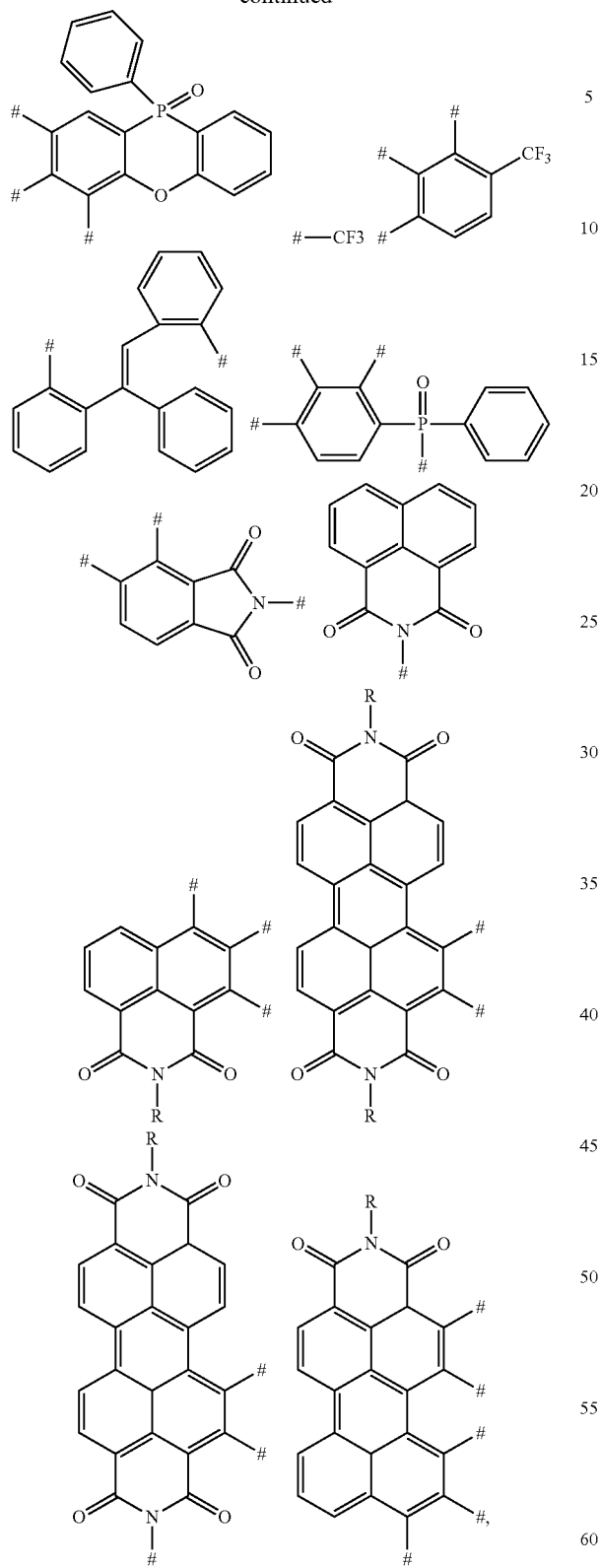
in which # indicates a bonding position;
R is selected from the group consisting of C1-C20 alkyl, C1-C20 alkoxy, C2-C20 alkenyl, C2-C20 alkynyl, C3-C8 cycloalkyl, C6-C40 aryl, and C4-C40 heteroaryl.
According to an embodiment of the present disclosure, the aromatic heterocyclic compound according to the present disclosure is any one of the following compounds:
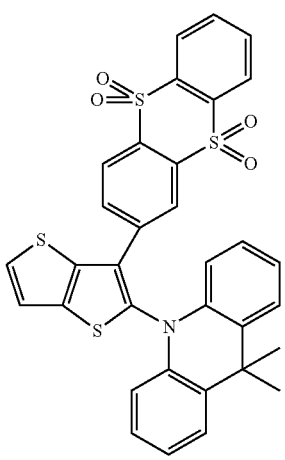
P1
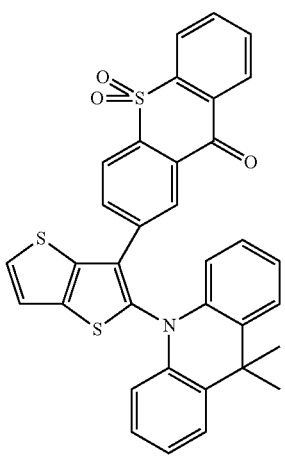
P2
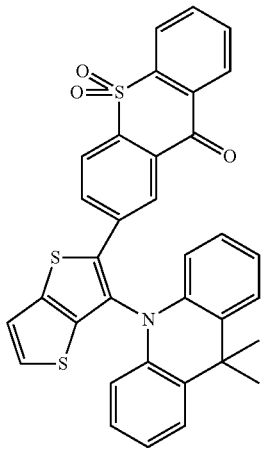
P3

P4
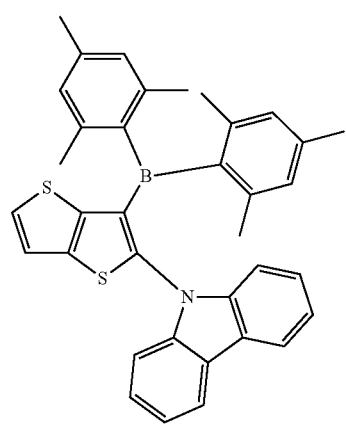
P5
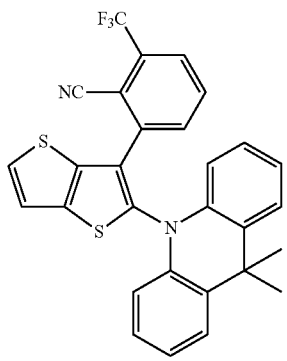
P6
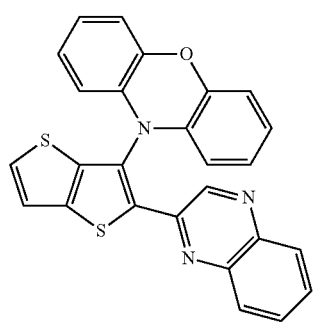
P7
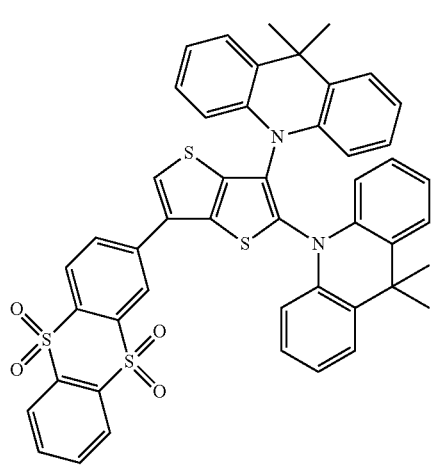
P8
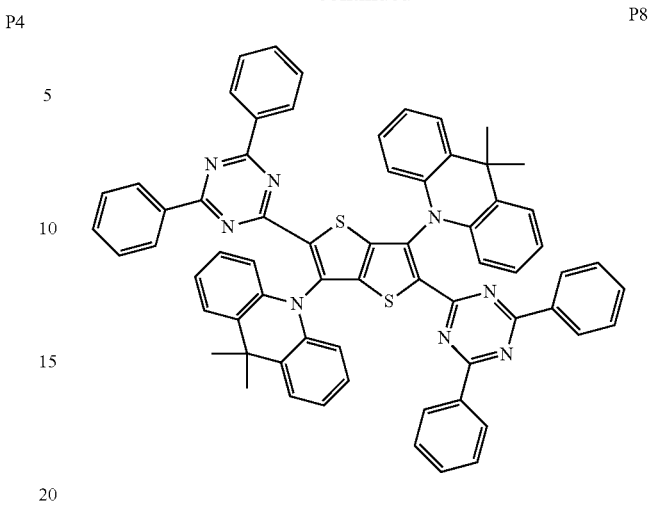
P9
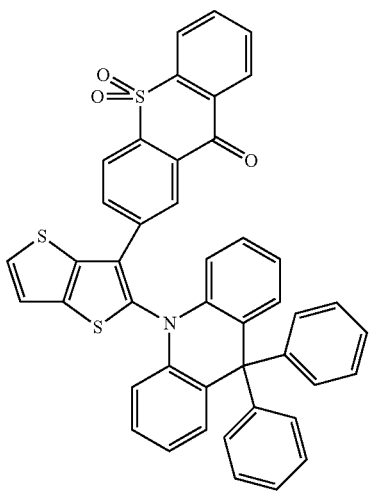
P10
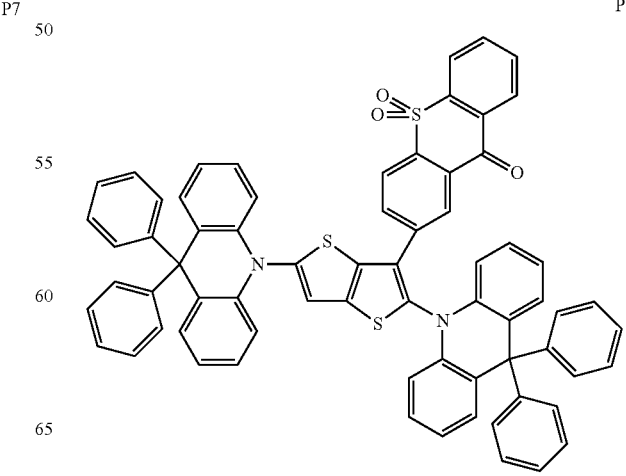

P11
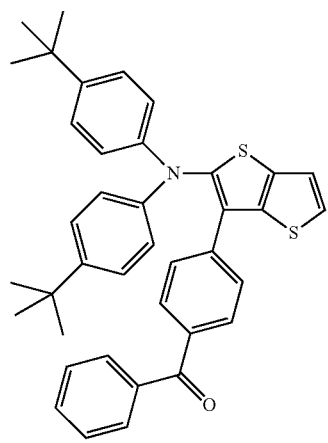
P12
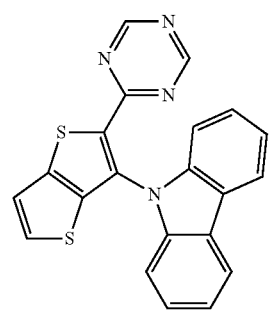
P13
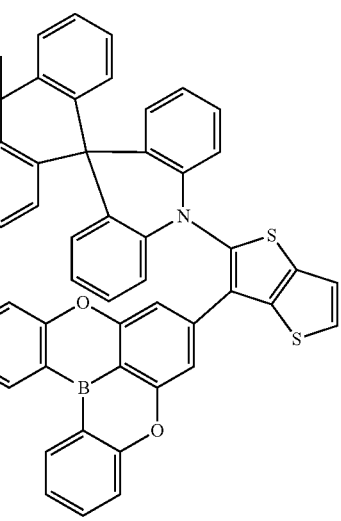
P14
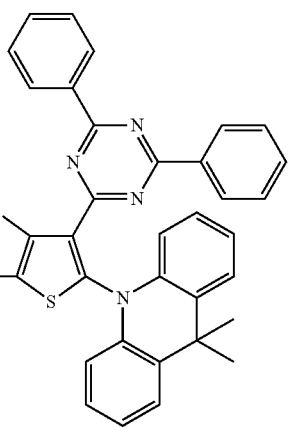
P15
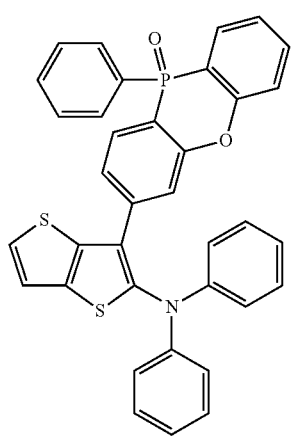
P16
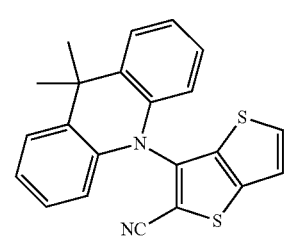
P17
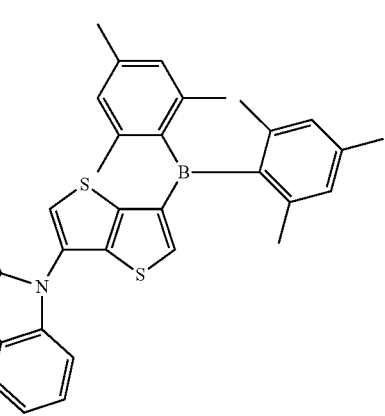

-continued
P18
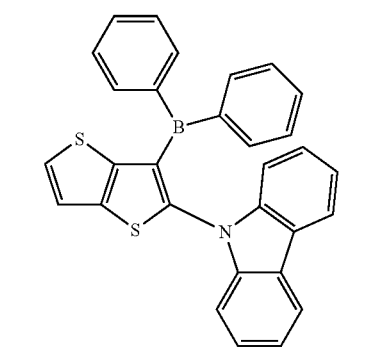
P19
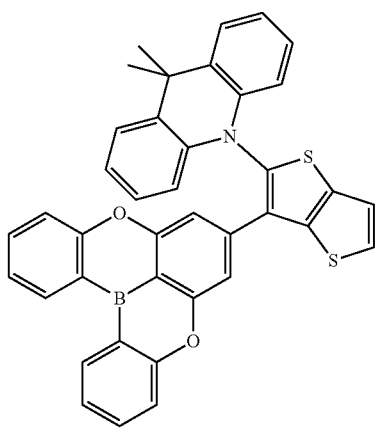
P20
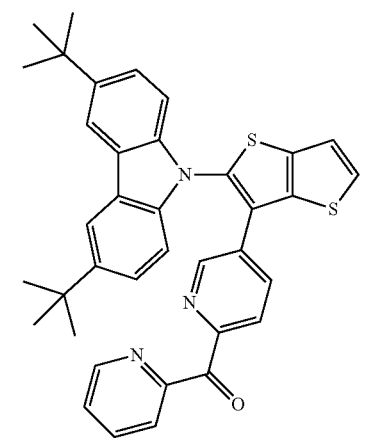
P21
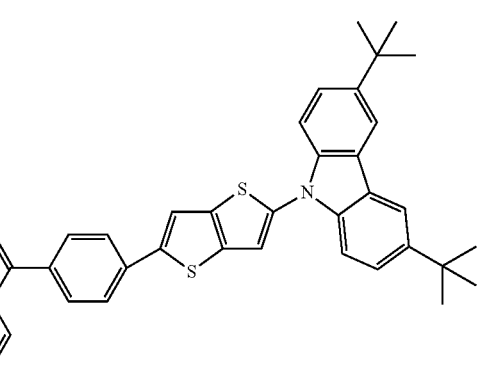
P22
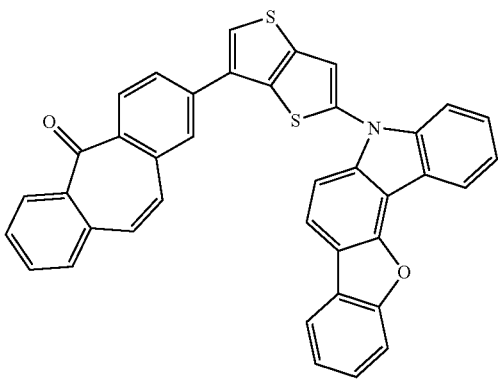
P23
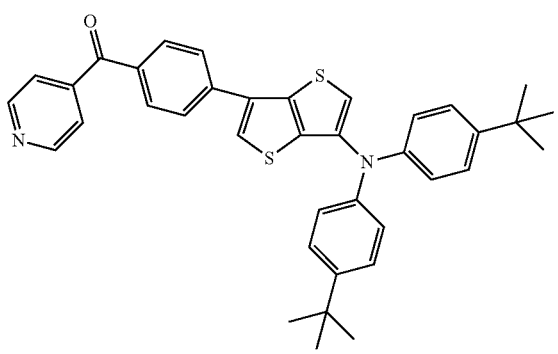
P24
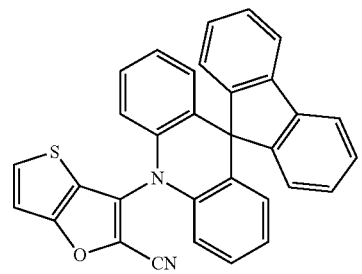
P25
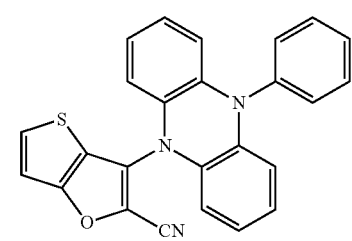

-continued
P26
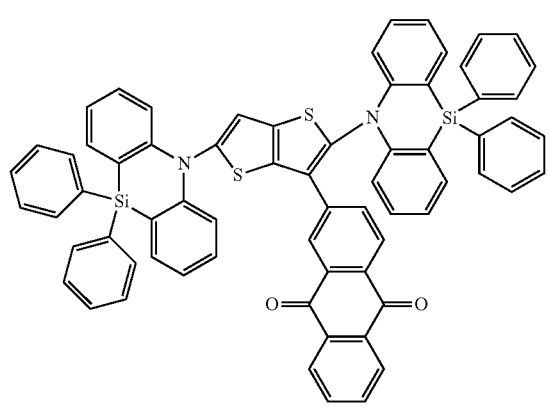
P27
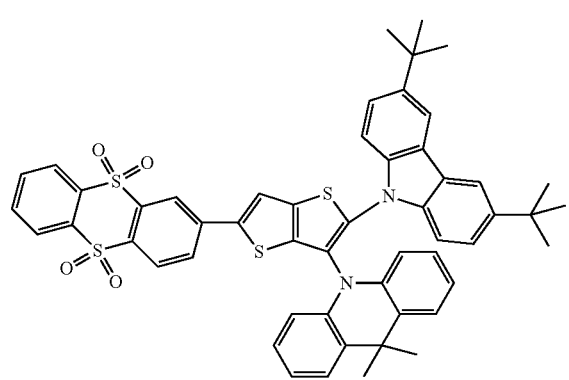
P28
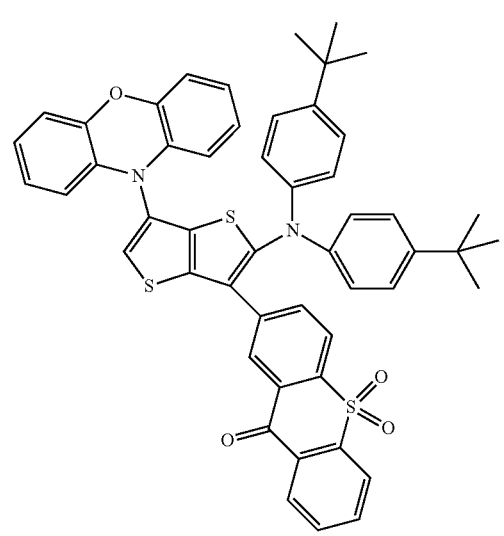
-continued
P29
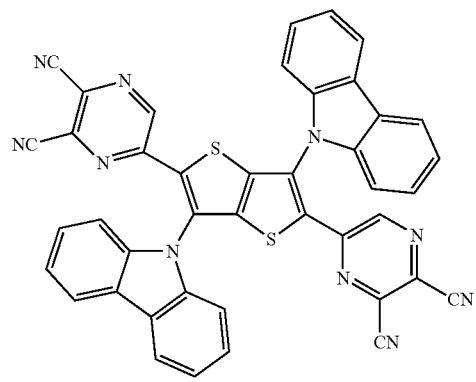
P30
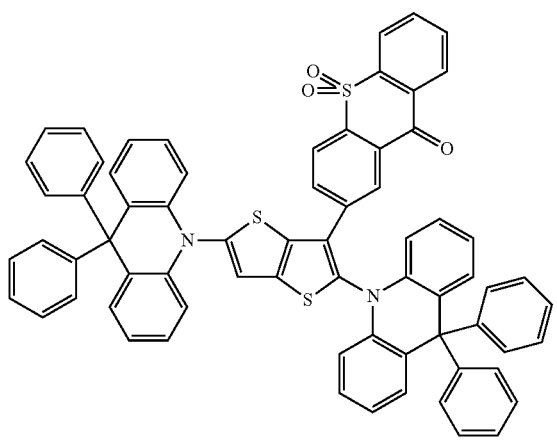
P31
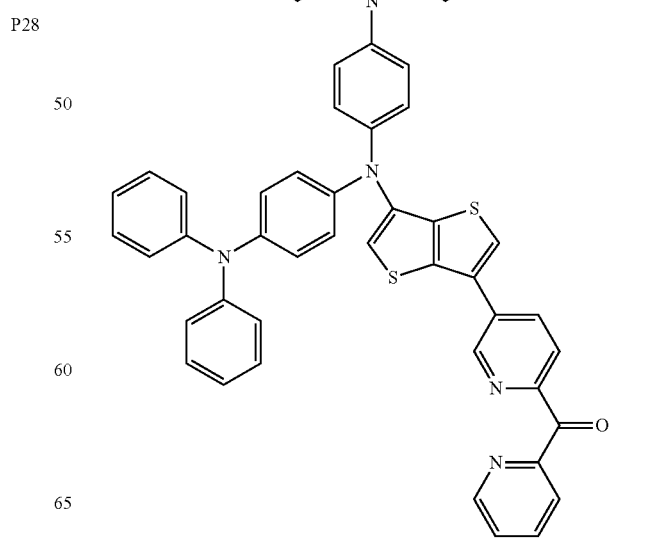

-continued
P32
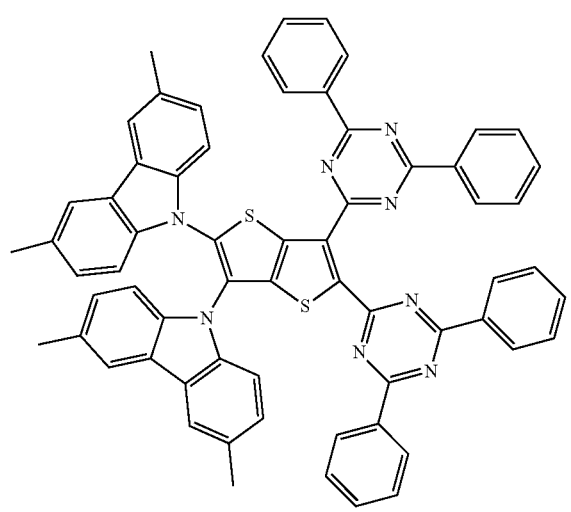
P33
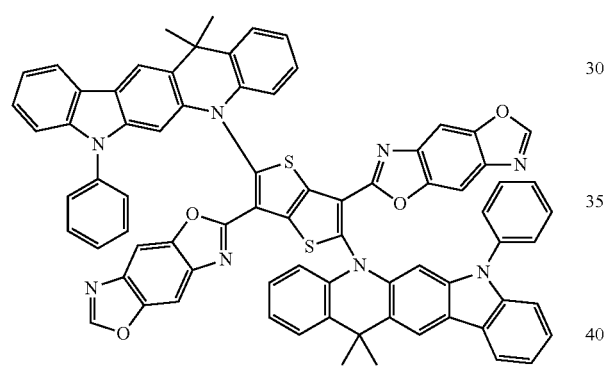
P34
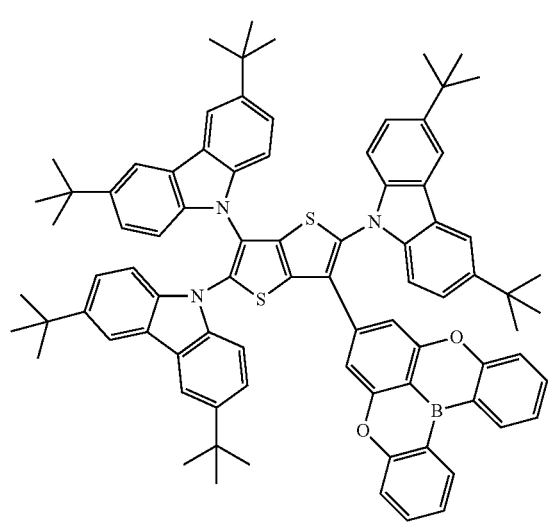
-continued
P35
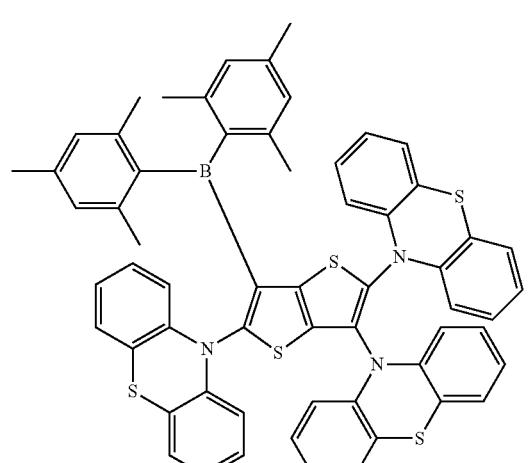
P36
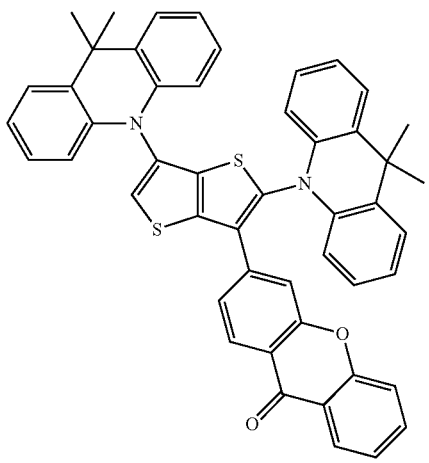
P37
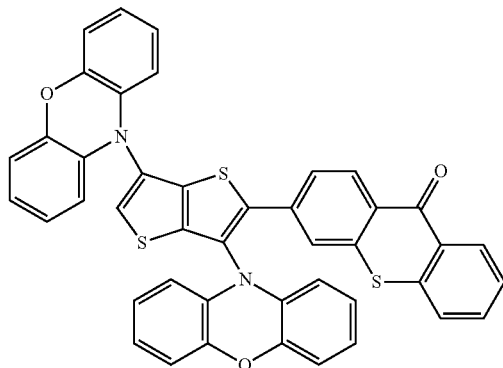

P38

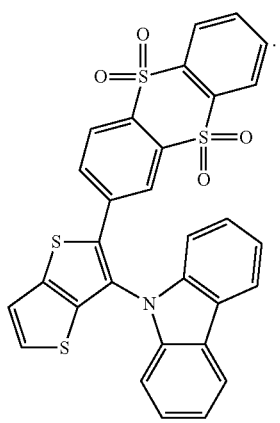

In the aromatic heterocyclic compound according to the present disclosure, it is preferable that the electron donor D and the electron acceptor A are bonded to the Formula (I) in ortho-position. The ortho-position means that the electron donor D and the electron acceptor A both are bonded to two adjacent carbon atom of the compound represented by Formula (I). The ortho-position substitution has the following advantages: (1) more effective separation of HOMO from LUMO; (2) a larger dihedral angle between the electron donor D and electron acceptor A, which leads to a large steric hindrance between the electron donor D and the electron acceptor A and thus results in a smaller $\Delta E_{st}$; and (3) an increased intramolecular spatial restriction, which reduces the positive solvation color change effect, and at the same time, improves excitation purity and reduces the half peak width.

In an embodiment, in the aromatic heterocyclic compound according to the present disclosure, an energy difference $\Delta E_{st}$ between a lowest singlet energy level S1 and a lowest triplet energy level T1 of the compound satisfies the relationship $\Delta E_{st} = E_{S1} - E_{T1} \leq 0.30$ eV. In another embodiment, the energy difference $\Delta E_{st}$ between the lowest singlet energy level S1 and the lowest triplet energy level T1 of the compound satisfies the relationship $\Delta E_{St} = E_{S1} - E_{T1} \leq 0.25$ eV.

Since aromatic heterocyclic compounds according to the present disclosure have the TADF property, they are suitable for use as a light-emitting material of a light-emitting layer in an organic light-emitting display device. Likewise, the compounds of the present disclosure are suitable for use as a host or guest material of a light-emitting layer. Meanwhile, the aromatic heterocyclic compound according to the present disclosure can be used as a red light-emitting material, as a green light-emitting material or as a blue light-emitting material of the light-emitting layer in the organic light-emitting display device. Therefore, the present disclosure also provides uses of the above aromatic heterocyclic compounds in organic light-emitting display devices.

The compounds according to the present disclosure have high luminescence efficiency due to the luminescent mechanism of TADF. When applied to an organic light-emitting display device, the luminescence efficiency thereof also can be improved.

The present disclosure provides a method for preparing the compounds according to several embodiments of the present disclosure. In the following examples, synthesis schemes of compounds P2, P4, P5, P7 and P8 are described as follow.

Example 1

Synthesis of Intermediate Compound S3

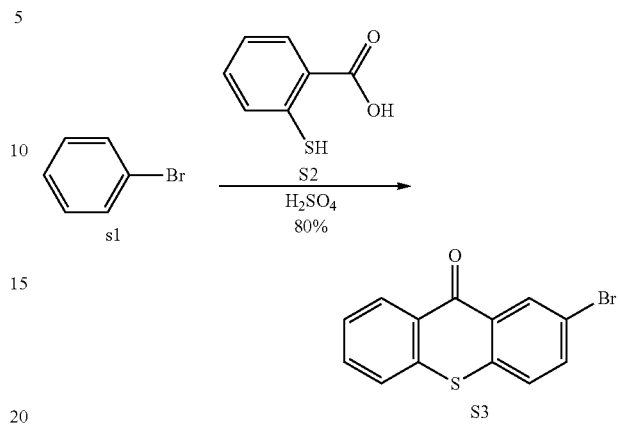

20 ml of concentrated sulfuric acid was added to a 50 ml single-necked flask at room temperature, and then 6 mL of bromobenzene S1 (57 mmol) was added. The mixture was stirred at room temperature for half an hour to obtain a white turbid liquid. Then 1.0 g of thiosalicylic acid S2 (6.5 mmol) was added in portions within half an hour. The obtained mixture was stirred at room temperature for 24 h, then heated at 100° C. for 2-3 h. The mixture was cooled to room temperature, then poured into ice water carefully, and a white solid is obtain by performing a filtration. The white solid was re-dissolved by 20% NaOH solution and the mixture was stirred for 2 hours, following by filtering, washing with water until being pH neutral, and a yellow solid S3 was obtained (5.2 mmol, 80%).

$^1$H NMR (400 MHz, CDCl$_3$, ppm): 7.70-7.90 (s, 2H), 7.40-7.60 (m, 4H), 7.30 (m, 1H). MALDI-TOF MS: m/z calculated for C$_{13}$H$_7$BrOS: 289.9. found: 290.0.

Synthesis of Intermediate Compound S4

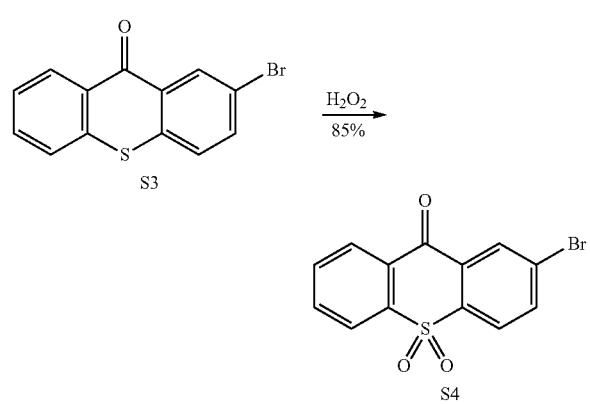

40 mL of glacial acetic acid and 20 mL of dichloromethane, and the intermediate compound S3 (3 mmol), 5 equivalent amount of 30% hydrogen peroxide were add to a 50 mL single-necked flask at room temperature, and then the mixture was stirred at 55-60° C. for 20-24 h. After being cooled to room temperature, the mixture was extracted with dichloromethane. A white solid S4 (2.6 mmol, 85%) is obtained by column chromatography.

MALDI-TOF MS: m/z calculated for C$_{13}$H$_7$BrO$_3$S: 321.9. found: 321.8.

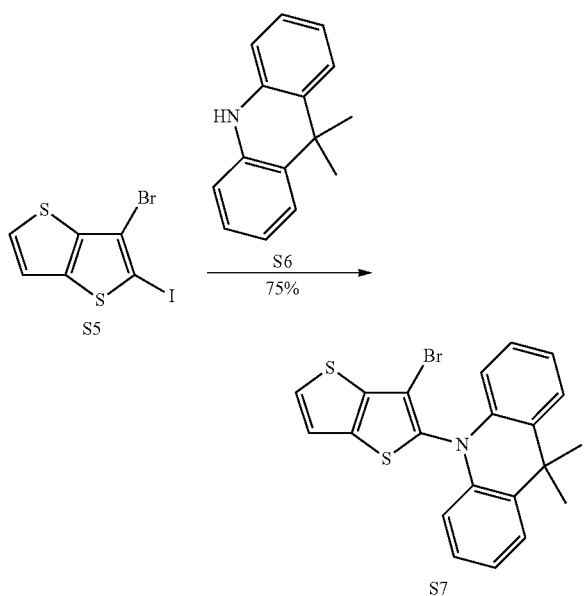

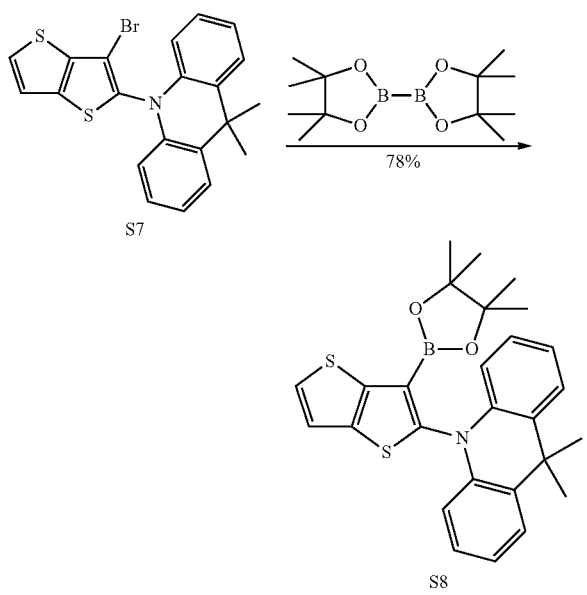

Compound S5 (10 mmol), 9,9-dimethyl-9,10-dihydroacridine (Compound S6, 10.5 mmol), (dibenzylideneacetone) dipalladium (0) (0.05 mmol), sodium t-butoxide (14 mmol) and tri-tert-butylphosphine (0.2 mmol) were added to a 50 mL flask with three necks, and degassing and nitrogen replacement were repeated three times during stirring, then 20 mL of toluene was added through a syringe. The mixture was refluxed for 3 hours under nitrogen stream. After the reaction was completed, the mixture was cooled to room temperature, extracted with dichloromethane after adding water, and washed with saturated brine. After the organic phase was dried with anhydrous sodium sulfate, the solvent was removed by evaporation, and the crude product was purified by column chromatography to obtain an intermediate Compound S7 (7.5 mmol, 75%).

MALDI-TOF MS: m/z calculated for $C_{21}H_{16}BrNS_2$: 425.0. found: 425.4.

Compound S7 (30 mmol), bis(pinacolato)diboron (36 mmol), [1,1'-bis(diphenylphosphino)ferrocene]dichloropalladium(II) (0.3 mmol) and potassium acetate (75 mmol) were added to a 250 mL flask with three necks, and 100 mL of tetrahydrofuran was added through a syringe after repeating degassing and nitrogen replacement three times during stirring. After stirring at a certain rotation speed, the mixture was refluxed at a reaction temperature of 80° C. for 5 hours. After the reaction was completed, the mixture was cooled to room temperature, extracted with diethyl ether after adding 100 ml of water, and the organic phase was dried over anhydrous sodium sulfate. The solvent was removed by evaporation, and the crude product was purified by column chromatography to obtain an intermediate Compound S8 (23.4 mmol, 78%).

MALDI-TOF MS: m/z calculated for $C_{27}H_{28}BNO_2S_2$: 473.2. found: 473.5.

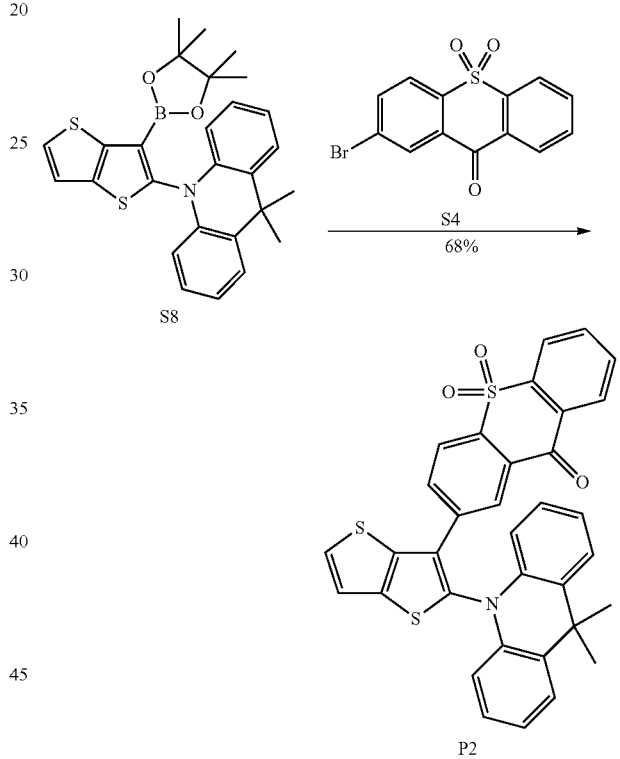

Under protection of nitrogen, Compound S4 (25 mmol), Compound S8 (25 mmol), [Pd$_2$(dba)$_3$].CHCl$_3$ (0.5 mmol) and HP(t-Bu)$_3$.BF$_4$ (1.0 mmol) were weighed and then added to a 250 mL flask with two necks. 100 mL of toluene (N$_2$ was introduced in advance for 15 minutes to remove oxygen) was added into the flask, and then 12 mL of 1M aqueous solution of K$_2$CO$_3$ (N$_2$ was introduced in advance for 15 minutes to remove oxygen) was added dropwise and stirred at room temperature overnight. After the reaction was completed, 100 mL of deionized water and a few drops of 2M HCl were added. The organic phase was collected and dried over anhydrous Na$_2$SO$_4$ after extracting with dichloromethane. The dried solution was filtered, and the solvent was removed using a rotary evaporator to obtain a crude product. The crude product was purified through a silica gel column chromatography to obtain a solid P2 (17.0 mmol, 68%).

MALDI-TOF MS: m/z calculated for $C_{34}H_{23}NO_3S_3$: 589.1. found: 589.6.

Elemental analysis: calculated: C, 69.24; H, 3.93; N, 2.38; O, 8.14; S, 16.31; measured: C, 69.26; H, 3.95; N, 2.36; O, 8.13; S, 16.30.

Example 2

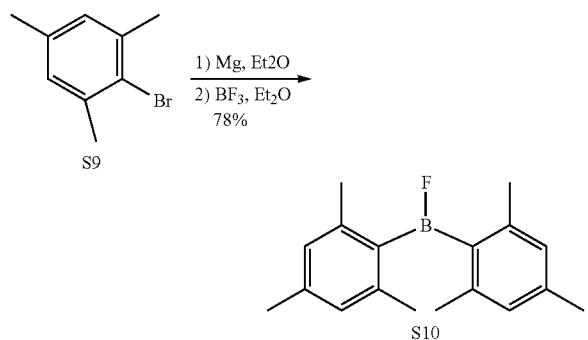

A Mg strip (200 mmol) was weighed and added to a 250 mL flask with three necks, and degassing and nitrogen replacement were repeated three times during stirring. Then Compound S9 (200 mmol) and dry tetrahydrofuran (100 mL) were added thereto. The mixture was heated to react for 2 hours under reflux. The reaction mixture was cooled to 0° C., and a solution of boron trifluoride diethyl etherate (90 mmol) was added dropwise at 0° C. The obtained mixture was refluxed again for 2 hours to obtain a suspension of Compound S10 in THF, and the solvent was removed by evaporation under reduced pressure. The residual was purified by column chromatography, using n-hexane as eluent, and solvent was removed to obtain Compound S24 (156 mmol, 78%).

MALDI-TOF MS: m/z calculated for $C_{18}H_{22}BF$: 268.2. found: 268.1.

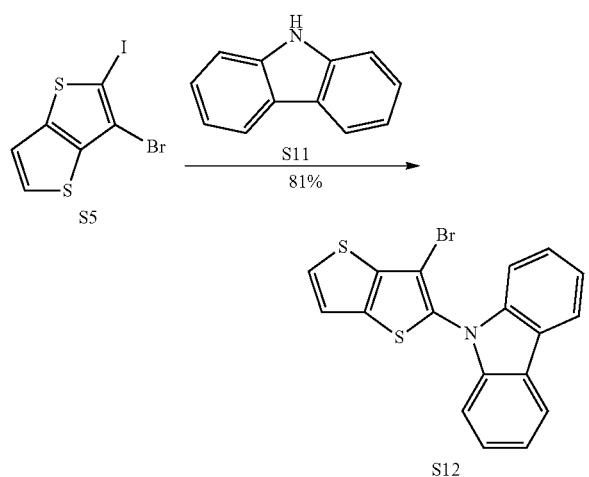

Compound S5 (10 mmol), Compound S11 (10.5 mmol), (dibenzylideneacetone)dipalladium(0) (0.05 mmol), sodium t-butoxide (14 mmol) and tri-tert-butylphosphine (0.2 mmol) were added to a 50 mL flask with three necks, and 20 mL of toluene was added through a syringe after repeating degassing and nitrogen replacement three times during stirring. The mixture was refluxed for 3 hours under nitrogen stream. After the reaction was completed, the reaction mixture was cooled to room temperature, extracted with dichloromethane after adding water, and washed with saturated brine. After the organic layer was dried with anhydrous sodium sulfate, the solvent was removed by evaporation. The obtained crude product was purified by column chromatography to obtain an intermediate Compound S12 (8.1 mmol, 81%).

MALDI-TOF MS: m/z calculated for $C_{18}H_{10}BrNS_2$: 382.9. found: 383.3.

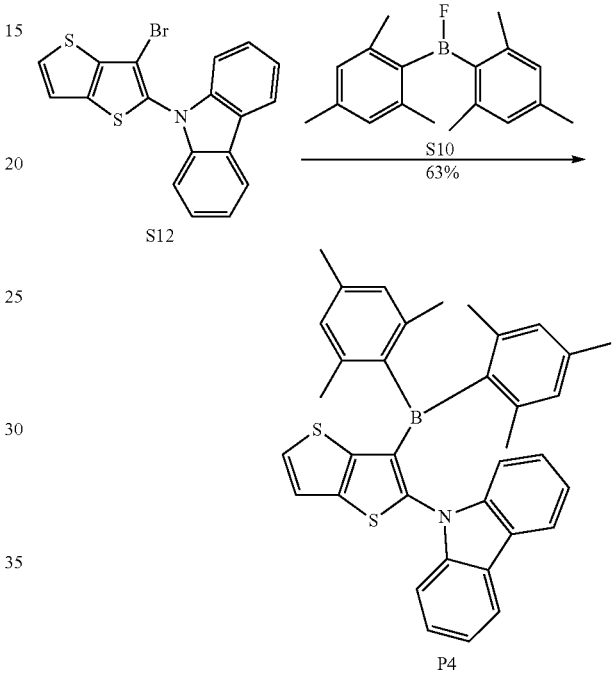

Compound S12 (10 mmol) was weighed and added to a 100 mL flask with two necks, 40 mL of dry ethyl ether was added to dissolve Compound S12 after rapidly repeating degassing and nitrogen replacement 3 times during stirring, and n-BuLi (10.5 mmol) solution was added at −78° C. dropwise and the mixture was stirred for 15 min. The mixture was warmed slowly to room temperature and stirred for 1 h, and then cooled again to −78° C. A solution of Compound S10 in diethyl ether (10.2 mmol in 25 mL) was added dropwise. The mixture was stirred for 30 min, slowly warmed to room temperature and allowed to react overnight. A crude product was obtained after removing the volatile solvent by evaporation under reduced pressure, and washed with methanol (5×10 mL), and finally purified by column chromatography to obtained Compound P4 (6.3 mmol, 63%).

MALDI-TOF MS: m/z calculated for $C_{36}H_{32}BNS_2$: 553.2. found: 553.4.

Elemental analysis: calculated: C, 78.11; H, 5.83; B, 1.95; N, 2.53; S, 11.58. found: C, 78.14; H, 5.85; B, 1.94; N, 2.51; S, 11.56.

Example 3

Compound P5 was synthesized according to the following scheme:

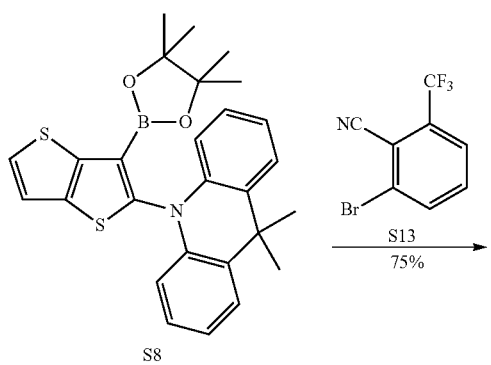

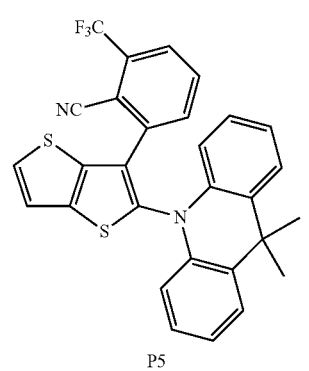

Under protection of nitrogen, Compound S8 (20 mmol), Compound S13 (20 mmol), [Pd$_2$(dba)$_3$].CHCl$_3$ (0.4 mmol) and HP(t-Bu)$_3$.BF$_4$ (0.8 mmol) were weighed and then added to a 250 mL flask with two necks. 100 mL of toluene (N$_2$ was introduced in advance for 15 minutes to remove oxygen) was added into the flask, and then 12 mL of a 1M aqueous solution of K$_2$CO$_3$ (N$_2$ was introduced in advance for 15 minutes to remove oxygen) was added dropwise and stirred at room temperature overnight. After the reaction was completed, 100 mL of deionized water was added and a few drops of 2M HCl were added. The organic phase was collected and dried over anhydrous Na$_2$SO$_4$ after extracting with dichloromethane. The dried solution was filtered, and the solvent was removed using a rotary evaporator to obtain a crude product. The crude product was purified through a silica gel column chromatography to obtain a solid P5 (15.0 mmol, 75%).

MALDI-TOF MS: m/z calculated for C$_{29}$H$_{19}$F$_3$N$_2$S$_2$: 516.1. found: 516.5.

Elemental analysis: calculated: C, 67.42; H, 3.71; F, 11.03; N, 5.42; S, 12.41. found: C, 67.45; H, 3.73; F, 11.02; N, 5.40; S, 12.39.

Example 4

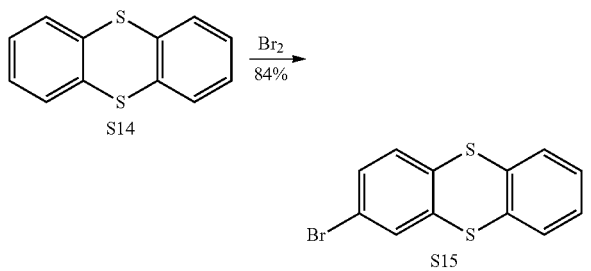

Under a nitrogen-protected condition, Compound S14 (30 mmol) was weighed and added to 60 mL of acetic acid. 36 mmol of liquid bromine was added dropwise during stirring, and the obtained mixture was stirred at 80° C. for 5 hours. The excess elemental bromine was quenched with an aqueous solution of NaHSO$_3$. The organic phase was collected and dried over anhydrous Na$_2$SO$_4$ after extracting with dichloromethane (100 mL×3). The dried solution was filtered, and the solvent was removed using a rotary evaporator to obtain a crude product. The crude product was purified through a silica gel column chromatography to obtain a solid power S15 (25.2 mmol, 84%).

MALDI-TOF MS: m/z calculated for C$_{12}$H$_7$BrS$_2$: 293.9. found: 293.8.

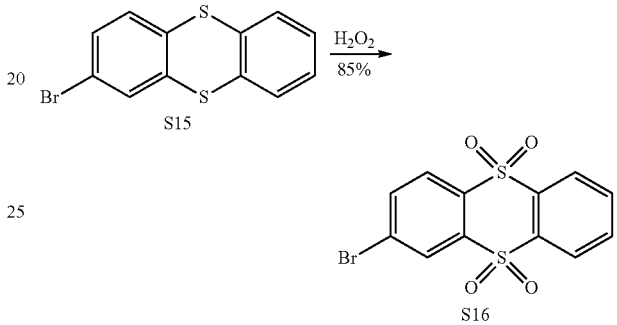

40 mL of glacial acetic acid, 20 mL of dichloromethane, the intermediate Compound S15 (6 mmol), 5 equivalent amount of 30% hydrogen peroxide were added into a 50 mL single-necked flask at room temperature, then the mixture was stirred at 55-60° C. for 20-24 h. After being cooled to room temperature, the mixture was extracted with dichloromethane to obtain a white solid S16 (5.1 mmol, 85%) by column chromatography.

MALDI-TOF MS: m/z calculated for C$_{12}$H$_7$BrO$_4$S$_2$: 357.9. found: 358.0.

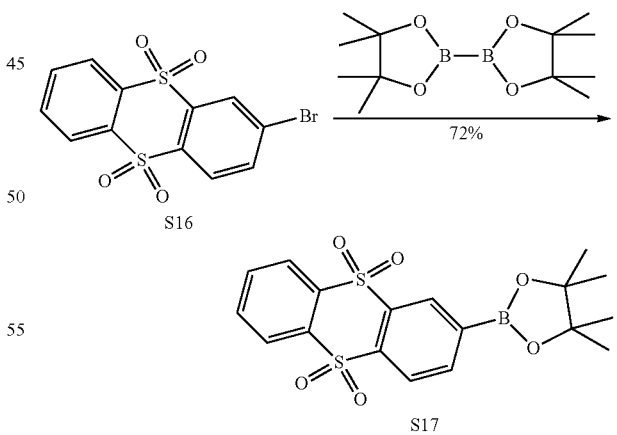

Compound S16 (30 mmol), bis(pinacolato)diboron (36 mmol), [1,1'-bis(diphenylphosphino)ferrocene]dichloropalladium(II) (0.3 mmol) and potassium acetate (75 mmol) were added to a 250 mL flask with three necks, and 100 mL of tetrahydrofuran was added through a syringe after repeating degassing and nitrogen replacement three times during stirring. After stirring at a certain rotation speed, the mixture was refluxed at a reaction temperature of 80° C. for 5 hours. After the reaction was completed, the mixture was cooled to room temperature, extracted with diethyl ether after adding 100 ml of water, and the organic phase was dried over anhydrous sodium sulfate. The solvent was removed by evaporation, and the crude product was purified by column chromatography to obtain an intermediate Compound S17 (21.6 mmol, 72%).

MALDI-TOF MS: m/z calculated for $C_{18}H_{19}BO_6S_2$: 406.1. found: 406.5.

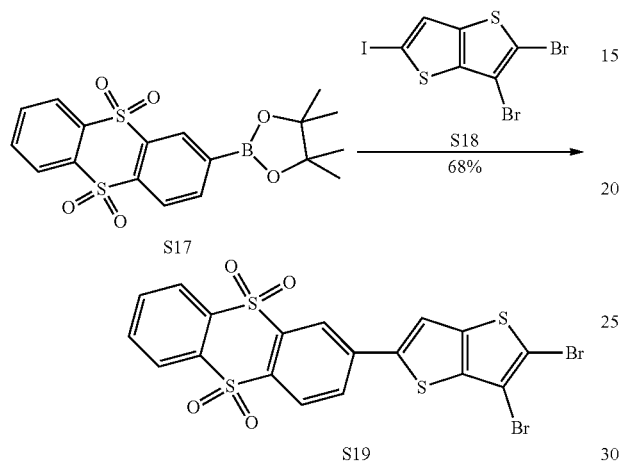

Under protection of nitrogen, Compound S17 (20 mmol), Compound S18 (20 mmol), [Pd$_2$(dba)$_3$].CHCl$_3$ (0.4 mmol) and HP(t-Bu)$_3$.BF$_4$ (0.8 mmol) were weighed and then added to a 250 mL flask with two necks. 100 mL of toluene (N$_2$ was introduced in advance for 15 minutes to remove oxygen) was added into the flask, and then 12 mL of 1M aqueous solution of K$_2$CO$_3$ (N$_2$ was introduced in advance for 15 minutes to remove oxygen) was added dropwise and stirred at room temperature overnight. After the reaction was completed, 100 mL of deionized water and a few drops of 2M HCl were added. The organic phase was collected and dried over anhydrous Na$_2$SO$_4$ after extracting with dichloromethane. The dried solution was filtered, and the solvent was removed using a rotary evaporator to obtain a crude product. The crude product was purified through a silica gel column chromatography to obtain a solid S19 (13.6 mmol, 68%).

MALDI-TOF MS: m/z calculated for $C_{18}H_8Br_2O_4S_4$: 573.8. found: 573.9.

Elemental analysis: calculated: C, 37.51; H, 1.40; Br, 27.73; O, 11.10; S, 22.25. found: C, 37.54; H, 1.42; Br, 27.72; O, 11.08; S, 22.23.

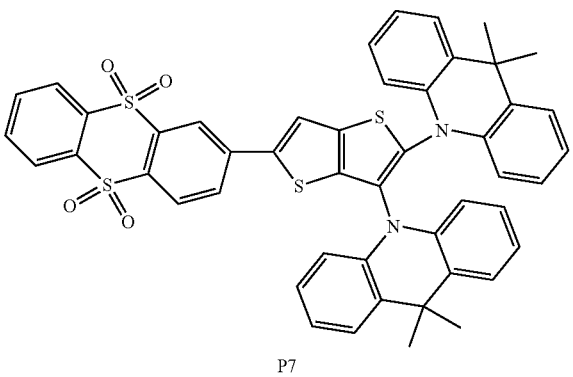

P7

Compound S19 (10 mmol), Compound S6 (21.5 mmol), (dibenzylideneacetone)dipalladium(0) (0.1 mmol), sodium t-butoxide (28 mmol) and tri-tert-butylphosphine (0.4 mmol) were added to a 100 mL flask with three necks, and 40 mL of toluene was added through a syringe after repeating degassing and nitrogen replacement three times during stirring. The mixture was refluxed for 3 hours under nitrogen stream. After the reaction was completed, the reaction mixture was cooled to room temperature, extracted with dichloromethane after adding water, and washed with saturated brine. After the organic layer was dried with anhydrous sodium sulfate, the solvent was removed by evaporation. The obtained crude product was purified by column chromatography to obtain Compound P7 (7.2 mmol, 72%).

MALDI-TOF MS: m/z calculated for $C_{48}H_{36}N_2O_4S_4$: 832.2. found: 832.6.

Elemental analysis: calculated: C, 69.20; H, 4.36; N, 3.36; O, 7.68; S, 15.40. found: C, 69.23; H, 4.32; N, 3.34; O, 7.66; S, 15.39.

Example 5

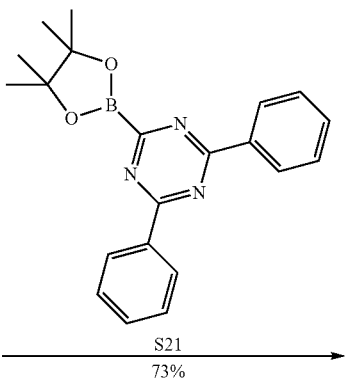

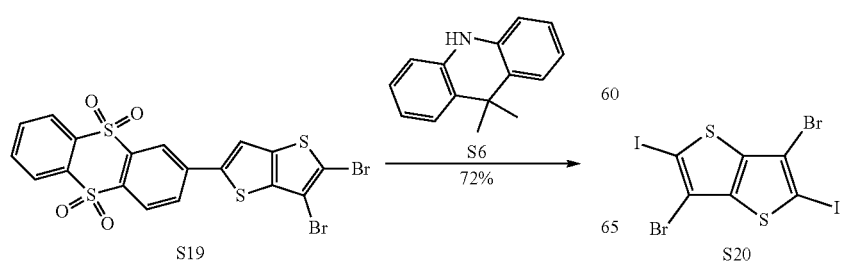

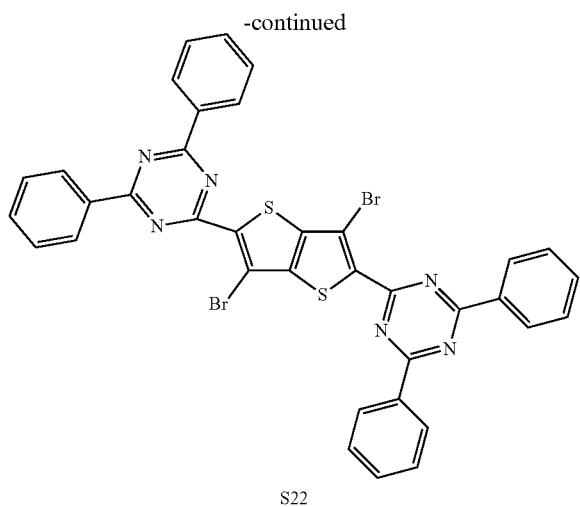

S22

Under protection of nitrogen, Compound S20 (20 mmol), Compound S21 (41 mmol), [Pd$_2$(dba)$_3$]·CHCl$_3$ (0.8 mmol) and HP(t-Bu)$_3$·BF$_4$ (1.6 mmol) were weighed and then added to a 500 mL flask with two necks. 200 mL of toluene (N$_2$ was introduced in advance for 15 minutes to remove oxygen) was added into the flask, and then 24 mL of 1M aqueous solution of K$_2$CO$_3$ (N$_2$ was introduced in advance for 15 minutes to remove oxygen) was added dropwise and stirred at room temperature overnight. After the reaction was completed, 150 mL of deionized water was added and a few drops of 2M HCl were added. The organic phase was collected and dried over anhydrous Na$_2$SO$_4$ after extracting with dichloromethane. The dried solution was filtered, and the solvent was removed using a rotary evaporator to obtain a crude product. The crude product was purified through a silica gel column chromatography to obtain a solid S22 (14.6 mmol, 73%).

MALDI-TOF MS: m/z calculated for C$_{36}$H$_{20}$Br$_2$N$_6$S$_2$: 758.0. found: 758.2.

Elemental analysis, calculated: C, 56.85; H, 2.65; Br, 21.01; N, 11.05; S, 8.43. found: C, 56.88; H, 2.67; Br, 21.00; N, 11.03; S, 8.41.

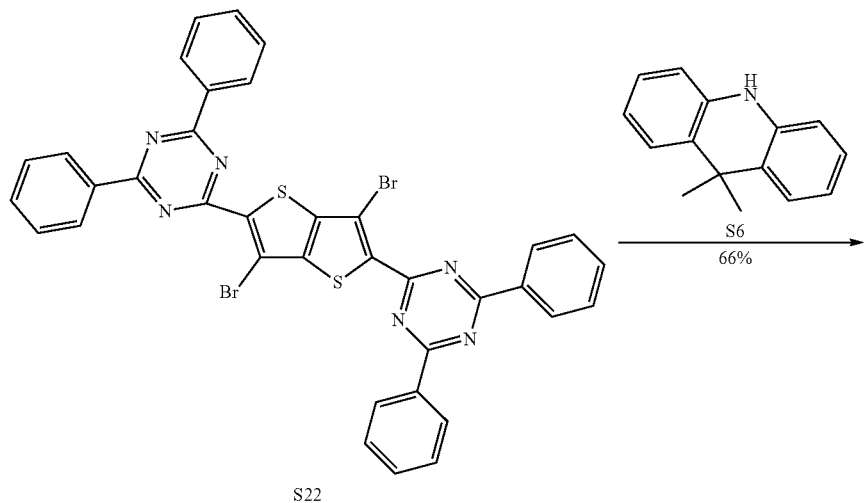

S22

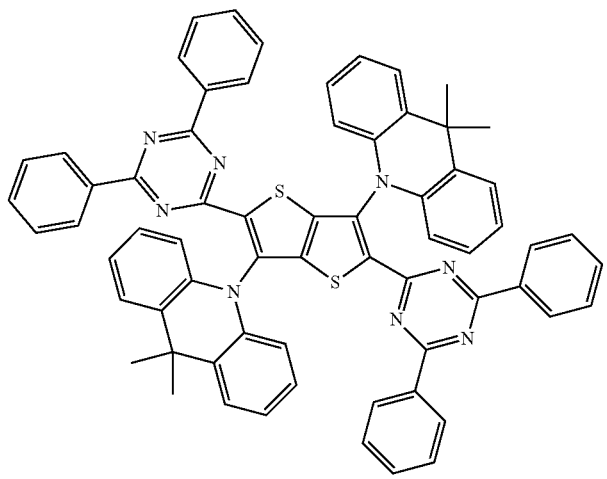

P8

Compound S22 (10 mmol), Compound S6 (21.5 mmol), (dibenzylideneacetone)dipalladium(0) (0.1 mmol), sodium t-butoxide (28 mmol) and tri-tert-butylphosphine (0.4 mmol) were added to a 100 mL flask with three necks, and 40 mL of toluene was added through a syringe after repeating degassing and nitrogen replacement three times during stirring. The mixture was refluxed for 3 hours under nitrogen stream. After the reaction was completed, the reaction mixture was cooled to room temperature, extracted with dichloromethane after adding water, and washed with saturated brine. After the organic layer was dried with anhydrous sodium sulfate, the solvent was removed by evaporation. The obtained crude product was purified by column chromatography to obtain Compound P8 (6.6 mmol, 66%).

MALDI-TOF MS: m/z calculated for $C_{66}H_{48}N_8S_2$: 1016.3. found: 1016.6.

Elemental analysis, calculated: C, 77.92; H, 4.76; N, 11.02; S, 6.30. found: C, 77.95; H, 4.78; N, 11.00; S, 6.27.

Example 6

Simulation Using Gaussian 09 Software

With respect to Compounds P1 to P10, the distribution of the molecular frontier orbitals HOMO and LUMO were optimized and calculated by applying a density functional theory (DFT) and using a Gaussian 09 software with B3LYP/6-31G calculation level. Meanwhile, the singlet energy level $S_1$, the triplet energy level $T_1$, and $\Delta E_{ST}$ were simulated and calculated based on a time-dependent density functional theory (TDDFT). The simulation method is described in J. Chem. Theory Comput., 2013, DOI: 10.1021/ct400415r.

Figure 2:
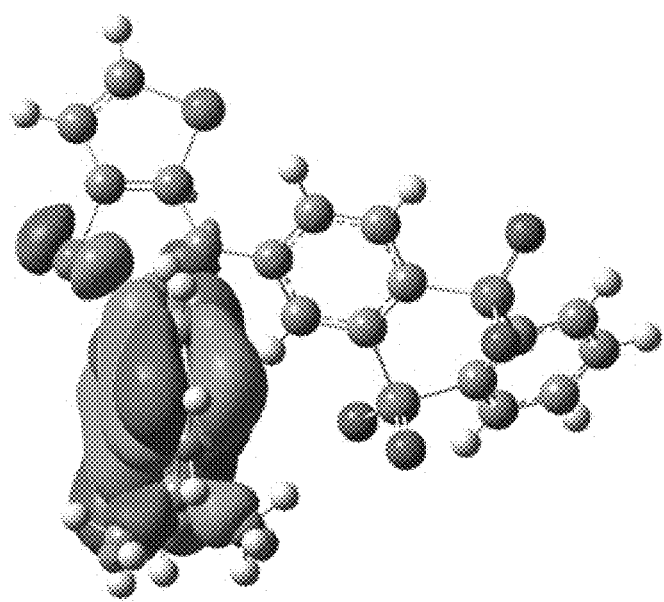
FIG. 2 is an energy level diagram of highest occupied molecular orbital (HOMO) of a compound, according to an embodiment of the present disclosure.
Figure 3:
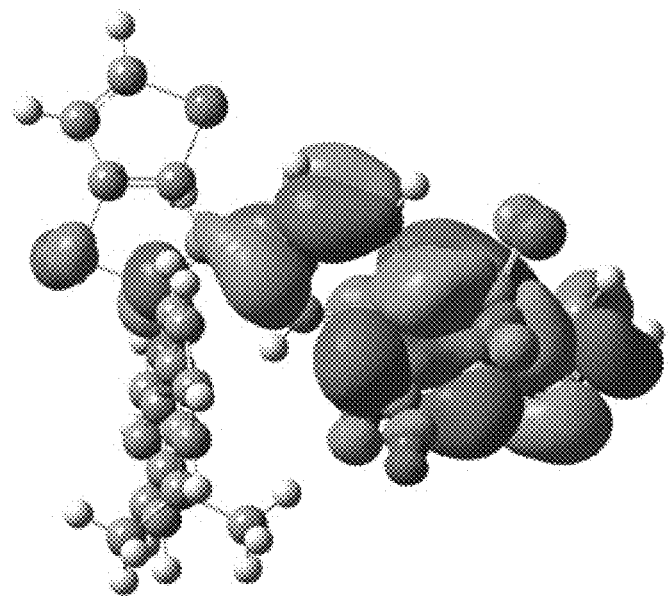
FIG. 3 is an energy level diagram of lowest unoccupied molecular orbital (LUMO) of a compound, according to an embodiment of the present disclosure.

FIG. 2 and FIG. 3 illustrate orbital configurations of Compound P1. Specifically, FIG. 2 is an energy level diagram of HOMO of Compound P1, and FIG. 3 is an energy level diagram of LUMO of Compound P1. It can be seen from FIG. 2 that the HOMO and the LUMO of the Compound P1 are distributed on different units, i.e., a complete separation is achieved. Thus, the intersystem energy difference $\Delta E_{ST}$ can be reduced, thereby enhancing the reverse intersystem crossing ability.

Data of Compounds P1 to P10 are shown in Table 1.

TABLE 1

Relevant Performance Data of Compounds P1-P10

| No. | Compound | HOMO (eV) | LUMO (eV) | $S_1$ (eV) | $T_1$ (eV) | $\Delta E_{ST}$ (eV) | Eg (eV) |
|---|---|---|---|---|---|---|---|
| 1 | P1 | −5.77 | −3.28 | 2.71 | 2.60 | 0.11 | 2.49 |
| 2 | P2 | −5.77 | −3.61 | 2.52 | 2.43 | 0.09 | 2.16 |
| 3 | P3 | −5.67 | −3.62 | 2.32 | 2.18 | 0.14 | 2.05 |
| 4 | P4 | −5.75 | −3.47 | 2.75 | 2.46 | 0.29 | 2.28 |
| 5 | P5 | −5.94 | −3.12 | 3.03 | 2.75 | 0.28 | 2.82 |
| 6 | P6 | −5.55 | −3.31 | 2.04 | 2.03 | 0.01 | 2.24 |
| 7 | P7 | −5.73 | −3.35 | 2.91 | 2.63 | 0.28 | 2.38 |
| 8 | P8 | −5.59 | −3.38 | 2.03 | 2.02 | 0.01 | 2.21 |
| 9 | P9 | −5.91 | −3.59 | 2.79 | 2.51 | 0.28 | 2.32 |
| 10 | P10 | −5.62 | −3.53 | 2.62 | 2.36 | 0.26 | 2.09 |

In Table 1, $S_1$ represents a singlet energy level, $T_1$ represents a triplet energy level, $\Delta E_{ST}$ represents an energy difference between the singlet energy level and the triplet energy level, and Eg represents an energy difference between HOMO and LUMO energy level.

It can be seen from Table 1 that the $\Delta E_{ST}$ of respective compound is less than 0.3 ev, which means a small difference between the singlet energy level and the triplet energy level. At the same time, a fluorescence lifetime of respective compound is of a magnitude of microsecond, revealing a significant delayed fluorescence effect.

Figure 4:
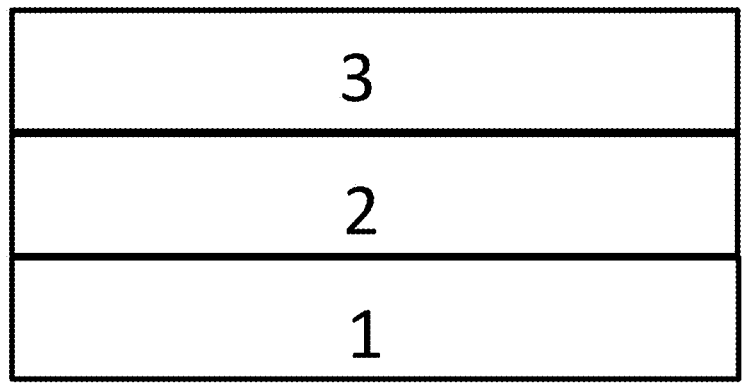
FIG. 4 is a structural schematic diagram of an organic light-emitting component, according to an embodiment according to the present disclosure.

In a second aspect, the present disclosure provides an organic light-emitting display device. The organic light-emitting display device includes an anode, a cathode, and at least one organic thin film layer disposed between the anode and the cathode, as shown in FIG. 4. The organic thin film layer serves as a light-emitting layer of the organic light-emitting display device. A light-emitting material of the light-emitting layer is selected from the group consisting of one or more of the aromatic heterocyclic compounds according to the present disclosure, and combinations thereof.

FIG. 4 is a schematic structural diagram of an organic light-emitting component according to an embodiment of the present disclosure. The organic light-emitting component includes a first electrode 1, a light-emitting layer 2, and a second electrode 3 that are stacked sequentially. A substrate can be additionally provided under the first electrode 1 or above the second electrode 3. Any substrate known in the conventional organic light-emitting components can be used. In an embodiment, the substrate can be a glass substrate or a transparent plastic substrate that has excellent properties of mechanical strength, thermal stability, transparency, surface smoothness, operability, and water resistance.

The light-emitting layer 2 disposed on the first electrode 1 includes a hole transmission region, an emission layer, and an electron transmission region. The hole transmission region may be disposed between the first electrode 1 and the light-emitting layer 2. The hole transmission region may include at least one of a hole injection layer, a hole transmission layer, an electron blocking layer or a buffering layer. Alternatively, the hole transmission region includes multiple layers formed by any combination thereof. The hole transmission region may only include a hole injection layer or a hole transmission layer. The hole transmission region may include a buffering layer. The buffering layer can compensate the optical resonance distance based on the wavelength of light emitted from the light-emitting layer 2, and thus improve the efficiency of the organic light-emitting component.

The light-emitting layer 2 may include a host material and a dopant. The electron transmission region may include at least one of a hole blocking layer, an electron transmission layer, an electron injection layer, or the electron transmission region may include multiple layers formed by any combination thereof. For example, the electron transmission region may have a structure of hole blocking layer/electron transmission layer/electron injection layer, or a structure of electron transmission layer/electron injection layer, which is not limited thereto. The electron transmission layer may have a single layer structure or a multilayer structure that contains two or more different materials.

In an embodiment, the anode can be made of metal selected from a group consisting of copper, gold, silver, iron, chromium, nickel, manganese, palladium, platinum, etc., and alloys thereof. The anode also can be made of metal oxide, such as indium oxide, zinc oxide, indium tin oxide (ITO), indium zinc oxide (IZO), and the like. The anode also can be made of a conductive polymer, such as polyaniline, polypyrrole, poly(3-methylthiophene) and the like. In addition to the anode material mentioned above, the anode also can be made of any suitable material selected from the anode materials known in the related art, and combinations thereof, as long as the material of the anode is conductive to injecting holes.

In the organic light-emitting display device provided by the present disclosure, the cathode can be made of metal, such as aluminum, magnesium, silver, indium, tin, titanium, etc., or alloys thereof. The cathode also can be made of multiple-layer metal material, such as LiF/Al, LiO$_2$/Al, BaF$_2$/Al, and the like. In addition to the cathode materials listed above, the cathode also can be made of any suitable material selected from the cathode material known in the related art, and combinations thereof, as long as the material of the cathode is conductive to injecting holes.

In the present disclosure, the organic light-emitting display device can be manufactured by forming an anode on a transparent or opaque smooth substrate, forming an organic thin layer on the anode, and further forming a cathode on the organic thin layer. The organic thin layer can be formed by a known method such as vapor deposition, sputtering, spin coating, dipping, ion plating, and the like.

The compound according to the present disclosure can be used as a dopant, a co-dopant, or a host material in the light-emitting layer.

In an embodiment, the light-emitting layer of the organic light-emitting display device includes a host material or a guest material. In an embodiment, the host material or the guest material is selected from the group consisting of the compounds according to the present disclosure, and combinations thereof.

In an embodiment, the light-emitting material of the light-emitting layer is a red light-emitting material, and the red light-emitting material has a singlet energy level of 1.61-1.99 eV.

In an embodiment, the light-emitting material of the light-emitting layer is a green light-emitting material, and the green light-emitting material has a singlet energy level of 2.15-2.52 eV.

In an embodiment, the light-emitting material of the light-emitting layer is a blue light-emitting material, and the blue light-emitting material has a singlet energy level of 2.52 to 2.73 eV.

In the organic light-emitting display device according to an embodiment of the present disclosure, the light-emitting material includes a host material and a guest material. The host material is selected from the group consisting of 2,8-bis(diphenylphosphinyl)dibenzothiophene, 4,4'-bis(9-carbazolyl)biphenyl, 3,3'-bis(N-carbazolyl)-1,1'-biphenyl, 2,8-bis(diphenylphosphinyl)dibenzofuran, bis(4-(9H-carbazolyl-9-yl)phenyl)diphenylsilane, 9-(4-tert-butylphenyl)-3,6-bis(triphenyl silyl)-9H-carbazole, bis(2-diphenylphosphinyl)diphenyl ether, 1,3-bis[3,5-di(pyridine-3-yl)phenyl]benzene, 4,6-bis(3,5-di(3-pyridyl)phenyl)-2-methylpyrimidine, 9-(3-(9H-carbazolyl-9-yl)phenyl)-9H-carbazole-3-cyano, 9-phenyl-9-[4-(triphenyl silyl)phenyl]-9H-fluorene, 1,3,5-tris(1-phenyl-1H-benzoimidazol-2-yl)benzene, diphenyl[4-(triphenylsilyl)phenyl]phosphine oxide, 4,4',4''-tris(carbazol-9-yl)triphenylamine, 2,6-dicarbazolyl-1,5-pyridine, polyvinylcarbazole, polyfluorene, and combinations thereof. In an embodiment, the guest material is selected from the group consisting of the aromatic heterocyclic compounds according to the present disclosure, and combinations thereof. In an embodiment an energy difference between a HOMO energy level of the host material and a HOMO energy level of the guest material is less than 0.6 eV, or an energy difference between a LUMO energy level of the host material and a LUMO energy level of the guest material is less than 0.6 eV.

In an embodiment, a singlet energy level of the host material is higher than a singlet energy level of the guest material, and an energy difference between the singlet energy level of the host material and the singlet energy level of the guest material is less than 1.0 eV.

In the organic light-emitting display device according to an embodiment of the present disclosure, the light-emitting material of the light-emitting layer includes a host material and a guest material. In an embodiment, the host material is selected from the group consisting of the aromatic heterocyclic compounds according to the present disclosure, and combinations thereof. In an embodiment, the guest material is selected from the group consisting of fluorescent material, thermally activated delayed fluorescent material, and phosphorescent material. In an embodiment, an energy difference between a HOMO energy level of the host material and a HOMO energy level of the guest material is less than 0.6 eV, or an energy difference between a LUMO energy level of the host material and a LUMO energy level of the guest material is less than 0.6 eV.

In the organic light-emitting display device according to an embodiment of the present disclosure, the light-emitting material of the light-emitting layer includes a host material and a guest material, the host material is selected from the group consisting of the aromatic heterocyclic compounds according to the present disclosure, and combinations thereof. In an embodiment, the guest material is selected from a fluorescent material or a thermally activated delayed fluorescent material. In an embodiment, a singlet energy level of the guest material is less than a singlet energy level of the host material, and a difference between the singlet energy level of the host material and the singlet energy level of the guest material is less than 1.0 eV.

In an embodiment. The light-emitting material of the light-emitting layer includes a host material and a guest material. The host material is selected from the group consisting of the aromatic heterocyclic compounds according to the present disclosure, and combinations thereof. In an embodiment, the guest material is a phosphorescent material. In an embodiment, a triplet energy level of the guest material is lower than a triplet energy level of the host material, and an energy difference between the triplet energy level of the host material and the triplet energy level of the guest material is less than 1.0 eV.

According to an embodiment of the present disclosure, the light-emitting material is a thermally activated delayed fluorescent material.

In an embodiment, the organic functional layer according to the present disclosure further includes at least one of a hole injection layer (HIL), a hole transmission layer (HTL), an electron blocking layer (EBL), a hole blocking layer (HBL), an electron transmission layer (ETL), and an electron injection layer (EIL).

In an embodiment, the hole injection layer, the hole transmission layer, and the electron blocking layer includes a material selected from a group consisting of N,N'-diphenyl-N,N'-bis(1-naphthyl)-1,1'biphenyl-4,4''diamine (α-NPD), 4,4',4''-tris(carbazol-9-yl)-triphenylamine (TCTA), 1,3-bis(N-carbazolyl)benzene (mCP), 4,4'-bis(9-carbazole)biphenyl (CBP), 3,3'-bis(N-carbazolyl)-1,1'-biphenyl (mCBP), 2,3,6,7,10,11-hexacyano-1,4,5,8,9,12-hexaazatriphenylene (HATCN), 4,4'-cyclohexylidenebis[N,N-bis(4-methylphenyl)aniline] (TAPC), N,N'-diphenyl-N,N'-(1-naphthyl)-1,1'-biphenyl-4,4'-diamine (α-NPB), N,N'-bis(naphthalen-2-yl)-N,N'-di(phenyl)biphenyl-4,4'-diamine (NPB), poly(3,4-ethylenedioxythiophene)-polystyrene-sulfonate (PEDOT: the PSS), polyvinyl carbazole (PVK), 9-phenyl-3,9-bicarbazolyl (CCP), molybdenum trioxide (MoO$_3$). However, such materials are not limited thereto.

In an embodiment, the hole blocking layer, the electron transmission layer, or the electron injection layer includes a material selected from the group consisting of 2,8-bis(diphenylphosphinyl)dibenzothiophene (PPT), TSPO1, TPBi, 2,8-bis(diphenylphosphinyl)dibenzofuran (PPF), bis[2-(diphenylphosphino)phenyl]ether oxide (DPEPO), lithium fluoride (LiF), 4,6-bis(3,5-di-3-pyridylphenyl)-2-methylpyrimidine (B3PYMPM), 4,7-diphenyl-1,10-phenanthroline (Bphen), 1,3,5-tris[(3-pyridyl)-3-phenyl]benzene (TmPyBP), tri s[2,4,6-trimethyl-3-(3-pyridyl)phenyl]borane (3TPYMB), 1,3-bis(3,5-dipyridine-3-yl-phenyl)benzene (B3PYPB), 1,3-bis[3,5-di(pyridin-3-yl)phenyl]benzene (BMPYPHB), 2,4,6-Tris(biphenyl-3-yl)-1,3,5-triazine (T2T), diphenylbis(4-(pyridin-3-yl)phenyl)silane (DPPS), cesium carbonate ($Cs_2O_3$), bis(2-methyl-8-quinolinolato-N1,O8)-(1,1'-Biphenyl-4-olato)aluminum (BAlq), 8-hydroxyquinoline lithium (Liq), and tris(8-hydroxyquinoline) aluminum ($Alq_3$). However, such materials are not limited thereto.

The substrate according to the present disclosure can be a rigid substrate (borosilicate glass, float soda-lime glass, high refractive index glass, stainless steel, etc.), or a flexible substrate (for example, a polyimide (PI) plastic substrate, polyethylene terephthalate (PET) plastic substrate, poly(ethylene naphthalate) (PEN) plastic substrate, polyethersulfone resin substrate (PES), polycarbonate plastic substrate (PC), ultra-thin flexible glass substrate, metal foil substrate, etc.).

Figure 5:
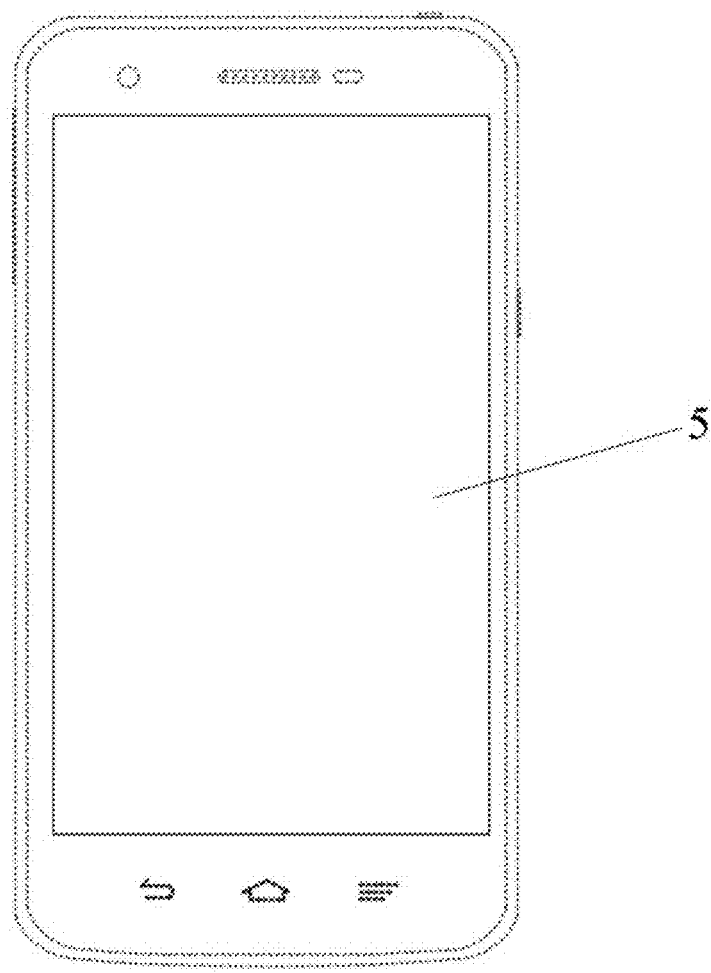
FIG. 5 is a structural schematic diagram of an organic light-emitting display device, according to an embodiment according to the present disclosure.

In an embodiment, the organic light-emitting display device is an organic light-emitting display device including an OLED. The organic light-emitting display device may be a display screen or display panel of mobile phone, computer, liquid crystal television, smart watch, smart car, VR or AR helmet, and other smart devices. FIG. 5 is a schematic diagram of a display screen of mobile phone, in which the display screen is denoted with number 5.

The following Example 7 to Example 9 aim to show the manufacturing process and performances of the organic light-emitting components.

Example 7

Manufacturing Process of Organic Light-Emitting Component by Vapor Deposition Method A substrate having an ITO film with a thickness of 100 nm was ultrasonically washed with distilled water, acetone, and isoinol, then dried in an oven, and the surface was subjected to UV treatment for 30 minutes. Then the substrate was transferred to a vacuum vapor deposition chamber. The vapor deposition of each layer was carried out under a vacuum of $2\times10^{-6}$ Pa. A hole injection layer was formed by deposing 5 nm of HATCN. A hole transmission layer (HTL) was formed by deposing 40 nm of N,N'-diphenyl-N,N'-bis (1-naphthyl)-1,1'biphenyl-4,4"diamine (α-NPD) and then deposing 10 nm of 4,4',4"-tris(carbazol-9-yl)-triphenylamine (TCTA). The compound according to the present disclosure used as a dopant of the light-emitting layer, and 3,3'-bis(N-carbazolyl)-1,1'-biphenyl (mCBP) used as a host material of the light-emitting layer, are deposited on the hole transmission layer at the same time, so as to form a light-emitting having a thickness of 35 nm. A hole blocking layer (HBL) having a thickness of 5 nm was deposited on the light-emitting layer with diphenyl [4-(triphenylsilyl)phenyl] phosphine oxide (TSPO1). An electron transmission layer (ETL) having a thickness of 30 nm was deposited on the hole blocking layer with 4,7-diphenyl-1,10-phenanthroline (Bphen). Then, a LiF layer having a thickness of 2.5 nm and an Al layer having a thickness of 100 nm were deposited on the electron transmission layer sequentially, serving as an electron injection layer (EIL) and a cathode respectively, so as to obtain an organic light-emitting display component.

The organic light-emitting component also can be manufactured by a solution method.

In an embodiment, the process of manufacturing a non-doped component includes following steps: ultrasonically washing an ITO glass with acetone, alkaline washing solution, ultrapure water, and isopropyl alcohol sequentially for two times, 15 minutes for each time; treating the ITO glass with an ozone cleaner for 15 minutes; spraying 40 nm of PEDOT:PSS solution onto the glass substrate with a ink-jet printer, and placing the glass substrate in a vacuum oven at 120° C. for 45 minutes for drying; preparing a TAPC layer and an mCP layer on PEDOT:PSS layer, serving as a hole transmission layer and an electron blocking layer, respectively; spraying a toluene solution of the compound according to the present disclosure (concentration: 12 mg/mL) with ink-jet printer so as to form a light-emitting layer having a thickness of 35 nm; transferring the substrate to a vacuum chamber; and vapor-depositing an electron transmission layer (TmPyPb, 50 nm), an electron injection layer (LiF, 0.5-1 nm), and a cathode (Al, 100 nm) to form a complete component.

In an embodiment, the process of manufacturing a doped component is the same as or similar to that for manufacturing the non-doped component, but further includes several additional steps: preparing solutions of a host material of the light-emitting material and a guest material of the light-emitting material in o-dichlorobenzene (concentration: 12 mg/mL), separately; adding, by a micropipette, 50 uL (5%) of the solution of the guest material into the solution of the host material, and stirring the mixture homogenously by a magnetic stirrer; and then coating the light-emitting layer.

In an embodiment, the solution method includes an ink-jet printing method, spin coating, blade coating, screen printing, roll-to-roll printing, and the like. In an embodiment, the solution method of the present disclosure is the ink-jet printing method.

Example 8

Components Manufactured with Vacuum Vapor Deposition Method

Non-doped Components N1 to N10, in which Compounds P1 to P10 are used as light-emitting material respectively, were manufactured and each has a structure: ITO (100 nm)/α-NPD (40 nm)/TCTA (10 nm)/P (35 nm)/TmPyPb (50 nm)/LiF (0.5 nm)/Al (100 nm), and their performances are shown in Table 2.

TABLE 2

Performance of Non-doped Components Manufactured with Vacuum Vapor Deposition Method (Compounds P1 to P8 as Light-Emitting Material)

| Component | $V_{on}$ [V] | $CE_{(10\ mA/cm^2)}$ (cd $A^{-1}$) | $EQE_{(max)}$ (%) |
|---|---|---|---|
| N1 | 4.86 | 15.0 | 9.2 |
| N2 | 5.37 | 14.2 | 8.8 |
| N3 | 5.45 | 14.3 | 8.4 |
| N4 | 5.10 | 8.5 | 4.5 |
| N5 | 5.22 | 9.2 | 5.2 |
| N6 | 4.85 | 13.8 | 8.5 |
| N7 | 4.94 | 8.2 | 4.6 |

TABLE 2-continued

Performance of Non-doped Components Manufactured
with Vacuum Vapor Deposition Method (Compounds P1
to P8 as Light-Emitting Material)

| Component | $V_{on}$ [V] | $CE_{(10\ mA/cm^2)}$ (cd A$^{-1}$) | $EQE_{(max)}$ (%) |
|---|---|---|---|
| N8 | 5.16 | 13.8 | 8.5 |
| N9 | 5.20 | 7.9 | 4.8 |
| N10 | 4.98 | 9.4 | 5.1 |

Doped Components N11 to N20, in which Compounds P1 to P10 are used as fluorescent dopant respectively, were manufactured and each has a structure: ITO (100 nm)/α-NPD (40 nm)/TCTA (10 nm)/CBP: P (35 nm)/TmPyPb (50 nm)/LiF (0.5 nm)/Al (100 nm). Moreover, as a comparative example, a doped Component C1, in which BCzVBi was used as fluorescent dopant and CBP was used as host material, was manufactured and has a structure: ITO (100 nm)/α-NPD (40 nm)/TCTA (10 nm)/CBP: BCzVBi (35 nm, 5%)/TmPyPb (50 nm)/LiF (0.5 nm)/Al (100 nm). The performances data are shown in Table 3.

TABLE 3

Performance of Doped Components Manufactured with
Vacuum Vapor Deposition Method (Compounds P1 to
P10 as Fluorescent Dopant)

| Device | $V_{on}$ [V] | $CE_{(10\ mA/cm^2)}$ (cd A$^{-1}$) | $EQE_{(max)}$ (%) |
|---|---|---|---|
| N11 | 4.88 | 32.1 | 16.9 |
| N12 | 5.25 | 33.6 | 17.2 |
| N13 | 5.28 | 29.4 | 16.5 |
| N14 | 5.12 | 15.7 | 9.3 |
| N15 | 4.92 | 16.0 | 9.6 |
| N16 | 5.34 | 24.8 | 15.6 |
| N17 | 5.18 | 14.5 | 8.8 |
| N18 | 5.16 | 33.2 | 16.6 |
| N19 | 5.04 | 15.2 | 9.0 |
| N20 | 4.90 | 15.6 | 9.2 |
| C1 | 4.8 | 6.9 | 4.4 |

It can be seen from Table 2 and Table 3 that, among the non-doped components, which were manufactured by using Compounds P1 to P10 as light-emitting material with vacuum vapor deposition method, a maximum external quantum efficiency of 9.2% was reached. This indicates that, by introducing benzothiophene group, the interaction between the electron donor D and the electron acceptor A is more intense, the molecular distortion strength is increased and thus a larger dihedral angle is formed, thereby achieving an effective separation HOMO from LUMO and solving a problem about exciton quenching caused by π-π stacking. Meanwhile, a certain rigidity of the molecules can be maintained, and a high photoluminescence quantum yield (PLQY) can be achieved, so as to obtain a component having satisfying performances.

Further, it can be seen from Table 3 that the doped Components N11 to N20 each has a significantly higher $EQE_{(max)}$ than the comparative Component C1, in which a conventional blue light-emitting material BCzVBi was used as fluorescent dopant. This can be attributed to the property of TADF of Compounds P1 to P10. The property of TADF achieves that triplet excitons can emit light to improve the efficiency of the component, which is inhibited in the conventional fluorescent molecules (such as BCzVBi)

Among the doped components, in which Compounds P1 to P10 were used as dopant light-emitting material and mCBP was used as host material, a maximum external quantum efficiency of 17.2% was achieved, which is significantly improved compared with the non-doped components. This indicates that the π-π stacking effect and concentration quenching can be reduced by introducing dopant into the host material.

Doped Components N21 and N22, in which Compound P1 and Compound P2 were used as host material and a fluorescent material was used as dopant, were manufactured and each has a structure: ITO (100 nm)/α-NPD (40 nm)/TCTA (10 nm)/P1 or P2: dopant (fluorescent material) (35 nm)/TmPyPb (50 nm)/LiF (0.5 nm)/Al (100 nm). The fluorescent material is rubrene. Their performances are shown in Table 4.

Doped Components N23 and N24, in which Compound P1 and Compound P2 were used as host material and a phosphorescent material was used as dopant, were manufactured and each has a structure: ITO (100 nm)/α-NPD (40 nm)/TCTA (10 nm)/P1 or P2: dopant (phosphorescent material) (35 nm)/TmPyPb (50 nm)/LiF (0.5 nm)/Al (100 nm). The phosphorescent material is Ir(ppy)3. Their performances are shown in Table 4.

TABLE 4

Performances of Doped Components Manufactured
by Vacuum Vapor Deposition Method

| Component | $V_{on}$ [V] | $CE_{(10\ mA/cm^2)}$ (cd A$^{-1}$) | $EQE_{(max)}$ (%) |
|---|---|---|---|
| N21 | 4.20 | 12.6 | 7.6 |
| N22 | 4.18 | 13.2 | 8.0 |
| N23 | 3.98 | 40.5 | 17.4 |
| N24 | 3.94 | 42.6 | 17.8 |

It can be seen from Table 4 that among the doped components, in which the Compound P1 and Compound P2 were used as the host material, and rubrene was used as the dopant material, maximum external quantum efficiencies of 7.6% and 8.0% were achieved. That indicates that the compounds according to the present disclosure can be used as host material of the fluorescent material.

It also can be seen from Table 4 that among the doped components, in which the Compound P1 and Compound P2 were used as the host material, and Ir(ppy)3 was used as the dopant material, maximum external quantum efficiencies of 17.4% and 17.8% were achieved. That indicates that the compounds according to the present disclosure can be used as host material of the phosphorescent material.

Example 9

Components Manufactured by Solution Method

A corresponding doped Component N25 and a corresponding non-doped Component N26, in which the Compound P1 was used as the light-emitting material, were manufactured by a solution method. The doped Component N25 has a structure: ITO (100 nm)/PEDOT: PSS (40 nm)/PVK: P1 (35 nm)/TmPyPb (50 nm)/LiF (0.5 nm)/Al (100 nm).

In the doped Component N25, a conventional polymer PVK was used as host material.

The non-doped Component N26 has a structure: ITO (100 nm)/PEDOT: PSS (40 nm)/P1 (35 nm)/TmPyPb (50 nm)/LiF (0.5 nm)/Al (100 nm).

Relevant data of the above components are shown in Table 5.

TABLE 5

Performances of Components Manufactured by Solution Method

| Component | $V_{on}$ [V] | $CE_{(10\ mA/cm^2)}$ (cd A$^{-1}$) | $EQE_{(max)}$ (%) |
|---|---|---|---|
| N25 | 4.88 | 23.2 | 12.4 |
| N26 | 4.96 | 10.8 | 6.2 |

As shown in Table 5, among the non-doped and doped components manufactured by the solution method, maximum external quantum efficiencies of 6.2% and 12.4% are achieved, respectively. Comparing with the vapor deposition method, the performance is slightly decreased, and the degradation may be caused by residual solvents in the solution method.

The above embodiments of the present disclosure are several preferred embodiments, but not intended to limit the scope of the claims. Any change and modification can be made by those skilled in the art without departing from the scope of the present application. The scope of protection is defined by the claims.

What is claimed is:

1. An aromatic heterocyclic compound, having a structure represented by Formula (I):

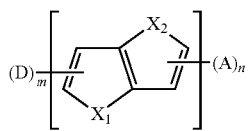

Formula (I)

wherein $X_1$ and $X_2$ are independently selected from S and O;

D is a chemical group acting as an electron donor,

A is a chemical group acting as an electron acceptor;

m is a number of the electron donors D, the m electron donors D are the same or different from one another;

n is a number of the electron acceptors A, the n electron acceptors are the same or different from one another; and m and n are integers independently selected from 1 and 2;

wherein any one of the m electron donors D is any one of following chemical groups:

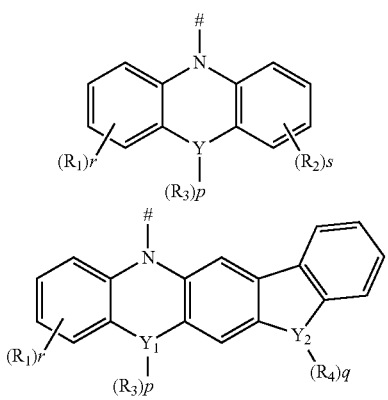

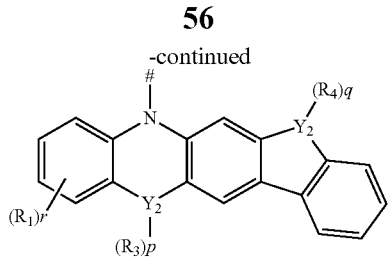

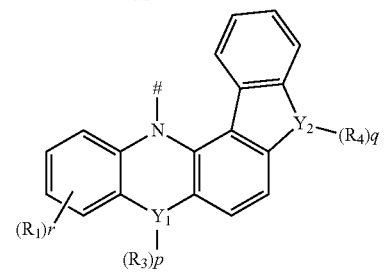

wherein Y, $Y_1$ and $Y_2$ are independently selected from the group consisting of carbon, nitrogen, oxygen, sulfur, and silicon;

indicates a bonding position;

r and s are integers independently selected from 0, 1, 2 and 3, and p and q are integers independently selected from 0, 1 and 2;

when Y is oxygen or sulfur, p=0 or q=0;

when Y is nitrogen, p and q are independently selected from 0 and 1;

when Y is carbon or silicon, p and q are independently selected from 0, 1 and 2; and $R_1$, $R_2$, $R_3$ and $R_4$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C13-C40 acridinyl, substituted or unsubstituted C3-C40 azine group, and groups represented by Formula (21):

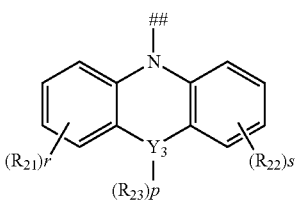

Formula (21)

wherein $Y_3$ is selected from the group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and ## indicates a bonding position; or any one of the m electron donors D is any one of following chemical groups:

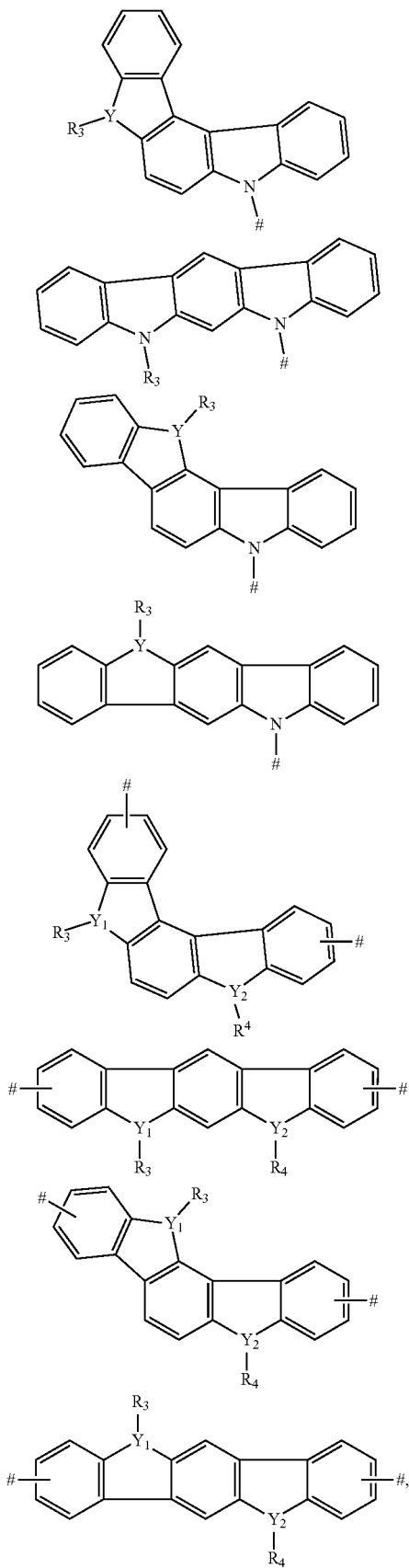

wherein Y, $Y_1$ and $Y_2$ are independently selected from the group consisting of carbon, nitrogen, oxygen, sulfur and silicon;

x and y are integers independently selected from 0, 1, 2 and 3;

indicates a bonding position;

when Y is oxygen or sulfur, $R_3$ is absent;

when $Y_1$ is oxygen or sulfur, $R_3$ is absent;

when $Y_2$ is oxygen or sulfur, $R_4$ is absent; and $R_1$, $R_2$, $R_3$ and $R_4$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C3-C40 azine group, and groups represented by formula (21):

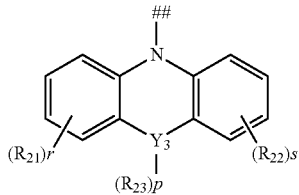

Formula (21)

wherein $Y_3$ is selected from a group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and ## indicates a bonding position; or any one of the m electron donors D is any one of following chemical groups:

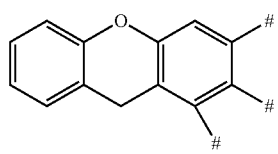

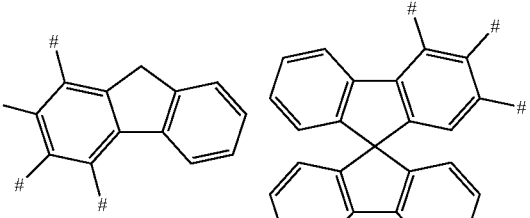

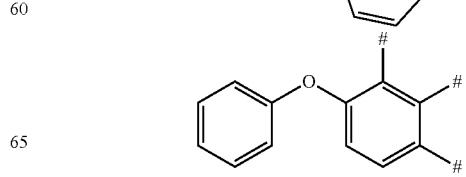

-continued

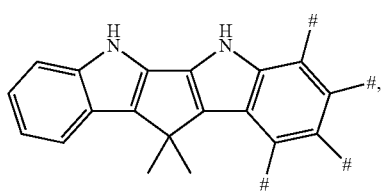

wherein # indicates a bonding position; and any one of the n electron acceptors A is selected from the group consisting of a cyano-containing substituent, a triaryl boron substituent, a benzophenone substituent, an aromatic heterocyclic ketone substituent, and a sulfone substituent.

2. The aromatic heterocyclic compound according to claim 1, wherein any one of the m electron donors D is any one of following chemical groups:

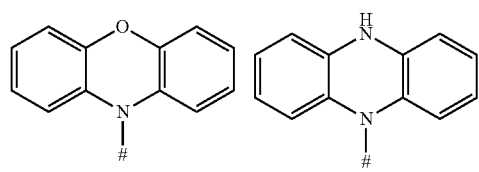

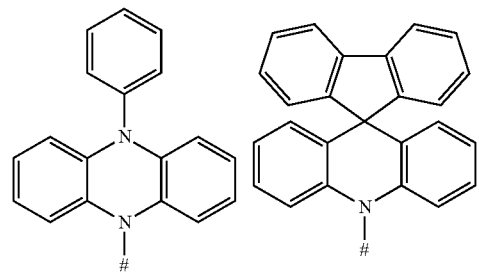

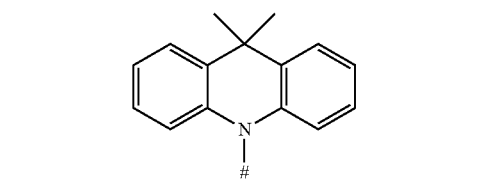

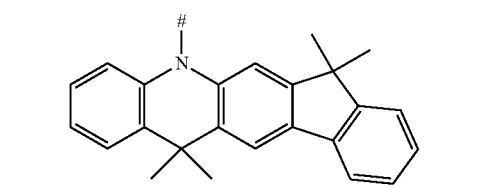

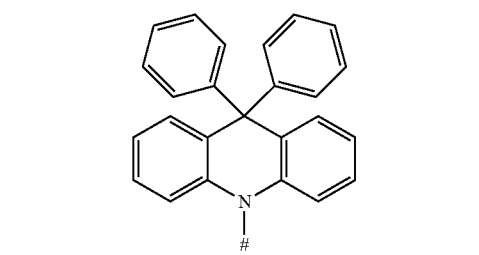

-continued

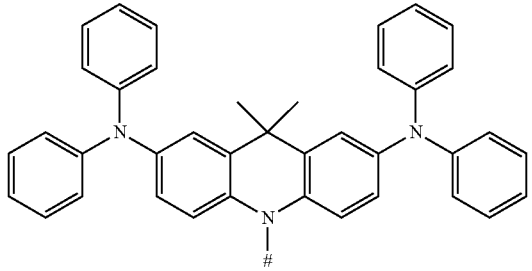

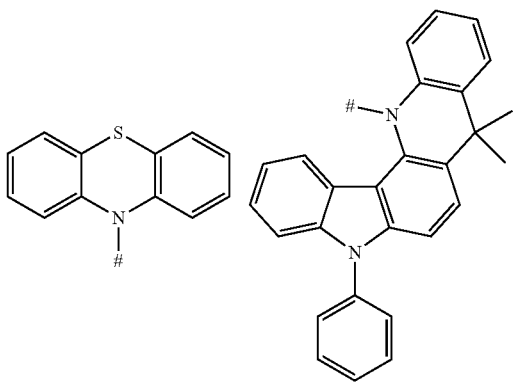

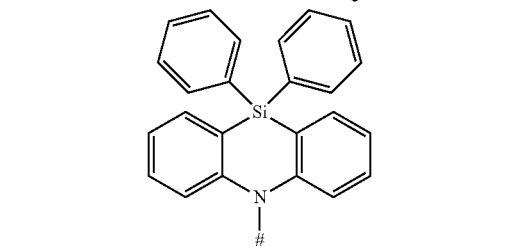

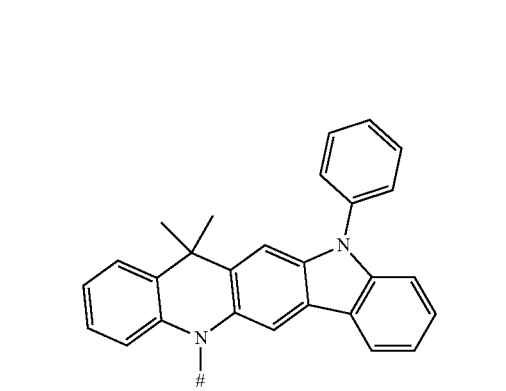

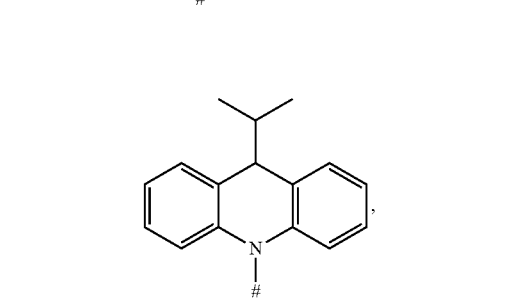

wherein # indicates a bonding position.

3. The aromatic heterocyclic compound according to claim 1, wherein any one of the m electron donors D is any one of following chemical groups:

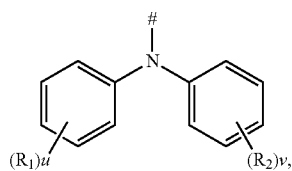

wherein # indicates a bonding position;
u and v are integers independently selected from 0, 1, 2 and 3;
R$_1$ and R$_2$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl and its derivative groups, substituted or unsubstituted C12-C40 diphenylamino and its derivative groups, substituted or unsubstituted C3-C40 azine group and its derivative groups, and groups represented by Formula (21):

Formula (21)

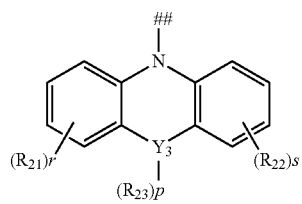

wherein Y$_3$ is selected from the group consisting of carbon, nitrogen, oxygen, sulfur, and silicon;
R$_{21}$, R$_{22}$ and R$_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;
r and s are integers independently selected from 0, 1, 2 and 3, and
p is an integer selected from 0, 1 and 2;
when Y$_3$ is oxygen or sulfur, p=0; and
indicates a bonding position.

4. The aromatic heterocyclic compound according to claim 3, wherein any one of the m electron donors D is any one of following chemical groups:

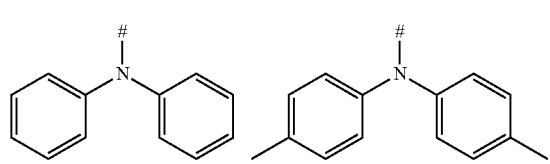

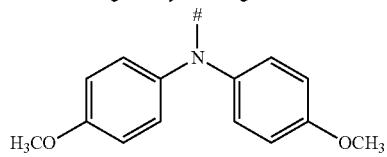

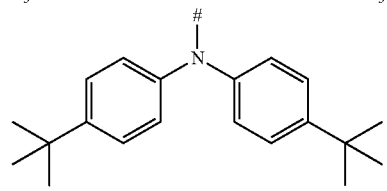

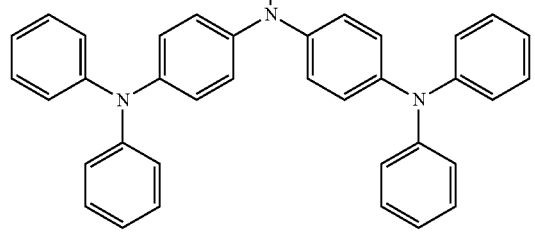

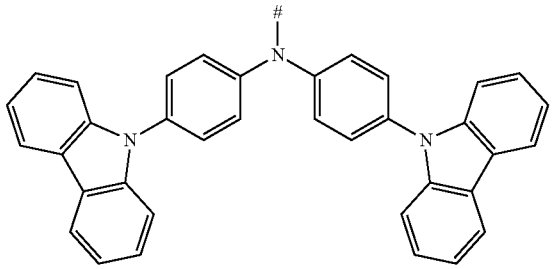

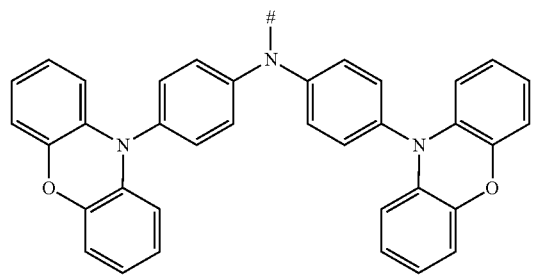

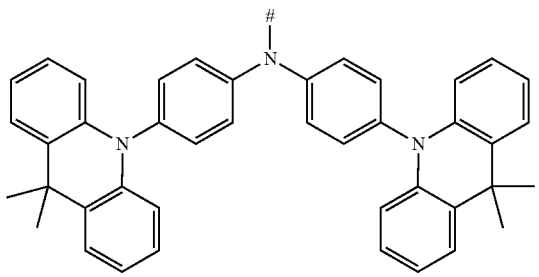

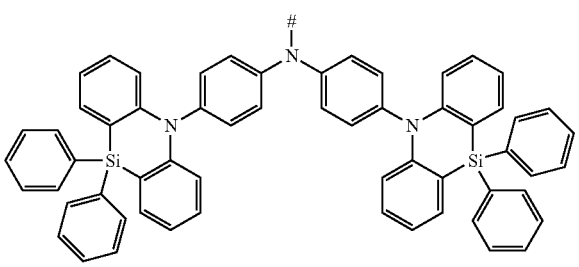

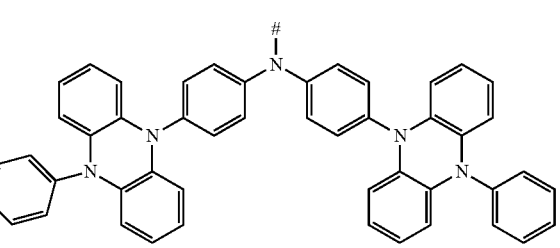

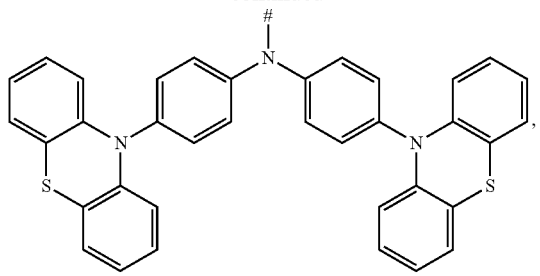
wherein # indicates a bonding position.
5. The aromatic heterocyclic compound according to claim 1, wherein the nitrogenous heterocyclic substituent is any one of following chemical groups:
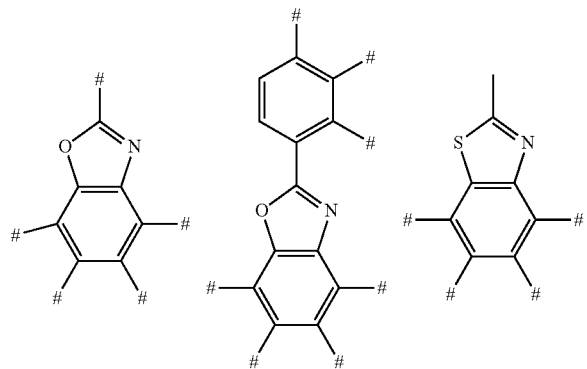
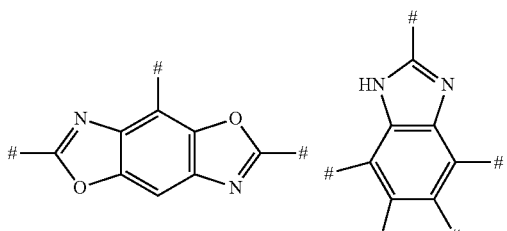
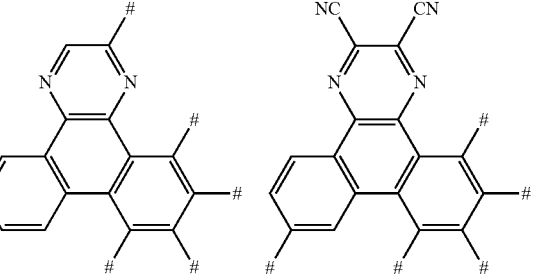

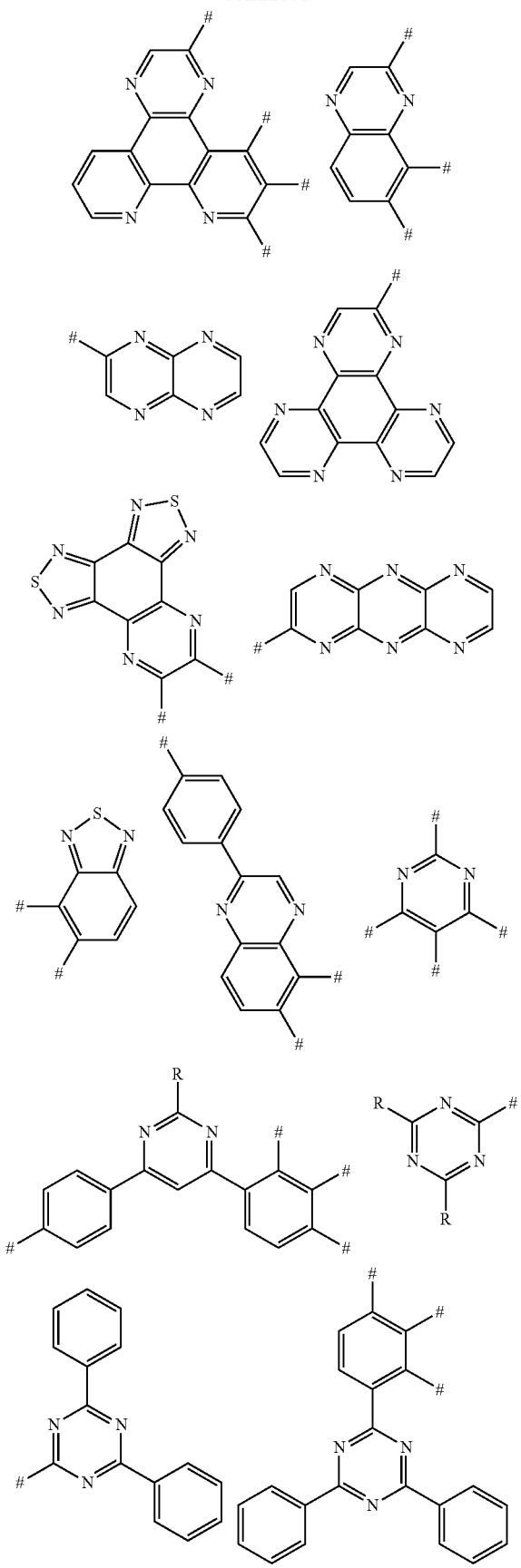
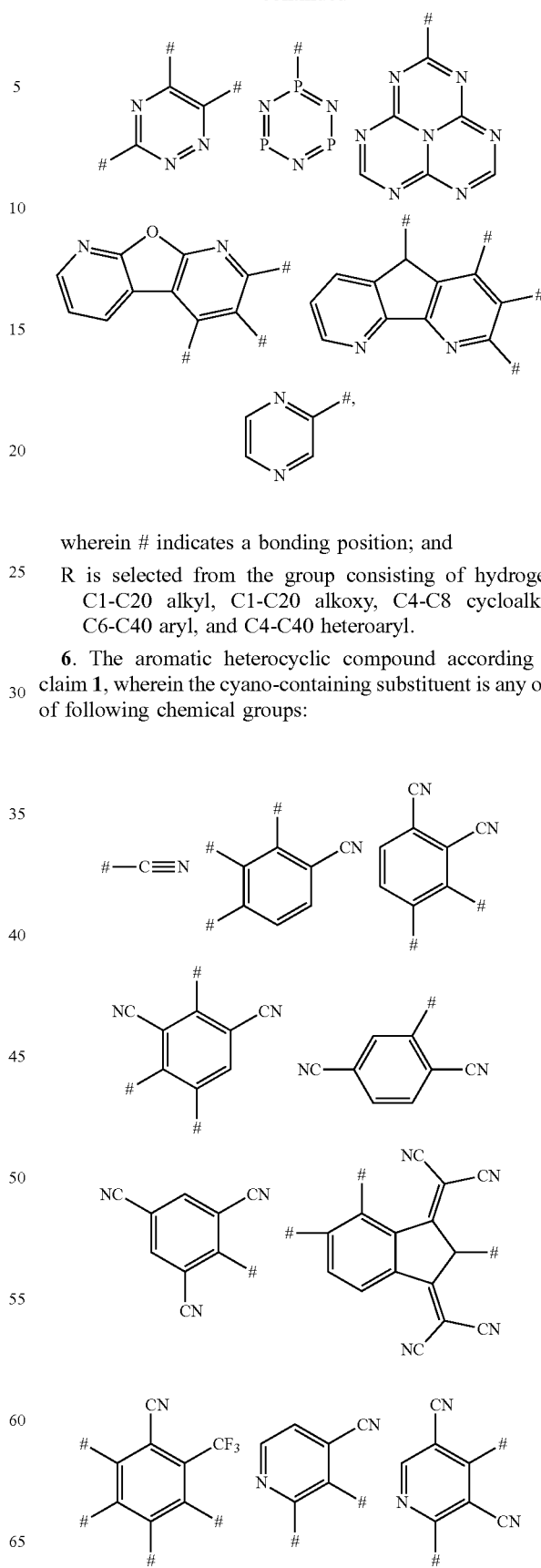
wherein # indicates a bonding position; and
R is selected from the group consisting of hydrogen, C1-C20 alkyl, C1-C20 alkoxy, C4-C8 cycloalkyl, C6-C40 aryl, and C4-C40 heteroaryl.
6. The aromatic heterocyclic compound according to claim 1, wherein the cyano-containing substituent is any one of following chemical groups:

-continued

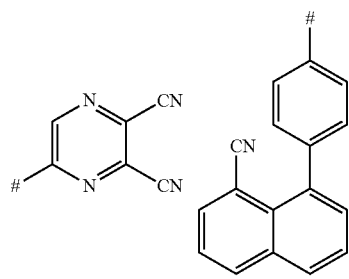

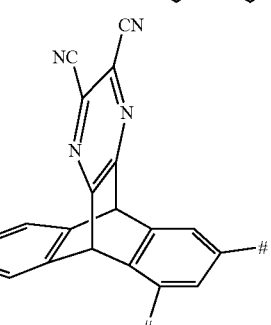

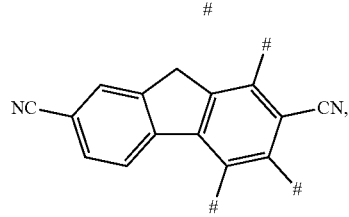

wherein # indicates a bonding position.

7. The aromatic heterocyclic compound according to claim 1, wherein the triaryl boron substituent is any one of following chemical groups:

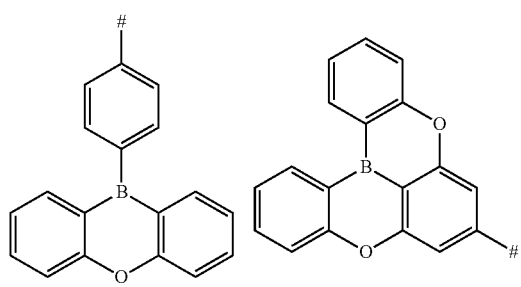

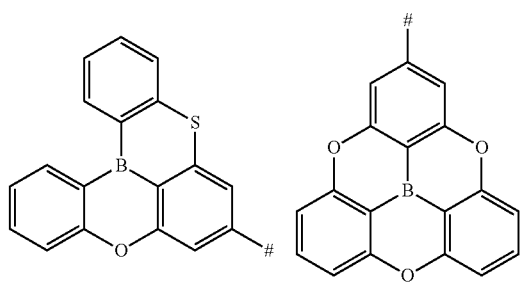

-continued

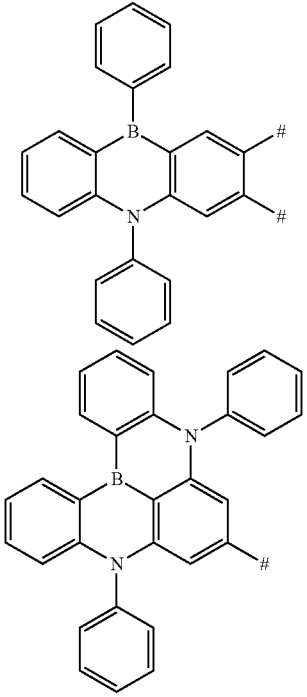

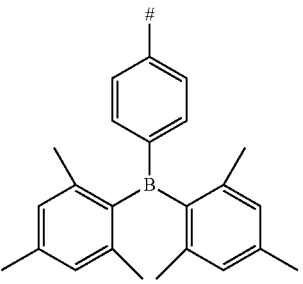

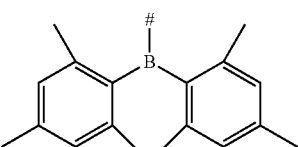

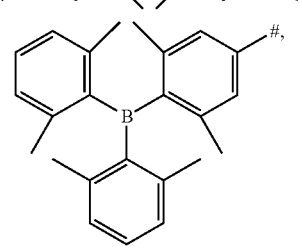

wherein # indicates a bonding position.

8. The aromatic heterocyclic compound according to claim 1, wherein the benzophenone substituent and the aromatic heterocyclic ketone substituent each is any one of following chemical groups:

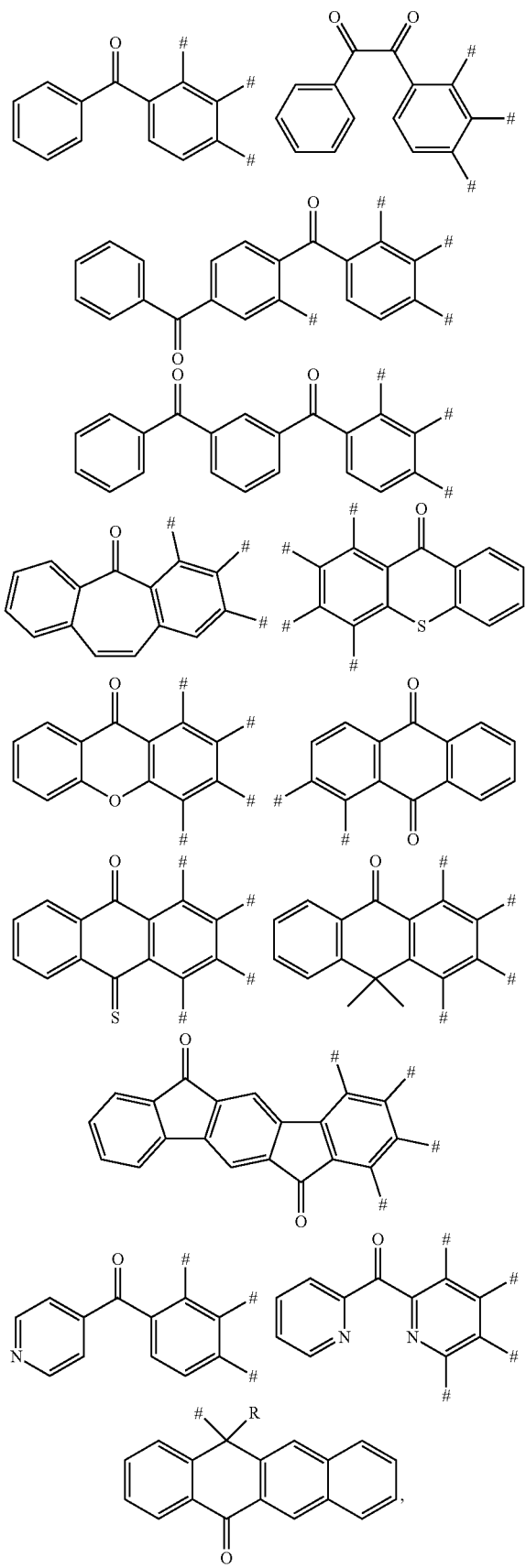

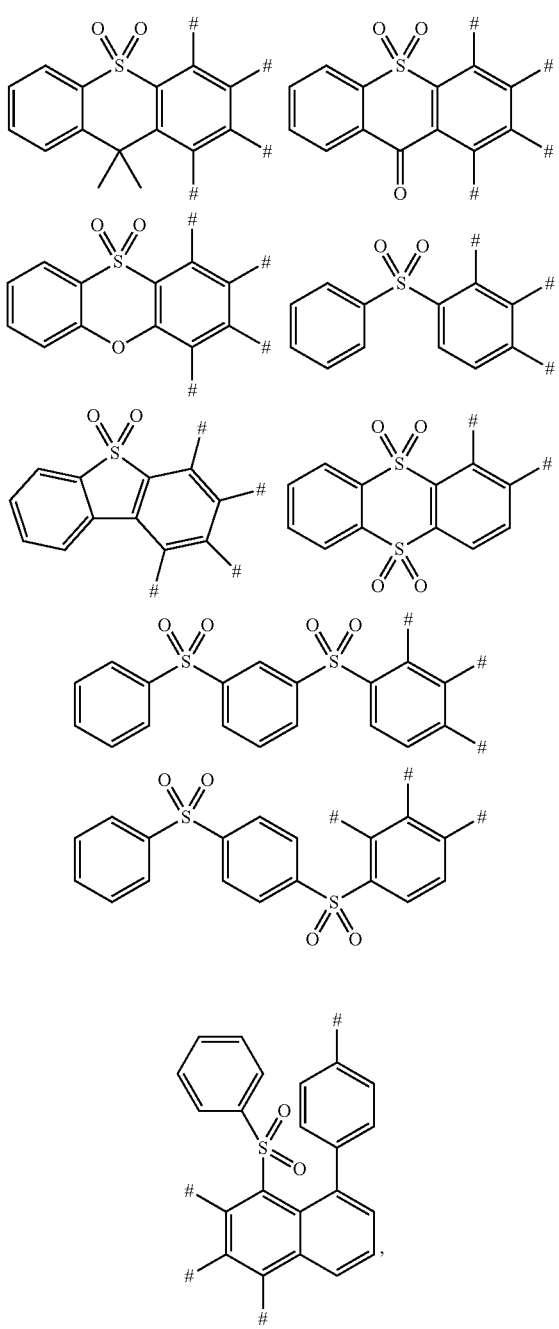

wherein # indicates a bonding position; and

R is selected from the group consisting of C1-C20 alkyl, C1-C20 alkoxy, C2-C20 alkenyl, C2-C20 alkynyl, C4-C8 cycloalkyl, C6-C40 aryl, and C4-C40 heteroaryl.

9. The aromatic heterocyclic compound according to claim 1, wherein the sulfone substituent is any one of following chemical groups:

wherein # indicates a bonding position.

10. The aromatic heterocyclic compound according to claim 1, wherein any one of the n electron acceptors A is any one of following chemical groups:

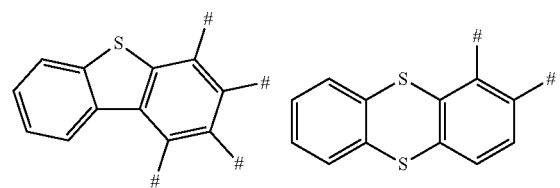
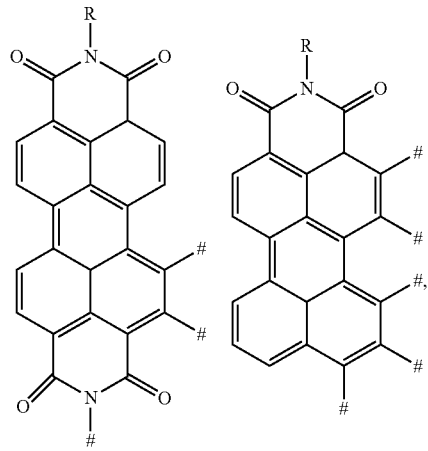
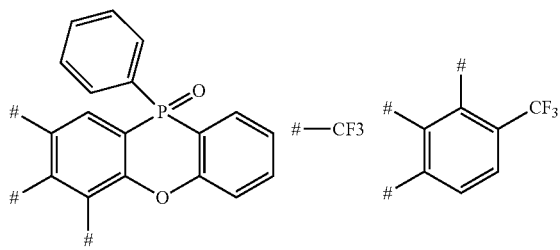
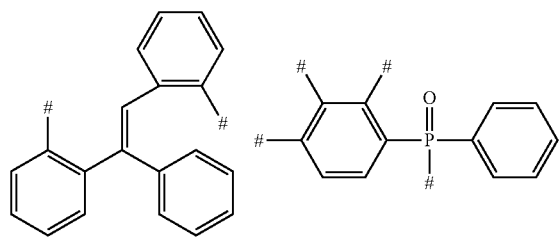
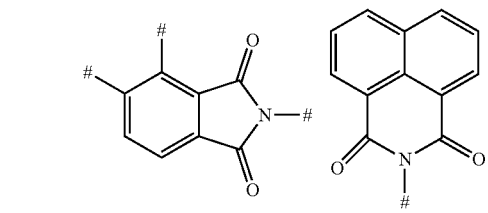
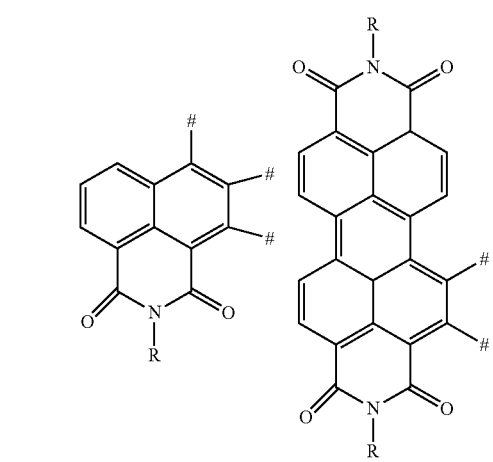
wherein # indicates a bonding position; and
R is selected from the group consisting of C1-C20 alkyl, C1-C20 alkoxy, C2-C20 alkenyl, C2-C20 alkynyl, C3-C8 cycloalkyl, C6-C40 aryl, and C4-C40 heteroaryl.
11. The aromatic heterocyclic compound according to claim 1, wherein the aromatic heterocyclic compound is any one of following compounds:
P1
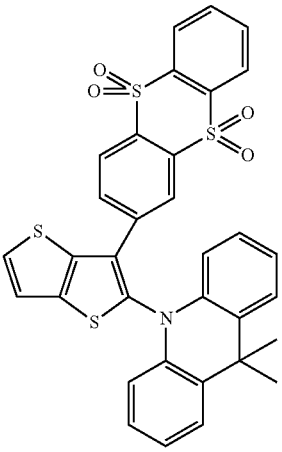
P2
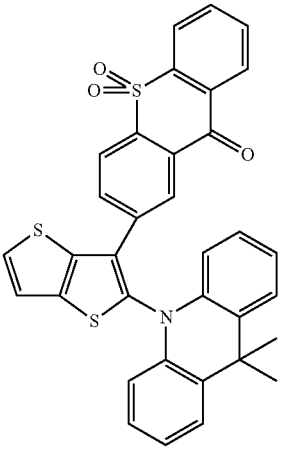

P3 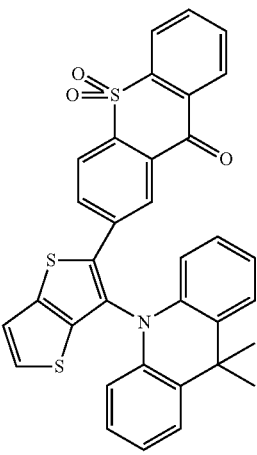
P4 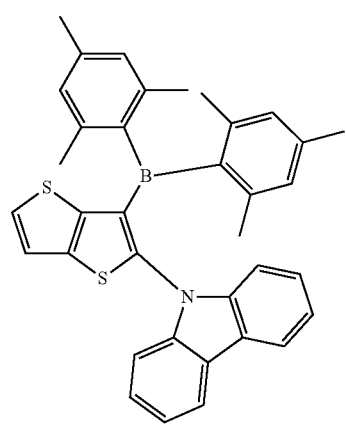
P5 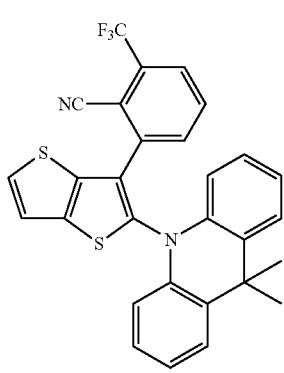
P6 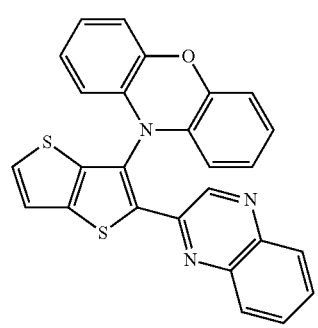
P7 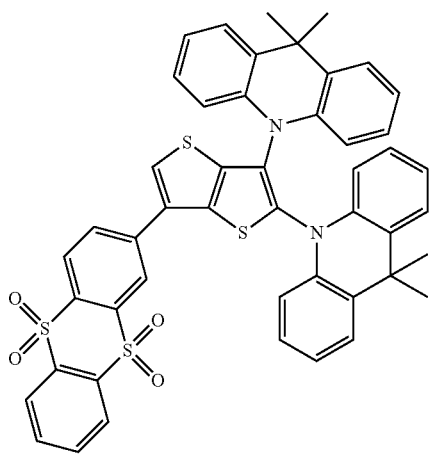
P8 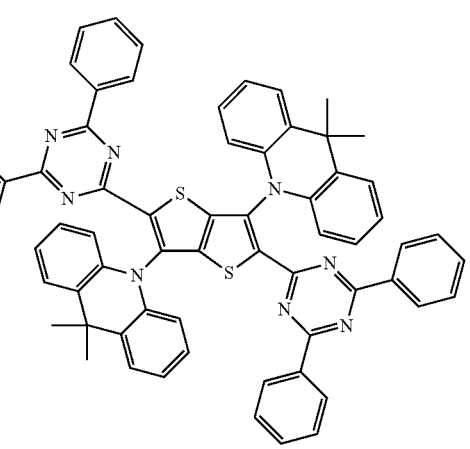
P9 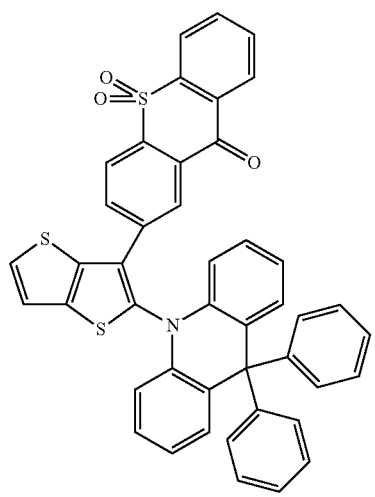

-continued
P10
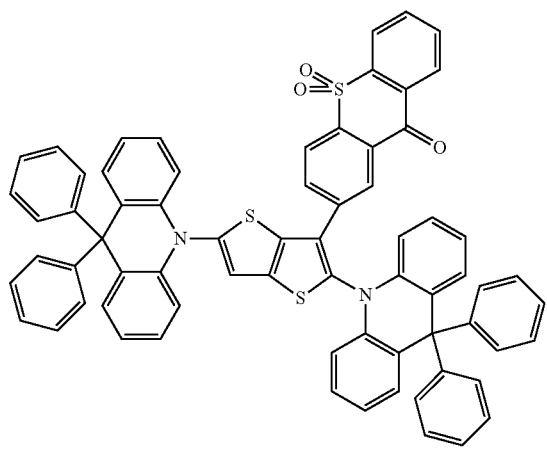
P11
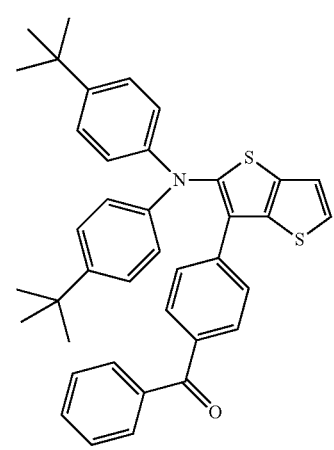
P12
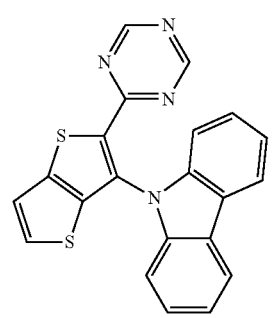
P13
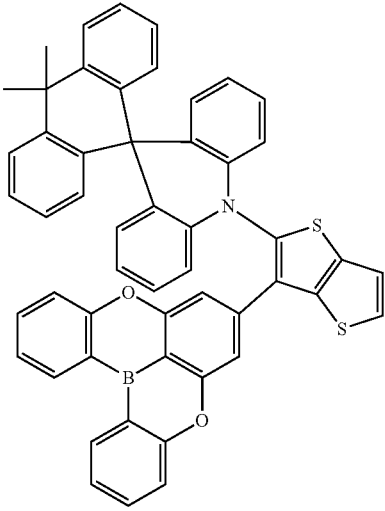
P14
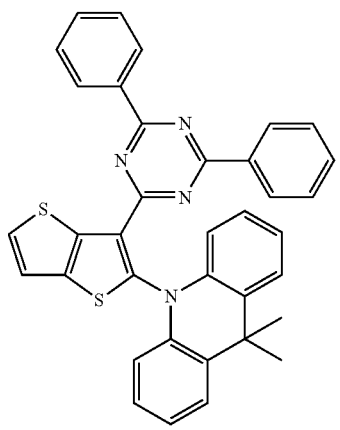
P15
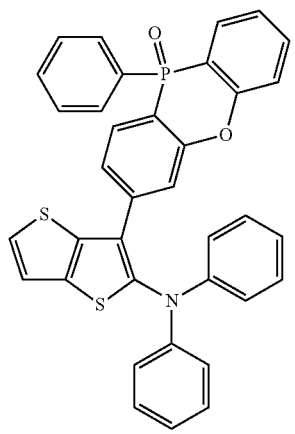
P16
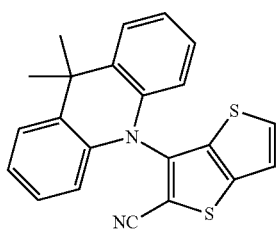

-continued
P17
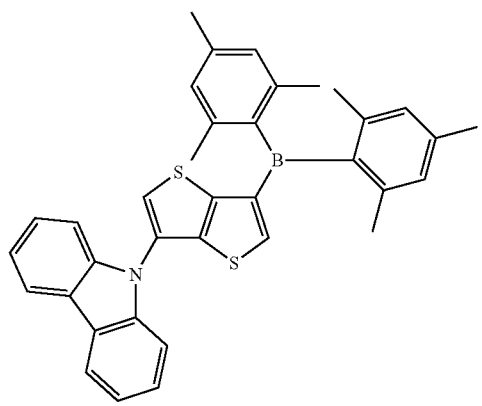
P18
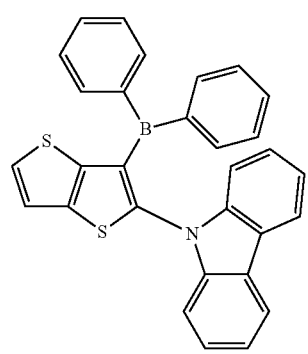
P19
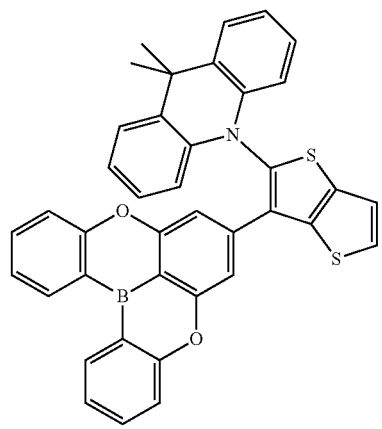
P20
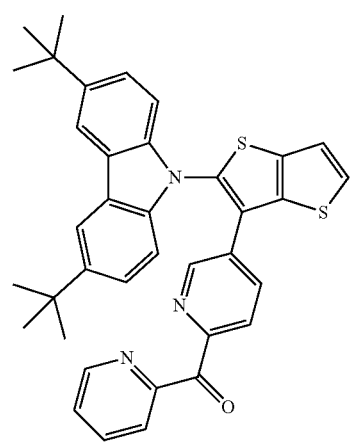
-continued
P21
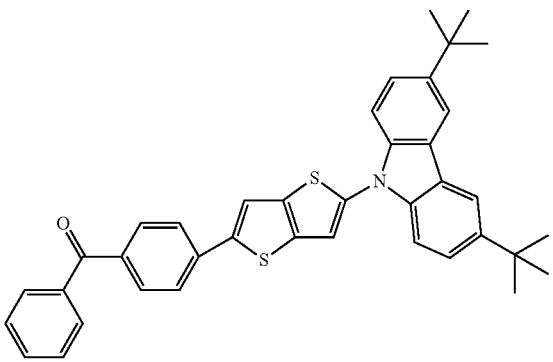
P22
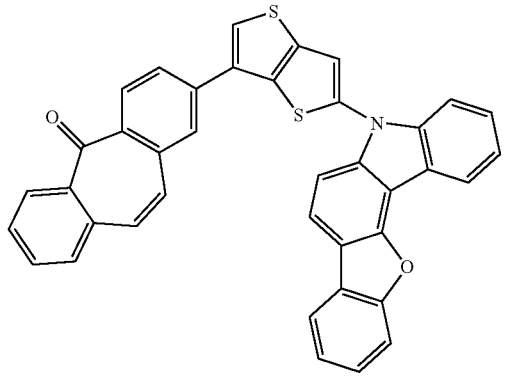
P23
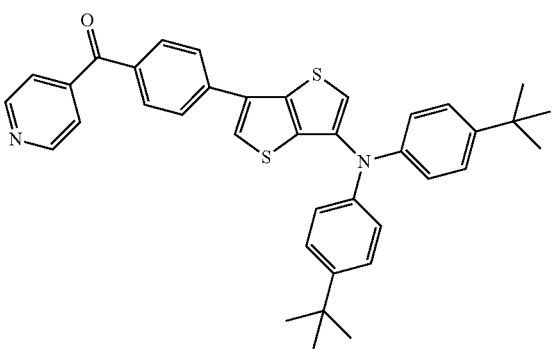
P24
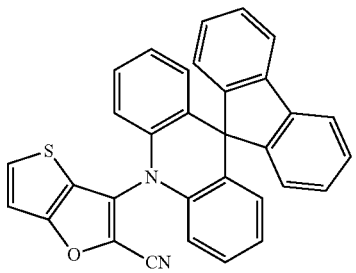
P25
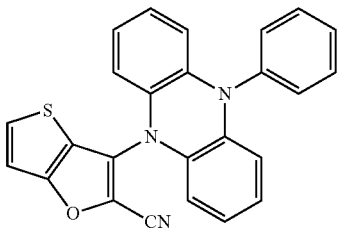

-continued
P26
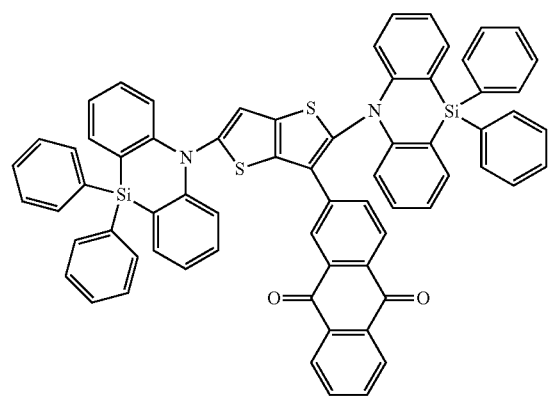
P27
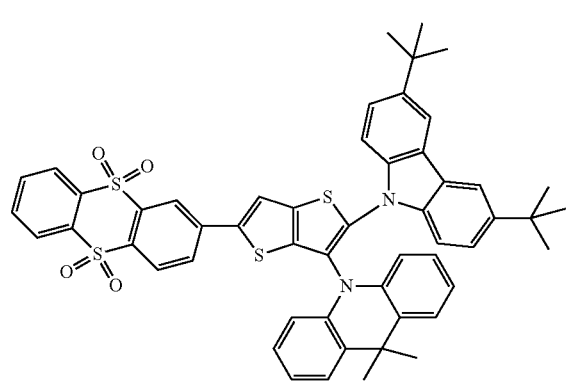
P28
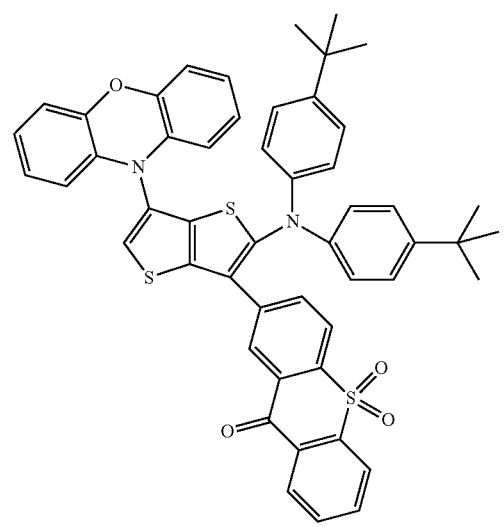
-continued
P29
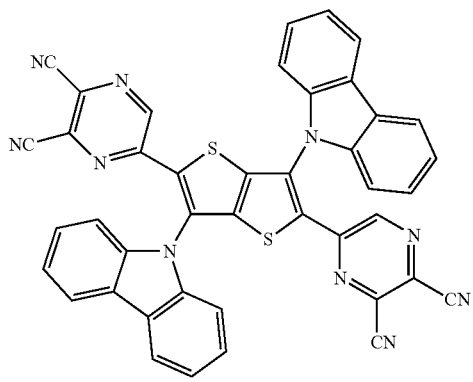
P30
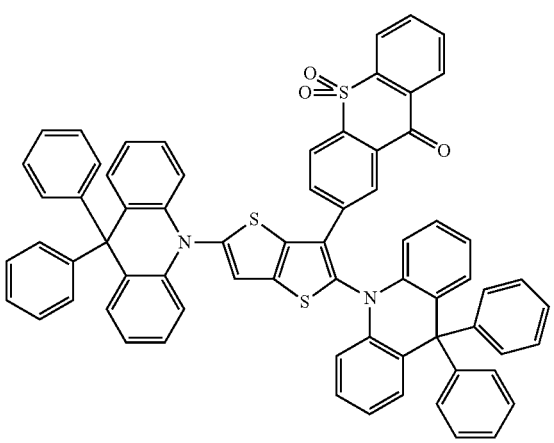
P31
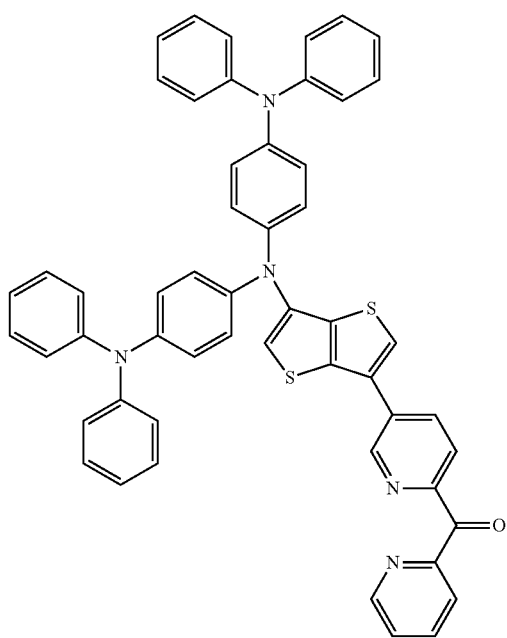

-continued
P32
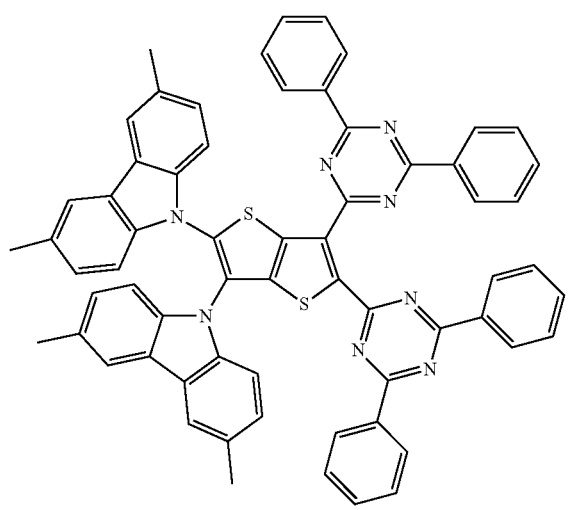
P33
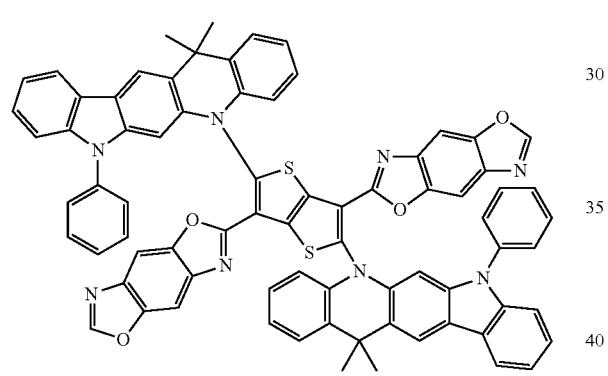
P34
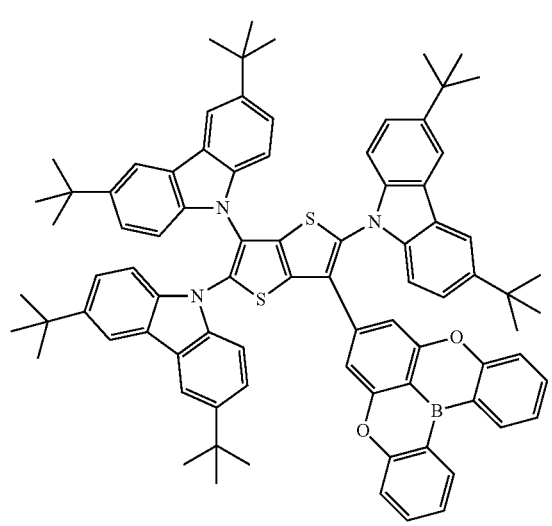
-continued
P35
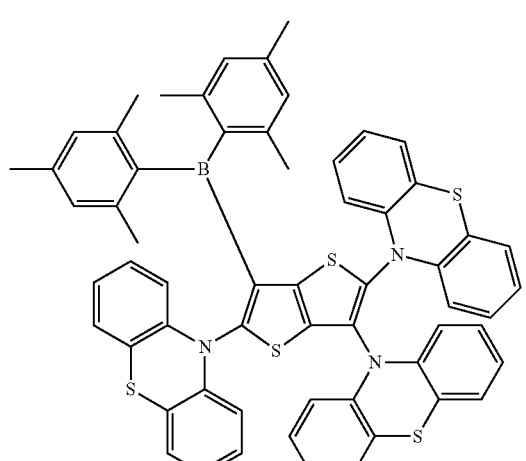
P36
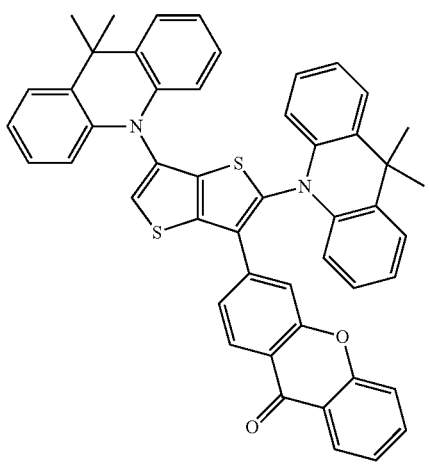
P37
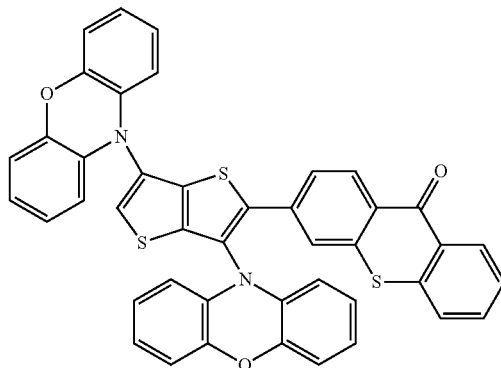

P38

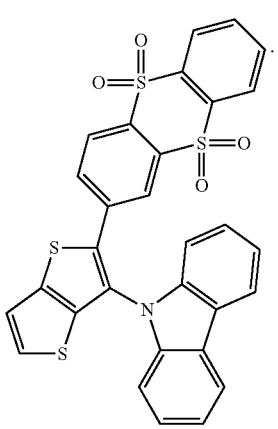

12. The aromatic heterocyclic compound according to claim 1, wherein the electron donor D and the electron acceptor A are bonded to the aromatic heterocyclic compound represented by the Formula (I) in an ortho-position.

13. The aromatic heterocyclic compound according to claim 1, wherein an energy difference $\Delta E_{st}$ between a lowest singlet energy level S1 of the aromatic heterocyclic compound and a lowest triplet energy level T1 of the aromatic heterocyclic compound satisfies an equation $\Delta E_{st}=E_{S1}-E_{T1} \leq 0.30$ eV.

14. The aromatic heterocyclic compound according to claim 1, wherein the aromatic heterocyclic compound is the following compound:

P1

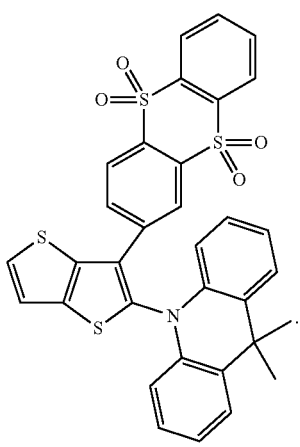

15. An organic light-emitting display device, comprising
an anode;
a cathode; and
a light-emitting layer disposed between the anode and the cathode, wherein a light-emitting material of the light-emitting layer comprises one or more aromatic heterocyclic compounds having a structure represented by Formula (I):

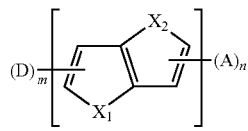

Formula (I)

wherein $X_1$ and $X_2$ are independently selected from S and O;
D is a chemical group acting as an electron donor,
A is a chemical group acting as an electron acceptor;
m is a number of the electron donors D, the m electron donors D are the same or different from one another;
n is a number of the electron acceptors A, the n electron acceptors are the same or different from one another; and
m and n are integers independently selected from 1 and 2;
wherein any one of the m electron donors D is any one of following chemical groups:

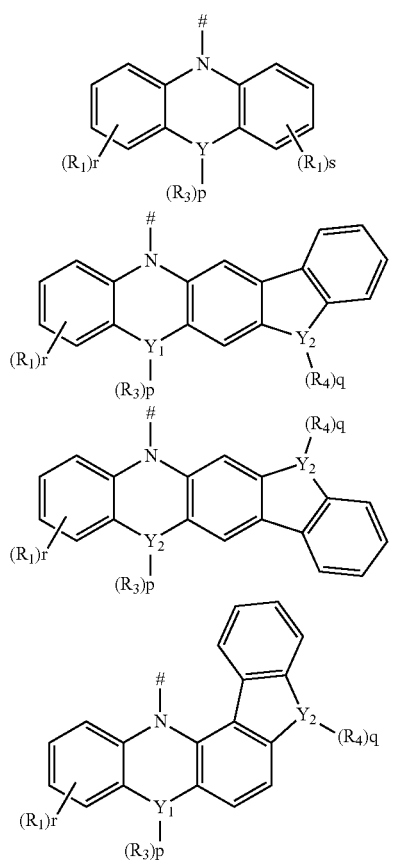

wherein Y, $Y_1$ and $Y_2$ are independently selected from the group consisting of carbon, nitrogen, oxygen, sulfur, and silicon;
indicates a bonding position;
r and s are integers independently selected from 0, 1, 2 and 3, and
p and q are integers independently selected from 0, 1 and 2;
when Y is oxygen or sulfur, p=0 or q=0;
when Y is nitrogen, p and q are independently selected from 0 and 1;

when Y is carbon or silicon, p and q are independently selected from 0, 1 and 2; and $R_1$, $R_2$, $R_3$ and $R_4$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C13-C40 acridinyl, substituted or unsubstituted C3-C40 azine group, and groups represented by Formula (21):

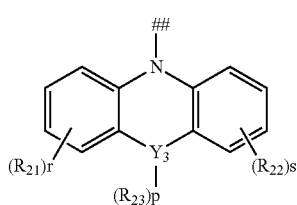

Formula (21)

wherein $Y_3$ is selected from the group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and ## indicates a bonding position; or any one of the m electron donors D is any one of following chemical groups:

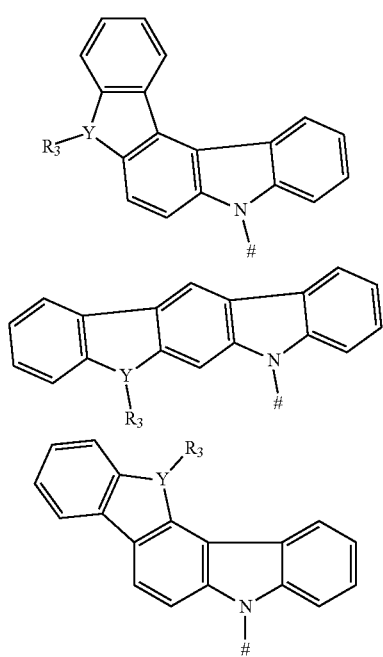

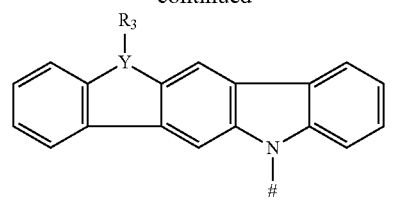

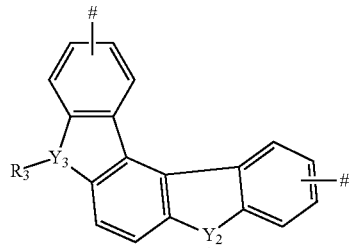

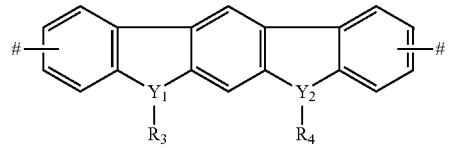

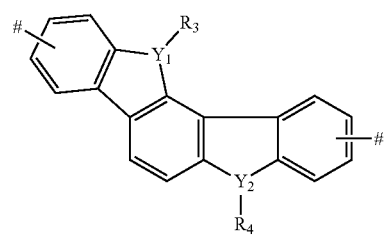

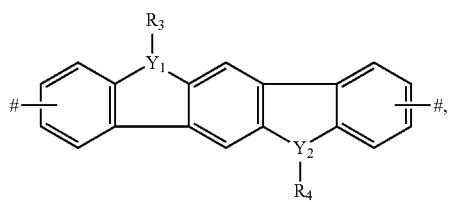

wherein Y, $Y_1$ and $Y_2$ are independently selected from the group consisting of carbon, nitrogen, oxygen, sulfur and silicon;

x and y are integers independently selected from 0, 1, 2 and 3;

indicates a bonding position;

when Y is oxygen or sulfur, $R_3$ is absent;

when $Y_1$ is oxygen or sulfur, $R_3$ is absent;

when $Y_2$ is oxygen or sulfur, $R_4$ is absent; and $R_1$, $R_2$, $R_3$ and $R_4$ are independently selected from the group consisting of hydrogen, C1-C20 alkyl, C1-C20 alkoxy, substituted or unsubstituted C6-C40 aryl, substituted or unsubstituted C4-C40 heteroaryl, substituted or unsubstituted C12-C40 carbazolyl, substituted or unsubstituted C12-C40 diphenylamino, substituted or unsubstituted C3-C40 azine group, and groups represented by formula (21):

87

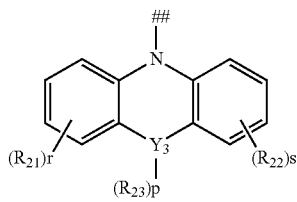

Formula (21)

wherein $Y_3$ is selected from a group consisting of carbon, nitrogen, oxygen, sulfur, and silicon;

$R_{21}$, $R_{22}$ and $R_{23}$ are independently selected from the group consisting of hydrogen, C1-C20 alkyl, C1-C20 alkoxy, substituted or unsubstituted C6-C40 aryl, and substituted or unsubstituted C4-C40 heteroaryl;

r and s are integers independently selected from 0, 1, 2 and 3, and p is an integer selected from 0, 1 and 2;

when $Y_3$ is oxygen or sulfur, p=0; and ## indicates a bonding position; or any one of the m electron donors D is any one of following chemical groups:

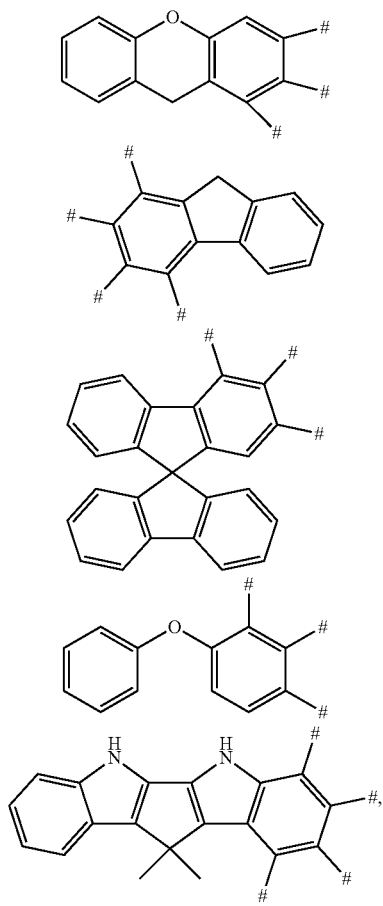

wherein # indicates a bonding position; and any one of the n electron acceptors A is selected from the group consisting of a cyano-containing substituent, a triaryl boron substituent, a benzophenone substituent, an aromatic heterocyclic ketone substituent, and a sulfone substituent.

88

16. The organic light-emitting display device according to claim 15, wherein the light-emitting material of the light-emitting layer, a light-emitting host material of the light-emitting layer or a light-emitting guest material of the light-emitting layer is selected from the group consisting of the aromatic heterocyclic compounds, and combinations thereof, the aromatic heterocyclic compounds having a structure represented by Formula (I):

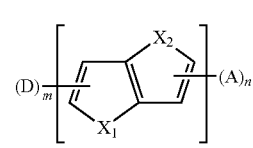

Formula (I)

wherein $X_1$ and $X_2$ are independently selected from S and O;

D is a chemical group acting as an electron donor,

A is a chemical group acting as an electron acceptor;

m is a number of the electron donors D, the m electron donors D are the same or different from one another;

n is a number of the electron acceptors A, the n electron acceptors are the same or different from one another; and m and n each is independently 1 or 2.

17. The organic light-emitting display device according to claim 15, wherein when the light-emitting material of the light-emitting layer is a red light-emitting material, the red light-emitting material has a singlet energy level of 1.61-1.99 eV;

when the light-emitting material of the light-emitting layer is a green light-emitting material, the green light-emitting material has a singlet energy level of 2.15-2.52 eV; and when the light-emitting material of the light-emitting layer is a blue light-emitting material, the blue light-emitting material has a singlet energy level of 2.52-2.73 eV.

18. The organic light-emitting display device according to claim 15, wherein the light-emitting layer comprises a host material and a guest material, the host material is selected from the group consisting of 2,8-bis(diphenylphosphinyl)dibenzothiophene, 4,4'-bis(9-carbazolyl)biphenyl, 3,3'-bis(N-carbazolyl)-1,1'-biphenyl, 2,8-bis(diphenylphosphinyl)dibenzofuran, bis(4-(9H-carbazolyl-9-yl)phenyl)diphenylsilane, 9-(4-tert-butylphenyl)-3,6-bis(triphenylsilyl)-9H-carbazole, bis(2-diphenylphosphinyl)diphenyl ether, 1,3-bis[3,5-di(pyridine-3-yl)phenyl]benzene, 4,6-bis(3,5-di(3-pyridyl)phenyl)-2-methylpyrimidine, 9-(3-(9H-carbazolyl-9-yl)phenyl)-9H-carbazole-3-cyano, 9-phenyl-9-[4-(triphenylsilyl)phenyl]-9H-fluorene, 1,3,5-tris(1-phenyl-1H-benzoimidazol-2-yl) benzene, diphenyl[4-(triphenylsilyl)phenyl]phosphine oxide, 4,4',4''-tris(carbazol-9-yl)triphenylamine, 2,6-dicarbazolyl-1,5-pyridine, polyvinylcarbazole, polyfluorene, and combinations thereof, the guest material is selected from the group consisting of aromatic heterocyclic compounds, and combinations thereof, the aromatic heterocyclic compounds having a structure represented by Formula (I):

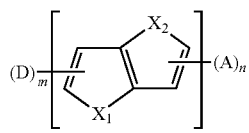

Formula (I)

wherein $X_1$ and $X_2$ are independently selected from S and O;
D is a chemical group acting as an electron donor,
A is a chemical group acting as an electron acceptor;
m is a number of the electron donors D, the m electron donors D are the same or different from one another;
n is a number of the electron acceptors A, the n electron acceptors are the same or different from one another; and
m and n are integers independently selected from 1 and 2,
an energy difference between a HOMO energy level of the host material and a HOMO energy level of the guest material is less than 0.6 eV, or an energy difference between a LUMO energy level of the host material and a LUMO energy level of the guest material is less than 0.6 eV.

19. The organic light-emitting display device according to claim 18, wherein a singlet energy level of the host material is higher than a singlet energy level of the guest material, and an energy difference between the singlet energy level of the host material and the singlet energy level of the guest material is less than 1.0 eV.

20. The organic light-emitting display device according to claim 15, wherein the light-emitting material of the light-emitting layer comprises a host material and a guest material,
the host material is selected from the group consisting of aromatic heterocyclic compounds, and combinations thereof, the aromatic heterocyclic compounds having a structure represented by Formula (I):

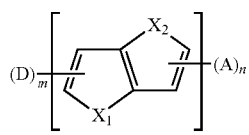

Formula (I)

wherein $X_1$ and $X_2$ are independently selected from S and O;
D is a chemical group acting as an electron donor,
A is a chemical group acting as an electron acceptor;
m is a number of the electron donors D, the m electron donors D are the same or different from one another;
n is a number of the electron acceptors A, the n electron acceptors are the same or different from one another; and
m and n are independently selected from 1 and 2,
the guest material is selected from the group consisting of a fluorescent material, a thermally activated delayed fluorescent material, and a phosphorescent material; and
an energy difference between a HOMO energy level of the host material and a HOMO energy level of the guest material is less than 0.6 eV, or an energy difference between a LUMO energy level of the host material and a LUMO energy level of the guest material is less than 0.6 eV.

21. The organic light-emitting display device according to claim 15, wherein the light-emitting material of the light-emitting layer comprises a host material and a guest material,
the host material is selected from a group consisting of an aromatic heterocyclic compound, and combinations thereof, the aromatic heterocyclic compounds having a structure represented by Formula (I):

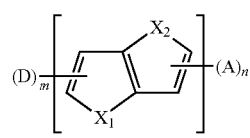

Formula (I)

wherein $X_1$ and $X_2$ are independently selected from S and O;
D is a chemical group acting as an electron donor,
A is a chemical group acting as an electron acceptor;
m is a number of the electron donors D, the m electron donors D are the same or different from one another;
n is a number of the electron acceptors A, the n electron acceptors are the same or different from one another; and
m and n are independently selected from 1 and 2,
the guest material is selected from the group consisting of a fluorescent material and a thermally activated delayed fluorescent material,
a singlet energy level of the guest material is lower than a singlet energy level of the host material, and an energy difference between the singlet energy level of the host material and the singlet energy level of the guest material is less than 1.0 eV.

22. The organic light-emitting display device according to claim 15, wherein the light-emitting material of the light-emitting layer comprises a host material and a guest material,
the host material is selected from a group consisting of an aromatic heterocyclic compounds, and combinations thereof, the aromatic heterocyclic compounds having a structure represented by Formula (I):

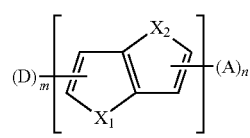

Formula (I)

wherein $X_1$ and $X_2$ are independently selected from S and O;
D is a chemical group acting as an electron donor,
A is a chemical group acting as an electron acceptor;
m is a number of the electron donors D, the m electron donors D are the same or different from one another;
n is a number of the electron acceptors A, the n electron acceptors are the same or different from one another; and
m and n are integers independently selected from 1 and 2,
the guest material is a phosphorescent material,
a triplet energy level of the guest material is lower than a triplet energy level of the host material, and an energy difference between the triplet energy level of the host material and the triplet energy level of the guest material is less than 1.0 eV.

\* \* \* \* \*